US009249071B2

(12) United States Patent
Strauss et al.

(10) Patent No.: US 9,249,071 B2
(45) Date of Patent: Feb. 2, 2016

(54) MODIFIED POLYAROMATIC HYDROCARBONS AND POLYHETEROCYCLICS FOR OPTOELECTRONICS

(71) Applicant: Colorado State University Research Foundation, Fort Collins, CO (US)

(72) Inventors: Steven H. Strauss, Fort Collins, CO (US); Olga V. Boltalina, Fort Collins, CO (US); Igor V. Kuvychko, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 14/174,780

(22) Filed: Feb. 6, 2014

(65) Prior Publication Data
US 2014/0221655 A1 Aug. 7, 2014

Related U.S. Application Data

(60) Provisional application No. 61/761,528, filed on Feb. 6, 2013.

(51) Int. Cl.
C07D 471/04 (2006.01)
C07C 17/32 (2006.01)
C07C 22/08 (2006.01)
C07C 22/02 (2006.01)

(52) U.S. Cl.
CPC ............. C07C 17/32 (2013.01); C07C 22/02 (2013.01); C07C 22/08 (2013.01); C07C 2102/30 (2013.01); C07C 2103/24 (2013.01); C07C 2103/26 (2013.01); C07C 2103/42 (2013.01); C07C 2103/52 (2013.01)

(58) Field of Classification Search
None
See application file for complete search history.

(56) References Cited

U.S. PATENT DOCUMENTS 3,281,426 A * 10/1966 Van Dyke Tiers ............ 540/140
7,390,901 B2 6/2008 Yang
2012/0208989 A1 8/2012 Sun

FOREIGN PATENT DOCUMENTS

WO 2011/022678 A1 2/2011

OTHER PUBLICATIONS

Dunyashev et al., Additivity of Electron-Affinity in a Series of Aromatic-Compounds During the Accumulation of Fluoroalkyl Substituents Based on Polarography and Theoretical Calculations of the MNDO Method.

Bravo, "New Methods of Free-Radical Perfluoroalkylation of Aromatics and Alkenes. Absolute Rate Constants and Partial Rate Factors for the Homolytic Aromatic Substitution by n-Perfluorobutyl Radical", J. Org. Chem., 21:7128-7136 (1997).
Cowell, "Fluoroalkylation of Aromatic Compounds", Journal of Fluorine Chemistry, 17:345-356 (1981).
Freskos, "A Convenient Synthesis of Pentafluoroethyl-substituted Aromatics", Journal: Synthetic communications,18(9):965-972 (1988).
Hosokawa et al., "Synthesis of Beta-Trifluoromethylnaphthalene Derivatives", Gov't Industrial Research Institute, 2:383-386 (1972). (With English Abstract).
Hosokawa et al., "Synthesis of (Trifluoromethyl)naphthalenes", Gov't Industrial Research Institute, 11:1791-1793 (1976). (With English Abstract).
Hosokawa et al., "Synthesis Bis(trifluoromethyl)naphthalenes", Gov't Industrial Research Institute, 8:1163-1167 (1977). (With English Abstract).
Hosokawa et al., "Synthesis of substituted (Trifluoromethyl)naphthalenes", Gov't Industrial Research Institute, 2:294-296 (1979). (With English Abstract).
Krespan et al., "Bis-(polyfluoroalkyl)-acetylenes. II. Bicyclooctatrienes Through 1,4-Addition of Bis-(polyfluoroalkyl)-acetylenes to Aromatic Rings", Synthesis of Bicyclooctatrienes, Contribution No. 648 from the Central Research Department, Experimental Station, 83:3428-3432 (1961).
Klebach et al., "Compounds Containing Localized Carbon-Phosphorus Double Bonds I. Diels-Alder Reaction of 3-Methyl-2-Phosphanaphtahlene with Hexafluorobutyne-2." Pergamon Press, Tetrahedron Letters 12:1099-1100 (1978).
Kuvychko et al., "Taming Hot CF3 Radicals: Incrementally Tuned Families of Polyarene Electron Acceptors for Air-Stable Molecular Optoelectronics", Angew. Chem. Int. Ed, 52:4871-4874 (2013).

(Continued)

Primary Examiner — Heidi Reese
(74) Attorney, Agent, or Firm — Haukaas Fortius PLLC; Michael H. Haukaas

(57) ABSTRACT

The invention provides methods for substituting polyaromatic hydrocarbons or polyheterocyclic compounds with perfluoroalkyl groups. The methods can include heating a polyaromatic hydrocarbon substrate or a polyheterocyclic compound substrate in the presence of a perfluoroalkyl iodide, typically in a closed system, wherein the heating is sufficient to bring both the polyaromatic hydrocarbons or polyheterocyclic compound, and the perfluoroalkyl iodide, into the gas phase, thereby allowing the substrate to react with the perfluoroalkyl iodide in the gas phase to form polyaromatic hydrocarbons or polyheterocyclic compounds having one or more perfluoroalkyl substituents. The methods allow for the creation of versatile libraries of novel perfluoroalkyl-containing derivatives that can serve as important building blocks and active components in biomedical, electronic, and materials applications.

19 Claims, 22 Drawing Sheets

(56) References Cited

OTHER PUBLICATIONS

Roy et al., "Tetrahedron report No. 933: Trifluoromethylation of aryl and heteroaryl halides", Tetrahedron, 67:2161-2195 (2011).
Sun et al., "Arene Trifluoromethylation: An Effective Strategy to Obtain Air-Stable n-Type Organic Semiconductors with TunableOptoelectronic and Electron Transfer Properties", J. Phys. Chem. A., 116:8015-8022 (2012).
Tiers, "Perfluoroalkylation of Aromatic Compounds", Communications to the Editor JACS, Contribution No. 182 from the Central Research Dept of 3M, pp. 5513 (1960).

* cited by examiner

AZUL-5-1: 1,2,3,5,7-AZUL(CF$_3$)$_5$

NAPH(CF$_3$)$_4$            NAPH(C$_2$F$_5$)$_4$

NAPH(n-C$_3$F$_7$)$_4$            NAPH(n-C$_4$F$_9$)$_4$

A.

B.

AZULENE(CF$_3$)$_n$ = C$_{10}$H$_{8-n}$(CF$_3$)$_n$

| # | Chemical formula | Name | Structure By: | |
|---|---|---|---|---|
| 1 | AZUL-3-1 | C$_{13}$H$_5$F$_9$ | 1,3,5-AZUL(CF$_3$)$_3$ | NMR | |
| 2 | AZUL-3-2 | C$_{13}$H$_5$F$_9$ | 1,3,6-azulene(CF$_3$)$_3$ | NMR | |
| 3 | AZUL-3-3 | C$_{13}$H$_5$F$_9$ | 1,2,3-AZUL(CF$_3$)$_3$ | NMR | |
| 4 | AZUL-4-1 | C$_{14}$H$_4$F$_{12}$ | 1,3,5,7-AZUL(CF$_3$)$_4$ | X-ray | |
| 5 | AZUL-4-2 | C$_{14}$H$_4$F$_{12}$ | 1,2,3,5-AZUL(CF$_3$)$_4$ | X-ray | |
| 6 | AZUL-4-3 | C$_{14}$H$_4$F$_{12}$ | 1,2,3,6-AZUL(CF$_3$)$_4$ | X-ray | |
| 7 | AZUL-5-1 | C$_{15}$H$_3$F$_{15}$ | 1,2,3,5,7-AZUL(CF$_3$)$_5$ | X-ray | |

*Figure 21*

NAPHTHALENE$(R_F)_n$ = $C_{10}H_{8-n}(CF_3)_n$

| # | | Chemical formula | Name | Structure By: | |
|---|---|---|---|---|---|
| 1 | NAPH-C2F5-2-1 | $C_{14}H_6F_{10}$ | 1,5-NAPH$(C_2F_5)_2$ | NMR | |
| 2 | NAPH-C2F5-3-1 | $C_{16}H_5F_{15}$ | 1,3,6-NAPH$(C_2F_5)_3$ | NMR |  |
| 2 | NAPH-C2F5-3-2 | $C_{16}H_5F_{15}$ | 1,3,7-NAPH$(C_2F_5)_3$ | NMR |  |
| 3 | NAPH-4-1 | $C_{14}H_6F_{12}$ | 1,3,5,7-NAPH$(CF_3)_4$ | X-ray | |
| 4 | NAPH-C2F5-4-1 | $C_{18}H_4F_{20}$ | 1,3,5,7-NAPH$(C_2F_5)_4$ | X-ray | |
| 5 | NAPH-C3F7-4-1 | $C_{22}H_4F_{28}$ | 1,3,5,7-NAPH$(C_3F_7)_4$ | NMR | |
| 6 | NAPH-C4F9-4-1 | $C_{26}H_4F_{36}$ | 1,3,5,7-NAPH$(C_3F_7)_4$ | NMR | |

ANTHRACENE(CF$_3$)$_n$

| # |  | Chemical formula | Name | Structure By: |  |
|---|---|---|---|---|---|
| 1 | ANTH-5-1 | C$_{19}$H$_5$F$_{15}$ | 1,3,6,8,10-ANTH(CF$_3$)$_5$ | X-ray |  |
| 2 | ANTH-6-1 | C$_{34}$H$_{14}$F$_{18}$ | 2,3,6,7,9,10-ANTH(CF$_3$)$_6$ | X-ray |  |
| 3 | ANTH-6-2 | C$_{34}$H$_{14}$F$_{18}$ |  | NMR |  |

PERYLENE(CF$_3$)$_n$

| # |  | Chemical formula | Name | Structure By: |  |
|---|---|---|---|---|---|
| 1 | PERY-4-1 | C$_{24}$H$_8$F$_{12}$ | 1,4,7,10-PERY(CF$_3$)$_4$ | X-ray |  |
| 2 | PERY-5-1 | C$_{25}$H$_7$F$_{15}$ | 1,3,6,8,10-PERY(CF$_3$)$_5$ | X-ray |  |
| 3 | PERY-5-2 | C$_{25}$H$_7$F$_{15}$ |  | NMR |  |
| 4 | PERY-5-3 | C$_{25}$H$_7$F$_{15}$ |  | NMR |  |
| 5 | PERY-5-4 | C$_{25}$H$_7$F$_{15}$ |  | NMR |  |
| 6 | PERY-6-1 | C$_{26}$H$_6$F$_{18}$ | 1,3,5,7,9,11-PERY(CF$_3$)$_6$ | NMR |  |

PHENANTHRENE(CF$_3$)$_n$

| # |  | Molecular formula | Name | Structure By: |  |
|---|---|---|---|---|---|
| 1 | PHEN-5-1 | C$_{19}$H$_5$F$_{15}$ | 1,3,6,7,9-PHEN(CF$_3$)$_5$ | X-ray |  |

PYRENE(CF$_3$)$_n$

| # |  | Molecular formula | Name | Structure By: |  |
|---|---|---|---|---|---|
| 1 | PYRN-5-1 | C$_{21}$H$_5$F$_{15}$ | 1,3,4,6,8-PYRN(CF$_3$)$_5$ | X-ray |  |
| 2 | PYRN-5-2 | C$_{21}$H$_5$F$_{15}$ | 1,3,4,6,9-PYRN(CF$_3$)$_5$ | X-ray |  |
| 3 | PYRN-5-3 | C$_{21}$H$_5$F$_{15}$ |  | NMR |  |
| 4 | PYRN-6-1 |  | 1,3,4,6,8,9-PYRN(CF$_3$)$_6$ | X-ray |  |

TRIPHENYLENE(CF3)n

| # | | Molecular formula | Name | Structure By: | |
|---|---|---|---|---|---|
| 1 | TRPH-5-1 | | | NMR | |
| 2 | TRPH-6-1 | $C_{24}H_6F_{18}$ | 1,3,6,7,10,11-TRPH(CF$_3$)$_6$ | X-ray |  |
| 3 | TRPH-6-2 | $C_{24}H_6F_{18}$ | 1,3,6,8,10,11-TRPH(CF$_3$)$_6$ | NMR |  |

Table F21. Experimental Data for PAH and PAH(CF$_3$)$_n$ Compounds

| compound | abbrev. | gas-phase EA, eV | solution $E_{1/2}$ V vs. Fe(Cp)$_2^{+/0}$ | X-ray structure |
|---|---|---|---|---|
| pentacene | PENT | 1.39(4) | — | — |
| PENT(CF$_3$)$_8$ | mixture of isomers | 3.32(2) | — | no |
| perylene | PERY | 0.973(5) | −2.23 | — |
| PERY(CF$_3$)$_7$ | mixture of isomers | 2.91(2) | — | no |

US 9,249,071 B2

MODIFIED POLYAROMATIC HYDROCARBONS AND POLYHETEROCYCLICS FOR OPTOELECTRONICS

RELATED APPLICATIONS

This application claims priority under 35 U.S.C. §119(e) to U.S. Provisional Patent Application No. 61/761,528, filed Feb. 6, 2013, which is incorporated herein by reference.

GOVERNMENT SUPPORT

This invention was made with government support under Grant No. CHE1012468 awarded by the National Science Foundation. The government has certain rights in the invention.

BACKGROUND OF THE INVENTION

The renaissance in the synthesis of small organic molecules with strong electron-accepting properties (i.e., organic semiconductors (OSCs)) during the past decade has been spurred by the global economic needs of (i) renewable sources of energy and (ii) more efficient and less expensive electronic devices that preferably include earth-abundant elements. The replacement of silicon- and metal-based electronic components with rationally-designed, finely-tuned organic molecules and molecular assemblies should lead to sustainable, lower-cost, lower-weight, flexible, yet robust solutions to many $21^{st}$ century technological problems. Significant progress in this endeavor requires a deep understanding of the fundamental relationships between molecular structure, solid-state morphology, and electronic and other physicochemical properties of OSCs.

It has long been recognized that the presence of electron withdrawing groups (e.g., halogen atoms, cyanide, perfluoroalkyl ($R_F$), or perfluoroaryl groups) in polycyclic aromatic hydrocarbons (PAHs) results in molecules with enhanced electron acceptor properties, better air stability, and improved solid-state charge-carrier mobilities. In particular, organic transistors made with the few available PAH acceptors bearing $R_F$ groups have long-term air-stability, which can be correlated with either low LUMO energies (ca. −4 eV; estimated by cyclic voltammetry), or with DFT-predicted gas-phase electron affinities (EAs) above 2.8 eV (believed to be the threshold value for n-channel-device air stability. The arsenal of synthetic methods used in the past to prepare PAHs with one or more $R_F$ substituents include (i) bottom-up design involving multi-step coupling reactions of smaller precursors already bearing an $R_F$ group (U.S. Pat. No. 7,390,901 (Yang et al.); Geib et al., *J. Org. Chem.* 2012, 77, 6107-6116), (ii) metal-catalyzed reactions in solution for modification of PAH intermediates that have reactive substituents such as Cl or Br atoms, intermediates that are themselves not commercially available (Schlosser, *Angew. Chem. Int. Ed.* 2006, 45, 5432-5446; Tomashenko and Grushin, *Chem. Rev.* 2011, 111, 4475-4521), and (iii) direct perfluoroalkylation of PAHs (Bravo at al., *J. Org. Chem.* 1997, 62, 7128-7136). However, the latter method has not been extensively studied, possibly because the low yields and poor regioselectivities reported were not encouraging (Tiers, *J. Amer. Chem. Soc.* 1960, 82, 5513-5513; b) Cowell and Tamborski, *J. Fluorine Chem.* 1981, 17, 345-356).

Accordingly, there is a need for new methods for the direct perfluoroalkylation of PAHs and related aromatic and heteroaromatic compounds. There is also a need for new small organic molecules with strong electron-accepting properties, for example, for use as organic semiconductors in electronic devices.

SUMMARY

The invention provides a method for the direct perfluoroalkylation of polyaromatic hydrocarbons and polyheterocyclic compounds. The method can be carried out in a single step by combining reactants in the gas phase to provide new compounds with unprecedented substitution patterns.

Accordingly, the invention provides methods for substituting polyaromatic hydrocarbons or polyheterocyclic compounds with perfluoroalkyl groups comprising: heating a polyaromatic hydrocarbon substrate or a polyheterocyclic compound substrate in the presence of a perfluoroalkyl iodide, in an optionally closed reaction system, wherein the heating is sufficient to bring both the polyaromatic hydrocarbons or polyheterocyclic compound, and the perfluoroalkyl iodide, into the gas phase, thereby allowing the substrate to react with the perfluoroalkyl iodide in the gas phase to form polyaromatic hydrocarbons or polyheterocyclic compounds having one or more perfluoroalkyl substituents.

In one embodiment, the reaction system is a closed system able to withstand the high temperatures and high pressures of the reaction conditions described herein. The reaction system contains the substrate and perfluoroalkyl iodide, and these reactants can be heated to about 200° C. to about 550° C., typically to about 250° C. to about 450° C., to about 300° C. to about 400° C., or to about 300° C. to about 360° C. Additional pressure can be added to the system.

In one embodiment, the reaction system is a closed system that provides an increased atmospheric pressure upon heating. In another embodiment, the reaction system is a flowing bed reactor system having input valves for adding substrate and the perfluoroalkyl iodide, and an outlet for collecting products in the gas or liquid phase.

In some embodiments, the reaction system does not comprise a catalyst and/or a reaction promoter compound (e.g., a metal or salt to promote the reaction). In various embodiments, the reaction system does not comprise a solvent.

In various embodiments, the perfluoroalkyl iodide is $CF_3(CF_2)_nI$, wherein n is 0 to about 12. Thus, in some embodiments, n can be 0, 1, 2, 3, 4, 5, 6, 7, 8, 9, 10, 11, or 12.

In certain specific embodiments, the perfluoroalkyl iodide is $CF_3I$, $C_2F_5I$, n-$C_3F_7I$, or n-$C_4F_9I$. Other commercially available or synthetically preparable perfluoroalkyl iodide can readily be used in the method.

In one embodiment, the substrate is a polyaromatic hydrocarbon substrate. In certain specific embodiments, the polyaromatic hydrocarbon substrate is anthracene, azulene, coronene, fluorene, fluoranthene, naphthalene, pentacene, perylene, phenanthrene, pyrene, tetracene, or triphenylene, or another polyaromatic hydrocarbon described herein.

In one embodiment, the substrate is a polyheterocyclic compound substrate. In certain specific embodiments, the polyheterocyclic compound substrate is acridine, beta-carboline, 9H-carbazole, iminodibenzyl, indole, isoquinoline, phenanthridine phenanthroline, phenazine, phenothiazine, quinazoline, or quinoline, or a polyheterocyclic compound described herein.

In one embodiment, the polyaromatic hydrocarbon having one or more perfluoroalkyl substituents formed is a compound of Formula (I):

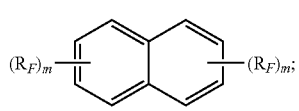

(I)

wherein $R_F$ is —$(CF_2)_nCF_3$ wherein n is 0 to about 11; and each m is independently 1 to 3.

In some embodiments, the compound of Formula (I) is:

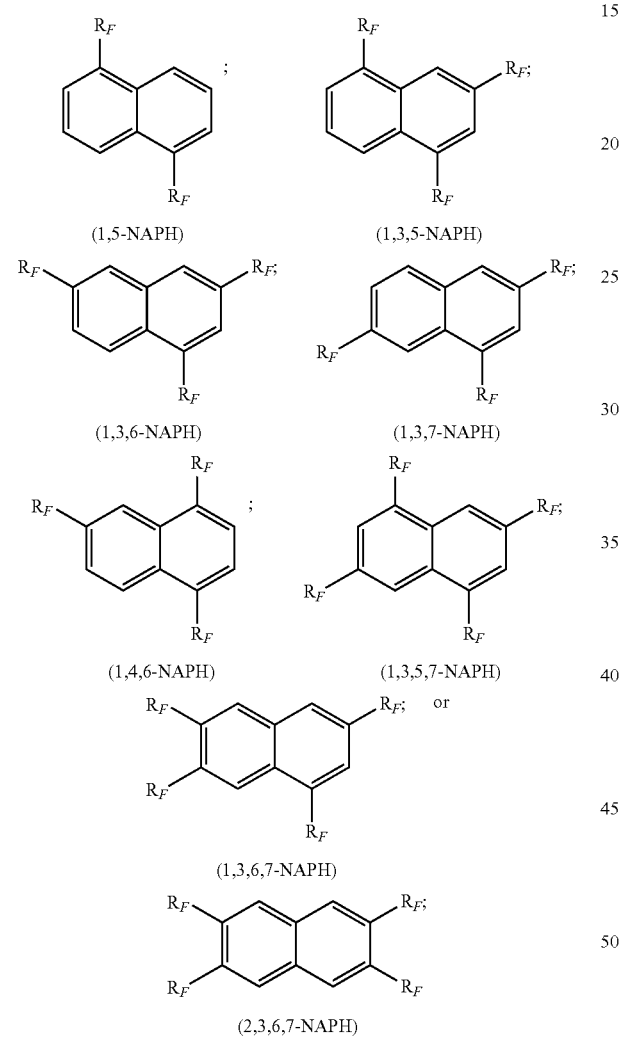

wherein $R_F$ is —$(CF_2)_nCF_3$ wherein n is 0 to about 11. In certain specific embodiments, the naphthalene core is substituted with the perfluoroalkyl substituent to provide 1,2-, 1,3-, 1,4-, 1,5-, 2,5-, 2,6-, 1,8-, or 2,8-substituted naphthalene compounds. Combinations of the aforementioned compounds can be prepared, and these compounds can also include a third or fourth perfluoroalkyl substituent in one of the remaining positions.

In various embodiments, the polyaromatic hydrocarbon having one or more perfluoroalkyl substituents formed is a compound of Formula (II):

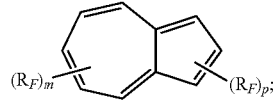

(II)

wherein $R_F$ is —$(CF_2)_nCF_3$ wherein n is 0 to about 11;

m is 0 to 3; and p is 1 to 3.

In other embodiments, the compound of Formula (II) is:

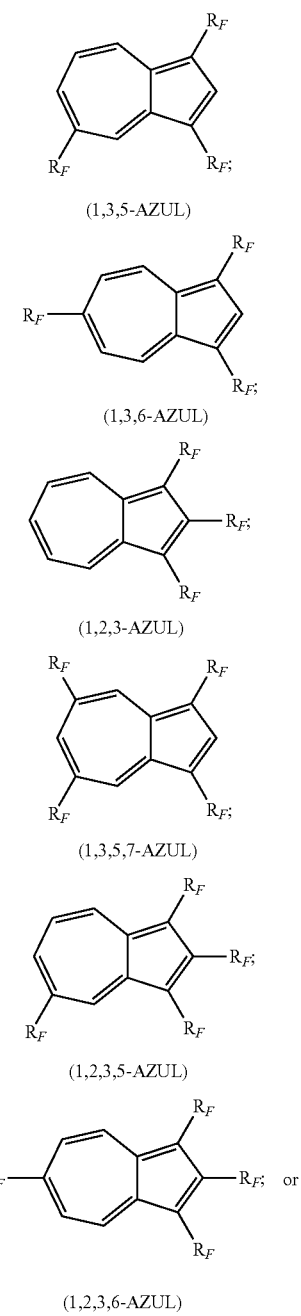

-continued
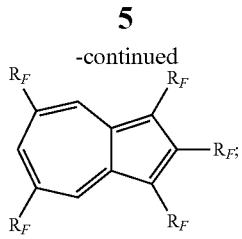
(1,2,3,5,7-AZUL)
wherein $R_F$ is $-(CF_2)_nCF_3$ wherein n is 0 to about 11.
In various other embodiments, the polyaromatic hydrocarbon having one or more perfluoroalkyl substituents formed is:
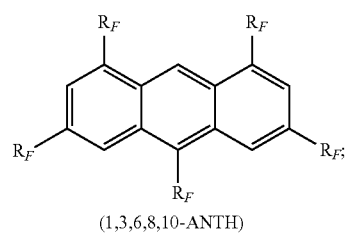
(1,3,6,8,10-ANTH)
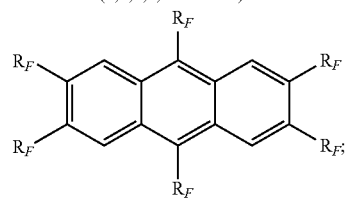
(2,3,6,7,9,10-ANTH)
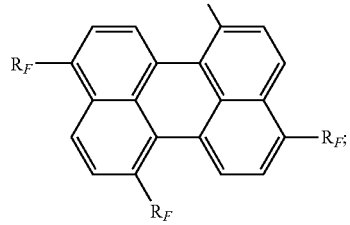
(1,4,7,10-PERY)
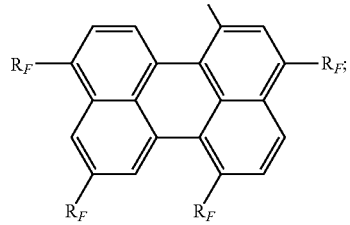
(1,3,6,8,10-PERY)
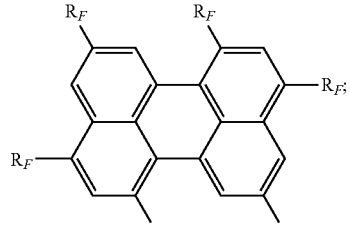
(1,3,5,7,9,11-PERY)
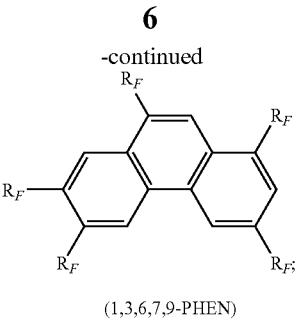
(1,3,6,7,9-PHEN)
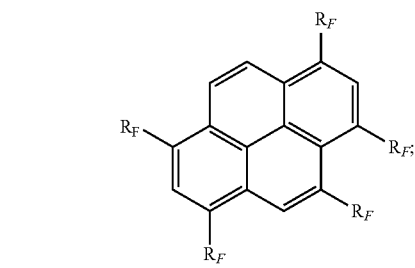
(1,3,4,6,8-PYRN)
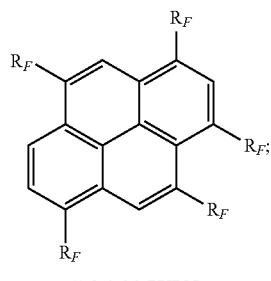
(1,3,4,6,9-PYRN)
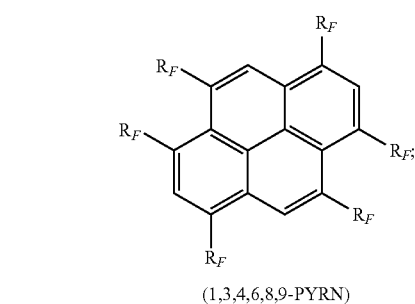
(1,3,4,6,8,9-PYRN)
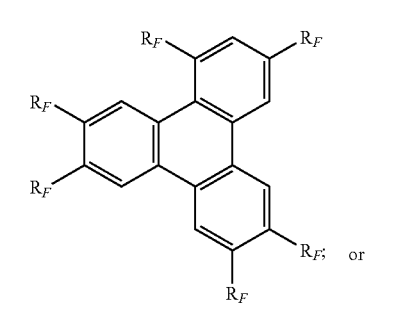
(1,3,6,7,10,11-TRPH); or

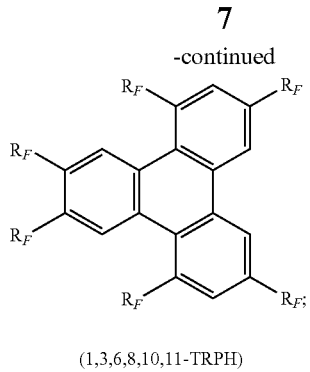

(1,3,6,8,10,11-TRPH)

wherein $R_F$ is —$(CF_2)_nCF_3$ wherein n is 0 to about 11.

In one embodiment, the polyaromatic hydrocarbon having one or more perfluoroalkyl substituents formed is a compound of Formula (III):

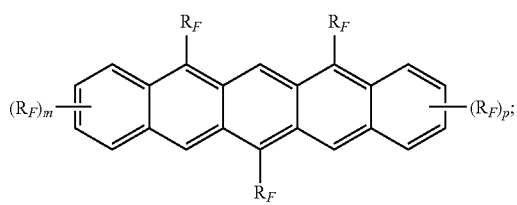
(III)

a compound of Formula (IV):

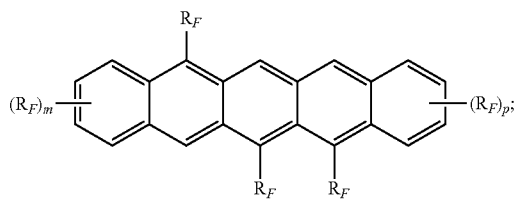
(IV)

a compound of Formula (V):

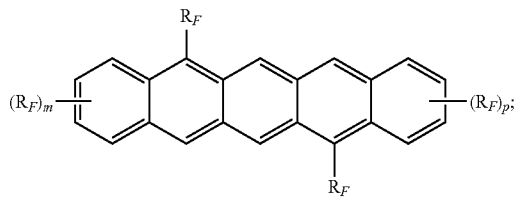
(V)

a compound of Formula (VI):

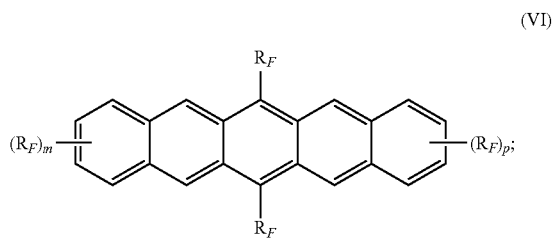
(VI)

or
a compound of Formula (VII):

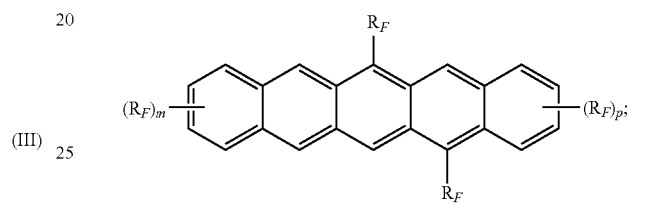
(VII)

wherein
  $R_F$ is —$(CF_2)_nCF_3$ wherein n is 0 to about 11;
  m is 0 to 3;
  p is 0 to 3; and
wherein the sum of m and p is 2, 3, 4, 5, or 6.

In another embodiment, the polyheterocyclic compound having one or more perfluoroalkyl substituents formed is a compound of Formula (X):

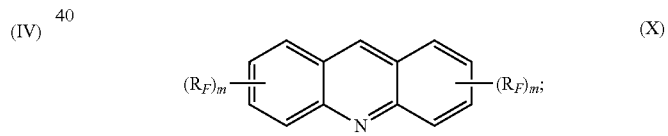
(X)

a compound of Formula (XI):

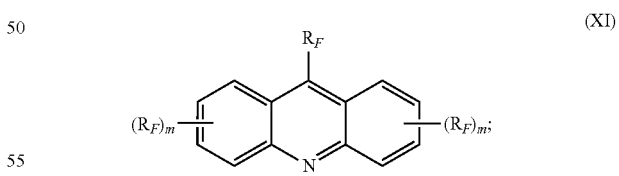
(XI)

a compound of Formula (XII):

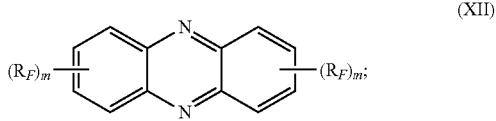
(XII)

a compound of Formula (XIII):

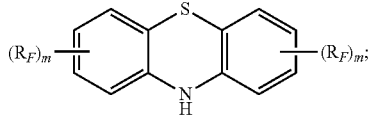

a compound of Formula (XIV):

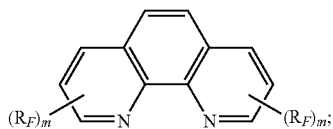

or
a compound of Formula (XV):

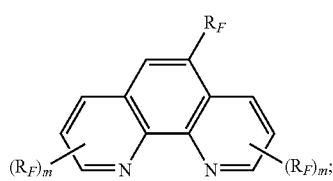

wherein
each $R_F$ is independently —$(CF_2)_nCF_3$ wherein n is 0 to about 11;
each m is independently 0 to 3; and
wherein the sum of elements m is 1, 2, 3, 4, or 5.

The invention further provides novel compounds one or more perfluoroalkyl groups. The compounds can include a polyaromatic hydrocarbon core, or a polyheterocyclic core. In some embodiments, the invention provides a compound prepared by a method described above. In certain embodiments, the compound having one or more perfluoroalkyl groups is a compound illustrated in FIG. 1, FIG. 9, FIG. 13, or FIG. 21, or described or illustrated herein.

When $R_F$ can be —$(CF_2)_nCF_3$ where n is 0 to about 11, compounds that include substituents having an n value of 0, 1, 2, 3, 4, 5, 6, 7, 8, 9, 10, or 11 can readily be prepared by employing the appropriate starting material perfluoroalkyl iodide.

When a compound is described as having one or more perfluoroalkyl groups, the compound can have as many perfluoroalkyl groups as there are available $sp^2$-hydribized C—H bonds in the substrate. However, typically fewer than the maximum number of substitutions are achieve. In some embodiments, one or more perfluoroalkyl groups refers to 2 to about 8 perfluoroalkyl groups, or two, three, four, five, six, seven, or eight perfluoroalkyl groups.

The methods described herein are general for a wide range of polyaromatic hydrocarbons and polyheterocyclic compounds. Thus, the invention provides a polyaromatic hydrocarbon or a polyheterocyclic compound having one or more perfluoroalkyl groups, where a formula can be illustrated as the substrate with a —$(R_F)_m$ group on any of the aryl rings of the compound, wherein m is 0-3. The sum of m groups for any particular compound can be 2, 3, 4, 5, 6, 7, 8, 9, or about 10, depending on the number of aromatic rings in the compound. Accordingly, the invention provides formulas of each polyaromatic hydrocarbon and polyheterocyclic compound described herein (e.g., Formula ($X^N$ wherein N is different for each substrate and product) substituted by one or more —$(R_F)_m$ groups. In some embodiments, even non-$sp^2$-hydribized C—H moieties can be substituted by using the methods described herein. In various embodiments, a group of compounds, or a group of compounds prepared by the methods described herein, exclude a compound substituted at the polyaromatic hydrocarbon or polyheterocyclic compound 1-, 2-, 3-, 4-, 5-, 6-, 7-, 8-, 9-, 10-, 11-, or 12-position, or a combination thereof, from the embodiment.

The invention thus provides novel compounds of the formulas described herein, as well as methods of preparing the compounds. The compounds are useful as intermediates for the synthesis of other useful compounds, and the compounds can be used as organic semiconductors in electronic devices.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
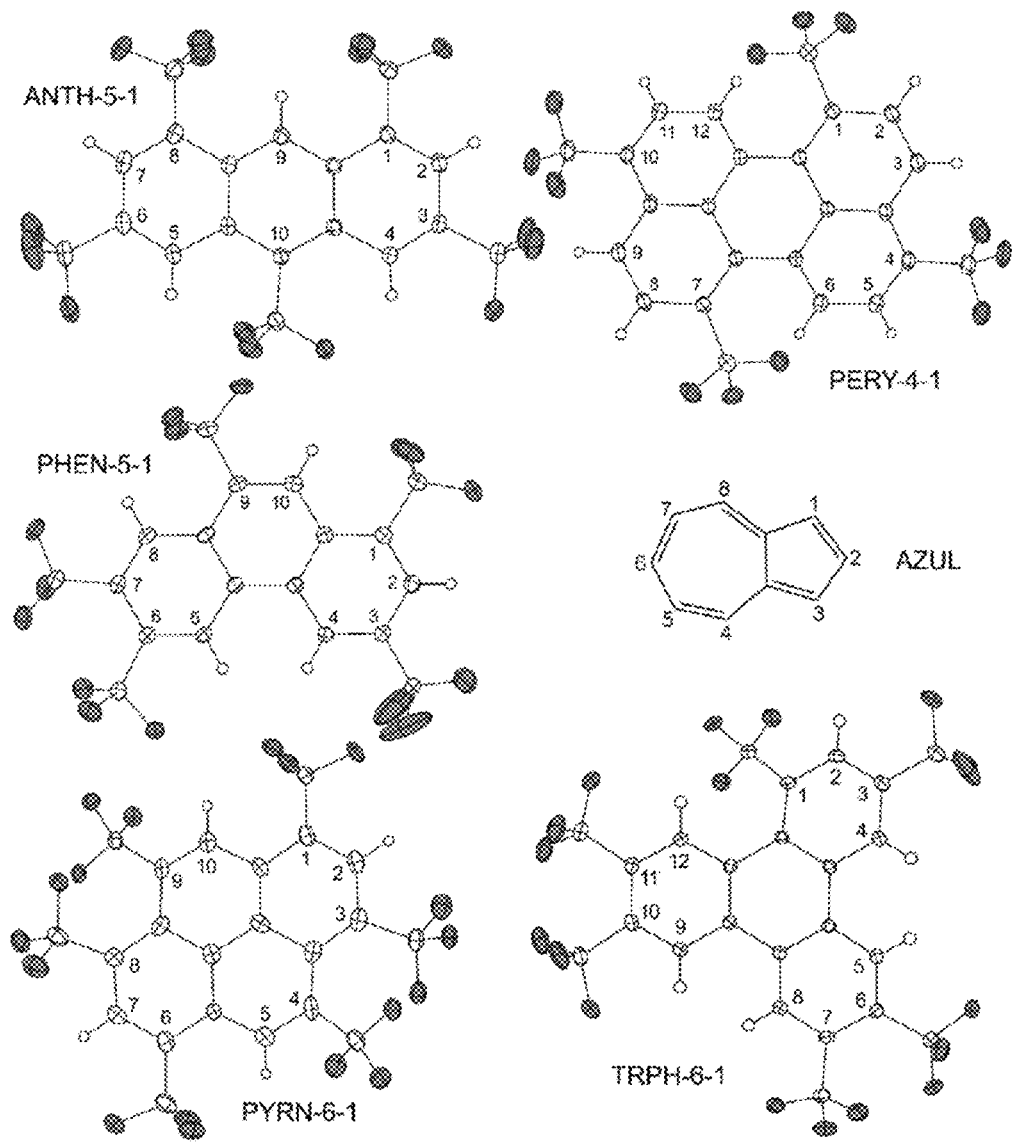
FIG. 1. Single-crystal X-ray diffraction thermal-ellipsoid plots of five compounds listed in Table 1 showing IUPAC locants (50% probability ellipsoids except for H atoms, which are spheres of arbitrary size; F atoms are dark spheres). Also shown are IUPAC locants for azulene (AZUL). The other abbreviations are defined in Table 1.

Currently there are only two reported methods for perfluoroalkylation of polyaromatic hydrocarbons (PAHs). The first method is based on substitution of bromine for a CF$_3$ group in the presence of CuI and CF$_3$COOH in solution (see for example: *Org. Lett.* 2009, 11, 2808). The second method uses a reaction of R$_F$I precursors with PAHs (R$_F$ group substitutes a hydrogen atom, see *Org. Lett.* 2010, 12, 2374) or with brominated PAHs (R$_F$ group substitutes a bromine atom, see *J. Org. Chem.* 2010, 75, 3007). Both methods are not well suited for a preparation of PAHs carrying a large number of R$_F$ groups in one selective step. The method described herein is well-suited for such applications because PAHs can be perfluoroalkylated directly (without the need to prepare and isolate brominated PAHs precursors) and without use of solvents. The method is solvent-free and therefore very environmentally friendly. Additionally, the specialized fullerene HPLC column Cosmosil Buckyprep can be used for the analysis and separation of mixtures of derivatized PAH compounds, which allows for the isolation of many different poly(perfluoroalkylated) PAH compounds, as described herein with poly(trifluoromethylated) corannulene, pentacene and perylene derivatives.

The invention thus provides a new method for the preparation of novel perfluoroalkylated polyaromatic hydrocarbons (PAH) and new compositions of matter, including C$_{20}$H$_{12-n}$(CF$_3$)$_n$, C$_{20}$H$_{10-n}$(CF$_3$)$_n$ and C$_{22}$H$_{14-n}$(CF$_3$)$_n$ compounds. The method is based on a direct reaction between perfluoroalkyl iodides (RFI) and PAH in gas phase at high temperature. A symmetric derivative of corannulene C$_{20}$H$_5$(CF$_3$)$_5$ can be prepared with high selectivity using this technique. This compound displays a blue fluorescence and a cathodic shift of about 1 V of its reversible first reduction potential relative to underivatized C$_{20}$H$_{10}$. Such compounds are useful for new photoelectrochemical devices such as OLEDs. The new synthetic methodology has been easily adapted to other promising PAHs such as pentacene and perylene for the modification of their physical and electrochemical properties. The high-temperature method ensures that only the most thermodynamically stable isomers of poly (perfluoroalkyl)PAHs are produced in abundance, thus leading to high selectivity.

Breakthroughs in molecular optoelectronics await the availability of new families of air-stable polyaromatic hydrocarbon (PAH) acceptors with incrementally- and predictably-tunable electron affinities and structures capable of inducing desirable solid-state morphologies in hybrid materials. Although the addition of electron withdrawing groups to PAHs has been studied for decades, producing new compounds from time to time, a generic one-step synthetic methodology applicable to potentially all PAH substrates has been, until now, unavailable.

A variety of substrates, including seventeen common PAHs and polyheterocyclics, can be trifluoromethylated by the new procedure to yield families of PAH(CF$_3$)$_n$ acceptors with (i) n=1-8, (ii) multiple isomers for particular n values, (iii) gas-phase experimental electron affinities as high as 3.32 eV and shifted from the respective PAH precursor as a linear function of n, and (iv) various solid-state morphologies, including the ability to form alternating π stacked hybrid crystals with aromatic donors. Furthermore, six new poly (trifluoromethyl)azulenes prepared in a single high-temperature reaction exhibit strong electron accepting properties in the gas phase and in solution and demonstrate propensity to form regular π-stacked columns in the donor-acceptor crystals, when mixed with pyrene as a donor. The methods thus provide robust, finely-tuned materials for new molecular optoelectronics, pharmaceuticals and agrochemicals, fluoropolymers, and catalysts

DEFINITIONS

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution or in a reaction mixture, including in the gas phase.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect, and for substitution, an effective amount is typically at least one molar equivalent, but can be as high as hundreds of equivalents, depending on the desired outcome of a reaction.

A "polyaromatic hydrocarbon" refers to a hydrocarbon having at least two rings, at least one of which is aromatic. Polyaromatic hydrocarbon fall within the class of arene compounds. Examples of polyaromatic hydrocarbons include, but are not limited to, acenaphthene, acenaphthylene, anthanthrene, anthracene, azulene, benzo[a]anthracene, benzo[a]fluorine, benzo[c]phenanthrene, benzopyrene, benzo[a]pyrene, benzo[e]pyrene, benzo[b]fluoranthene, benzo[j]fluoranthene, benzo[k]fluoranthene, benzo[ghi]perylene, chrysene, corannulene, coronene, dicoronylene, diindenoperylene, fluorene, fluoranthene, fullerene, helicene, heptacene, hexacene, indene, kekulene, naphthalene, ovalene, pentacene, perylene, phenalene, phenanthrene, dihydrophenanthrene, picene, pyrene, tetracene, and triphenylene.

As used herein, a "polyheterocyclic compound" refers to a heterocyclic compound having at least two rings, at least one of which is aromatic. Polyheterocyclic compound can also be referred to as heteroaromatic compounds. As used herein, a heterocyclic compound is cyclic aromatic compound that includes at least one heteroatom in an aromatic ring. Typical heteroatoms include oxygen, nitrogen, and sulfur. Examples of polyheterocyclic compounds include, but are not limited to, acridine, benzimidazole, 2H-1-benzothine, benzthiazole, benzo[b]furan, benzo[b]thiophene, benzo[c]thiophene, carbazole, cinnoline, dibenzothiophene, iminodibenzyl, 1H-indazole, indole, indolizine, isoindole, isoquinoline, 1,5-naphthyridine, 1,8-naphthyridine, phenanthridine phenanthroline, phenazine, phenoxazine, phenothiazine, phthalazine, quinazoline, quinoline, 4H-quinolizine, thianthrene, and xanthene.

A perfluoroalkyl iodide refers to a perfluorinated alkyl iodide such as a compound of Formula $IR_F$: I—$(CF_2)_nCF_3$; where n is 0 to about 11. Perfluoroalkyl iodides can be used to provide perfluoroalkyl substituents on polyaromatic hydrocarbons and polyheterocyclic compounds. Examples of perfluoroalkyl substituents include moieties of Formula $R_F$: —$(CF_2)_nCF_3$; where n is 0 to about 11. A perfluoroalkyl substituent can also be a branched perfluoroalkyl group such as the Krytox group: —$CF_2CF(-CF_3)(OCF_2CF(-CF_3))_gF$ where g is 0, 1, 2, 3, 4, 5, or 6.

The following abbreviations may be used for reference to certain polyaromatic hydrocarbons and polyheterocyclic compounds: acridine (ACRD); anthraquinone (ANTQ); phenothiazine (PHTZ); phenanthridine (PHTD); phenanthroline (PHTL); tetracyanoquinodimethane (TCNQ); and indole (INDL).

Polyarene Acceptors for Air-Stable Molecular Optoelectronics

A generic, one-step, solvent-, catalyst-, and promoter-free perfluoroalkylation methodology was developed for the preparation of strong $PAH(CF_3)_n$ electron acceptors that is potentially applicable to any commercially-available and thermally-stable PAH precursor. The methodology involves an elevated-temperature "one-pot" reaction between the PAH precursor and gaseous $CF_3I$ or related iodides in which single or multiple $CF_3$ groups can be added to the PAH core by replacing H atoms. Single reactions with 17 different precursors have provided up to four $PAH(CF_3)_n$ compositions as predominant products, in some cases with up to four isomers of particular compositions.

The method appears to be truly generic. $PAH(CF_3)_n$ compounds for seven PAHs, ANTH, AZUL, PENT, PERY, PHEN, PYRN, and TRPH have been prepared, isolated in pure form as single isomers and studied (see Table 1 for abbreviations). Preliminary results indicate that the method also works for fluorene, fluoranthene, naphthalene, and tetracene as well as for PAHs containing heteroatoms, such as phenazine, phenanthroline, phenothiazine, and iminodibenzyl. The reaction mechanism likely involves the formation of "hot" $CF_3$ radicals by thermally-induced dissociation of $CF_3I$, removal of a PAH H atom by a $CF_3$ radical to form $CHF_3$ and a PAH radical, and subsequent reaction of another $CF_3$ radical with the transient PAH radical to form the new PAH—$CF_3$ bond. This sequence would occur n times for a given $PAH(CF_3)_n$ derivative. In one reaction, $CHF_3$ was positively identified as one of the products along with 12 and the $PAH(CF_3)_n$ derivatives. Numbering schemes for six PAHs are shown in FIG. 1. Also shown are five of the seven X-ray structures that have been deposited with the Cambridge Crystallographic Data Centre.

With one exception, we have not yet endeavored to optimize reaction conditions as far as overall yield or product selectivity is concerned. Instead, two goals included (i) to demonstrate that families of $PAH(CF_3)_n$ derivatives in pure form as single isomers could be readily prepared in a single reaction from a variety of parent PAHs and (ii) to examine the electronic properties and solid-state morphologies of as many of the new compounds as possible. Therefore, most reactions were carried out using only 0.10-0.12 mmol portions of the PAH precursor (Table 2). The one exception is a series of reactions starting with 1.0 mmol (178 mg) portions of ANTH that were shown to produce, predominantly and nearly quantitatively, $ANTH(CF_3)$4,5,6 mixtures. Isolated yields of two of the HPLC-purified products were 5 mol % for 95+% pure ANTH-5-1 and 20 mol % for 98+% pure ANTH-6-1 (based on ANTH).

Table 1 lists EAs and $E_{1/2}$ values for the new $PAH(CF_3)_n$ compounds. The former were determined by low-temperature photoelectron spectroscopy and the latter by CV. Also listed are the NIST-WebBook EAs of the parent PAHs and their $E_{1/2}$ values; the latter were determined in this work using the same apparatus, electrodes, electrolyte, and conditions used for the $PAH(CF_3)_n$ compounds.

TABLE 1

Experimental Results and Abbreviations for PAH and $PAH(CF_3)_n$ Compounds[a]

| Compound | purity, mol %[b] | isolated yield, mol % | abbrev. | gas-phase EA,[c] eV | $E_{1/2}$,[e] V vs. $Fe(Cp)_2^{+/0}$ | X-ray structure[h] |
|---|---|---|---|---|---|---|
| Anthracene | 99 | — | ANTH | 0.53(2)[c] | −2.52 | — |
| 1,3,6,8,10-$ANTH(CF_3)_5$ | 95 | 5 | ANTH-5-1 | 2.40(2) | −1.24 | Yes |
| 2,3,6,7,9,10-$ANTH(CF_3)_6$ | 98 | 20 | ANTH-6-1 | 2.81(2) | −0.92 | Yes |
| Azulene | 99 | — | AZUL | 0.790(8)[d] | −2.14 | — |
| 1,2,3,5,7-$AZUL(CF_3)_5$ | 98 | 25 | AZUL-5-1 | 2.890(5) | −0.73 | prelim. |
| Naphthalene | 99 | — | NAPH | −0.2[d] | −3.09 | — |
| Pentacene | 99 | — | PENT | 1.39(4)[d] | —[f] | — |
| $PENT(CF_3)_8$ | mixture of isomers | <2 | | 3.32(2) | —[g] | no |
| Perylene | 99 | — | PERY | 0.973(5)[d] | −2.23 | — |
| 1,4,7,10-$PERY(CF_3)_4$ | 98 | <3 | PERY-4-1 | 2.20(2) | −1.30 | Yes |
| 1,3,6,8,10-$PERY(CF_3)_5$ | 98 | <3 | PERY-5-1 | 2.46(2) | −1.19 | Yes |
| $PERY(CF_3)_5$ | 95 | <3 | PERY-5-2 | 2.48(2) | −1.29 | no |

TABLE 1-continued

Experimental Results and Abbreviations for PAH and PAH(CF$_3$)$_n$ Compounds[a]

| Compound | purity, mol %[b] | isolated yield, mol % | abbrev. | gas-phase EA,[c] eV | $E_{1/2}$,[e] V vs. Fe(Cp)$_2$[+/0] | X-ray structure[h] |
|---|---|---|---|---|---|---|
| PERY(CF$_3$)$_5$ | 95 | <3 | PERY-5-3 | 2.49(2) | −1.22 | no |
| PERY(CF$_3$)$_5$ | 90 | <3 | PERY-5-4 | 2.45(2) | −1.15 | no |
| 1,3,5,7,9,11-PERY(CF$_3$)$_6$ | 97 | <3 | PERY-6-1 | 2.72(2) | −1.01 | prelim. |
| PERY(CF$_3$)$_7$ | mixture of isomers | <2 | | 2.91(2) | —[g] | no |
| phenanthrene | 98 | — | PHEN | 0.04[d] | −3.10 | — |
| 1,3,6,7,9-PHEN(CF$_3$)$_5$ | 95 | <5 | PHEN-5-1 | 1.95(1) | −1.71 | yes |
| Pyrene | 98 | — | PYRN | 0.41(1)[d] | −2.65 | — |
| 1,3,4,6,8-PYRN(CF$_3$)$_5$ | 95 | <3 | PYRN-5-1 | 2.44(2) | −1.25 | yes |
| 1,3,4,6,9-PYRN(CF$_3$)$_5$ | 70 | <3 | PYRN-5-2 | 2.38(2) | −1.27 | prelim. |
| 1,3,4,6,8,9-PYRN(CF$_3$)$_6$ | 95 | <3 | PYRN-6-1 | 2.71(2) | −1.01 | yes |
| triphenylene | 98 | — | TRPH | 0.285(8)[d] | −3.01 | — |
| 1,3,6,7,10,11-TRPH(CF$_3$)$_6$ | 98 | 25 | TRPH-6-1 | 2.11(2) | −1.73 | yes |

[a]All data from this work unless otherwise noted.
Anthracene (ANTH) = C$_{14}$H$_{10}$;
azulene (AZUL) = C$_{10}$H$_8$;
naphthalene (NAPH) = C$_{10}$H$_8$;
pentacene (PENT) = C$_{22}$H$_{14}$;
perylene (PERY) = C$_{20}$H$_{12}$;
phenanthrene (PHEN) = C$_{14}$H$_{10}$;
pyrene (PYRN) = C$_{16}$H$_{10}$;
triphenylene (TRPH) = C$_{18}$H$_{12}$.
Note that the generic abbreviation PAH(CF$_3$)$_n$ denotes a compound with $n$ H atoms replaced by $n$ CF$_3$ groups (e.g., the composition of ANTH(CF$_3$)$_6$ is C$_{14}$H$_4$(CF$_3$)$_6$, not C$_{14}$H$_{10}$(CF$_3$)$_6$).
[b]The purity was determined based on the $^1$H and $^{19}$F NMR spectroscopy, NI-APCI mass spectrometry, and HPLC analysis, see Example 1 below. For commercial samples of starting materials the purity is reported as given by vendor.
[c]EA = electron affinity; uncertainty in the least significant digit shown in parentheses.
[d]Values taken from NIST WebBook.
[e]Cyclic voltammetry (CV); anaerobic; 0.1M N(n-Bu)$_4$ClO$_4$ in dimethoxyethane; platinum working and counter electrodes; silver wire quasi-reference electrode; 500 mV s$^{-1}$; ferrocene (Fe(Cp)$_2$) and decamethylferrocene internal standards.
[f]Insufficiently soluble in DME for CV.
[g]Mixture of isomers; not measured.
[h]The designation "yes" indicates that a crystallographic information (CIF) file has been deposited with the Cambridge Structural Database. The designation "prelim." indicates that a preliminary X-ray structure has been determined and that the addition pattern and solid-state packing are known but higher-quality data sets will be recorded before CIF files are deposited.

TABLE 2

Reaction conditions used for trifluoromethylation of PAH substrates.

| PAH substrate | m(PAH), mg | n(CF$_3$I) | V$_{ampoule}$, mL | V$_{headspace}$, mL | T, °C | reaction time, h |
|---|---|---|---|---|---|---|
| ANTH | 178 | 12 | 250 | 250 | 360 | 24 |
| AZUL | 13 | 20 | 50 | 50 | 360 | 0.5 |
| PENT | 28 | 36 | 50 | 50 | 360 | 18 |
| PERY | 25 | 36 | 50 | 50 | 360 | 24 |
| PHEN | 18 | 20 | 50 | 50 | 360 | 24 |
| PYRN | 20 | 30 | 50 | 50 | 360 | 24 |
| TRPH | 23 | 30 | 50 | 50 | 360 | 24 |
| TETR | 194 | 12 | 314 | 314 | 360 | 7 |
| ACRD | 179 | 9 | 268 | 268 | 330 | 9 |
| TRPH | 228 | 6 | 50 | 50 | 300 | 4 |
| ANTQ | 25 | 10 | 40 | 40 | 300 | 4 |
| PHNZ | 216 | 10 | 373 | 373 | 330 | 20 |
| PHTZ | 200 | 10 | 363 | 363 | 330 | 7 |
| PHTD | 193 | 10 | 330 | 330 | 328 | 6 |
| PHTL | 251 | 10 | 390 | 390 | 330 | 14 |
| TCNQ | 242 | 8 | 290 | 290 | 310 | 6 |
| INDL | 177 | 6 | 280 | 280 | 320 | 8 |

Figure 2:
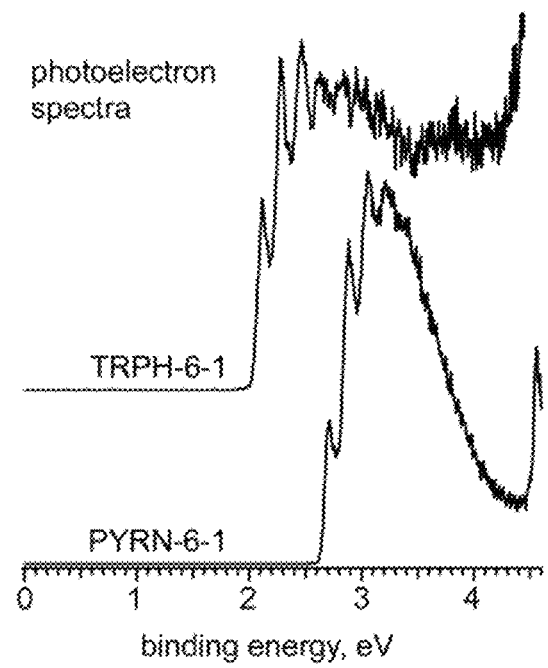
FIG. 2. Negative-ion photoelectron spectra (12 K, 266 nm) of representative PAH(CF$_3$)$_n$ compounds.
Figure 3:
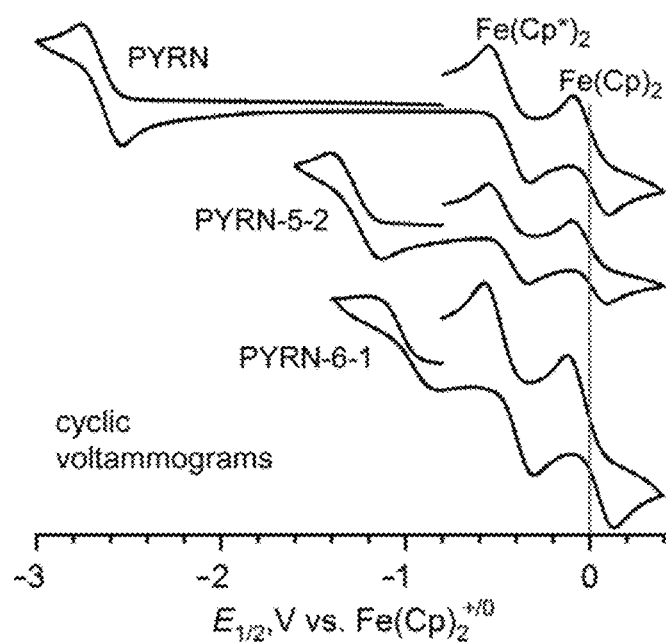
FIG. 3. Cyclic voltammograms (0.1 M N(n-Bu)$_4$ClO$_4$ in dimethoxyethane, 500 mV s$^{-1}$) of representative PAH(CF$_3$)$_n$ compounds.

Representative photoelectron spectra and CVs are shown in FIG. 2 and FIG. 3. The PAH(CF$_3$)$_n$ EAs range from 1.95(1) eV for PHEN-5-1 to 3.32(2) eV for the mixture of PENT(CF$_3$)$_8$ isomers. In contrast, the highest EA for the eight parent PAHs in Table 1 is 1.39(4) eV for PENT; all others are <1 eV. The $E_{1/2}$ values range from −1.73(2) V vs. Fe(Cp)$_2$$^{+/0}$ for TRPH-6-1 to −0.73(2) V for AZUL-5-1 and, in contrast, the least negative PAH $E_{1/2}$ value is −2.14(2) V for AZUL; the others range from −2.23(2) V for PERY to less than (i.e., more negative than) −3 V for NAPH, PHEN, and TRPH.

Figure 5:
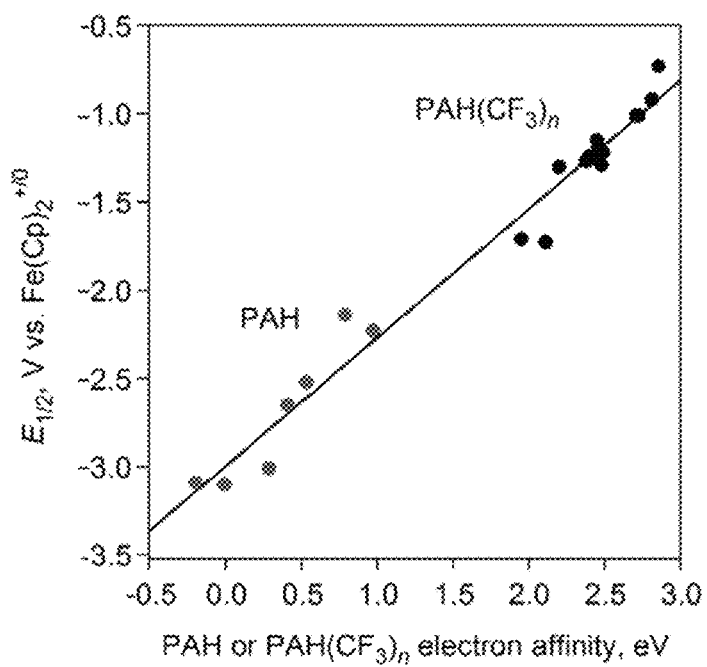
FIG. 5. Plot of $E_{1/2}$ vs. gas-phase EA for PAH and PAH (CF$_3$)$_n$ compounds. The slope of the least-squares fit to the data is 0.73 V eV$^{-1}$. The experimental uncertainties for the PAH(CF$_3$)$_n$ compounds (≤0.02 V or 0.02 eV) are smaller than the width of the data points.

A plot of $E_{1/2}$ vs. EA for all but three of the entries in Table 1 is shown in FIG. 5. The plot is nominally linear with a slope of 0.73 V eV$^{-1}$. This demonstrates, for a broad set of PAHs and PAH(CF$_3$)$_n$ derivatives, that the incremental change in $E_{1/2}$ from one compound to the next is, on average, attenuated by 27% relative to the change in EA from one compound to the next. Designers of new electron acceptors with targeted EAs will find this correlation useful, because reduction potentials are much easier to measure than precise values of gas-phase electron affinities. Significantly, the 0.73 V eV$^{-1}$ slope stands in contrast to the 1.0 V eV$^{-1}$ slope for a similar plot for aromatic hydrocarbons published by Ruoff et al. in 1994 (*J. Phys. Chem.* 1995, 99, 8843-8850) (i.e., a 1:1 correlation between $E_{1/2}$ and gas-phase EA for PAHs and PAH derivatives with multiple CF$_3$ groups was not confirmed in our work; the correlation observed is 0.73:1).

Figure 4:
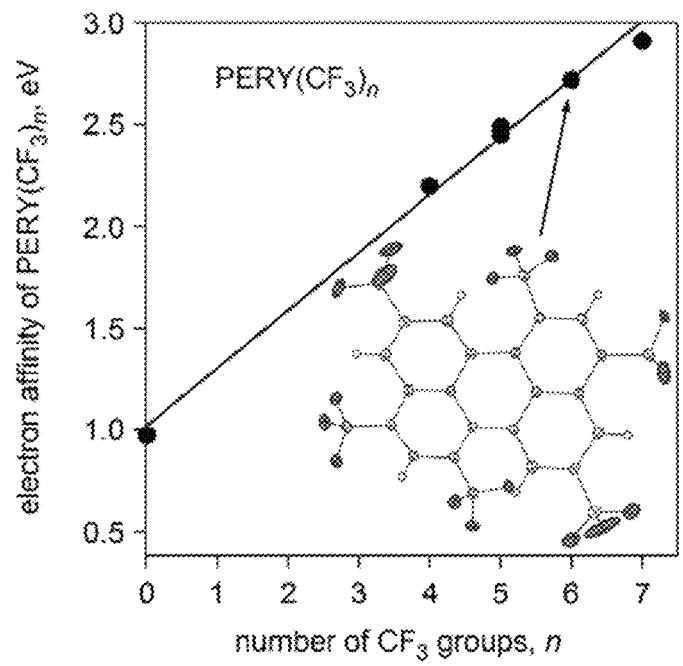
FIG. 4. Plot of PES-determined gas-phase EA of perylene (PERY; n=0) and PERY(CF$_3$)$_n$ compounds (n=4, 5, 6, 7) vs. n. The slope of the least-squares fit to the data is 0.28 eV per CF$_3$ group. The experimental uncertainties for the PAH(CF$_3$)$_n$ compounds (≤0.02 V or 0.02 eV) are smaller than the width of the data points.

Our EA results also demonstrate that there is a nearly-linear incremental, and therefore predictable, change in EA for each CF$_3$ added to PERY, ANTH, and PYRN. A plot of EA vs. the number of CF$_3$ groups is shown in FIG. 4 for PERY (CF$_3$)$_n$ derivatives (n=0, 4, 5 (four isomers), 6 and 7). The slope of this plot is 0.28 eV per CF$_3$ group. For ANTH(CF$_3$)$_n$ and PYRN(CF$_3$)$_n$, which have fewer C atoms than PERY (CF$_3$)$_n$, the slopes of the corresponding plots are 0.38 and 0.39 eV per CF$_3$, respectively (see Example 1). The slope for the ANTH(CF$_3$)$_n$ plot of our data is similar to the DFT-predicted slope of 0.35 eV per CF$_3$ recently reported by Sun et al. (*J. Phys. Chem. A* 2012, 116, 8015-8022). In that work, the hypothetical isomer chosen for ANTH(CF$_3$)$_6$ is coincidentally the same as our new compound ANTH-6-1 (there is also good agreement between Sun's DFT-predicted EA for this compound, 2.73 eV, and the experimental value reported here, 2.81(2) eV). Note that the first prediction of a linear plot of DFT-predicted EA vs. number of CF$_3$ groups was for $C_{20}H_{10-n}(CF_3)_n$ derivatives ($C_{20}H_{10}$=corannulene; the reported slope is 0.20 eV per CF$_3$).

Figure 6:
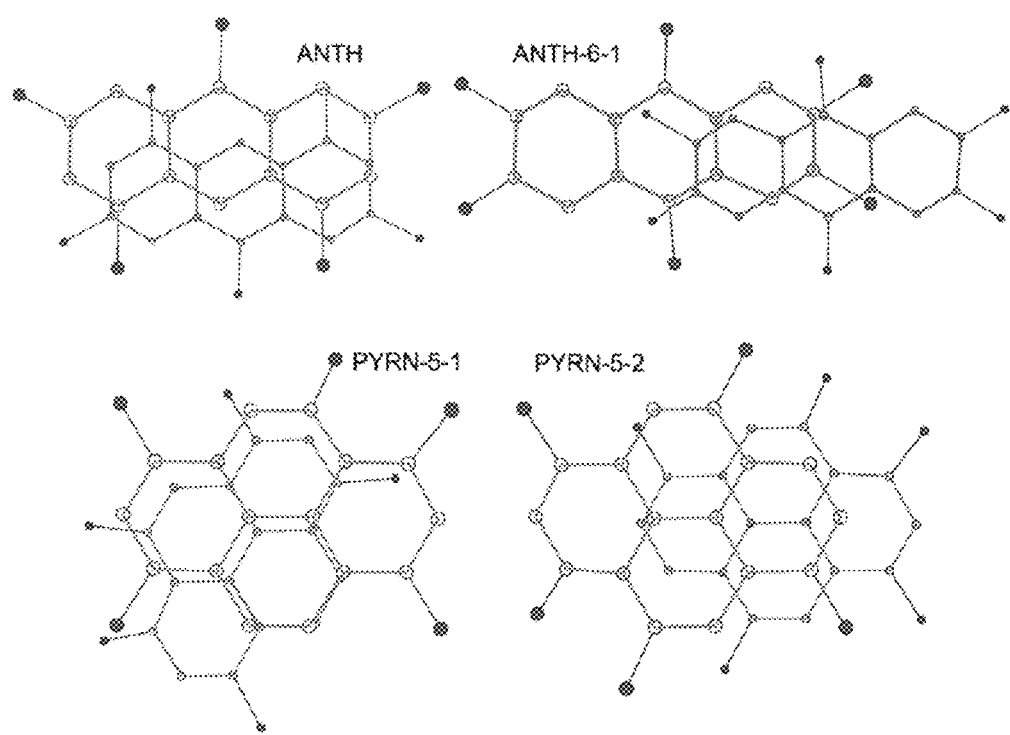
FIG. 6. Comparison of portions of the X-ray structures of ANTH-5-1 and ANTH-6-1 (top) and PYRN-5-1 and PYRN-5-2 (bottom). Both F and H atoms have been omitted for clarity, and the C atoms are shown as spheres of arbitrary size. The CF$_3$C atoms are shaded gray. Each drawing is oriented so that the least-squares plane of the lower aromatic core is in the plane of the page. For ANTH-5-1, ANTH-6-1, and PYRN-5-2, the least-squares planes of the upper aromatic cores are rigorously parallel to the planes of the lower cores. For PYRN-5-1, the least-squares plane of the upper aromatic core is tilted 5.2° with respect to the plane of the lower core.

The X-ray structures reported here reveal two interesting results potentially relevant to the use of PAH(CF$_3$)$_n$ derivatives for optoelectronic applications. The first feature is that the number of CF$_3$ groups attached to ANTH can significantly affect the extent to which neighboring molecules interact through their π clouds. A comparison of neighboring pairs of molecules of ANTH-5-1 and ANTH-6-1 is shown in FIG. 6. Note that the molecules are offset differently along both the long and short molecular axes (i.e., the pitch and roll angles, respectively, are different). The difference in slippage along the long axis, ca. 0.6 Å for ANTH-5-1 and ca. 4.0 Å for ANTH-6-1, is far greater than along the short axis. Note that the long axis of the aromatic core is 7.3 Å for ANTH, so the pitch distance in ANTH-6-1 is more than half a molecule.

The second structural feature is that the isomers PYRN-5-1 and PYRN-5-2, which have nearly identical EAs and $E_{1/2}$ values, and which have four of their five CF$_3$ groups in common positions, have very different relative orientations between neighboring molecules in their respective lattices, as shown in FIG. 6. This leads to significant differences in π-π stacking. In PYRN-5-1, the aromatic cores of neighboring molecules are essentially parallel but are rotated 45° with respect to one another, resulting in the near superposition of three rings in each molecule. In PYRN-5-2, on the other hand, the closest parallel neighboring aromatic cores are not rotated, have essentially zero roll distance, and have a pitch distance equivalent to one-half of the distance between para-C atoms on the hexagonal rings, resulting in a significantly offset stacking geometry.

Finally, we have measured the air stability in the presence of bright light and the fluorescence quantum yields for selected compounds (see Example 1). Taken together, the results described here demonstrate that our generic synthetic methodology, coupled with high-efficiency HPLC purification, can provide many dozens of new PAH(R$_F$)$_n$ compounds, many of which will be sublimable, freely soluble in a range of organic solvents, air-, light-, and thermally-stable, and powerful electron acceptors available for use in fundamental studies of the correlations between molecular composition/structure and physicochemical properties. When the syntheses are scaled up, the new compounds will be available for new generations of molecular transistors, photovoltaics, ferroelectrics, non-volatile memory, non-linear optics, fluorescent probes pharmaceuticals, agrochemicals, organometallic catalysts, and composite polymer/PAH blends.

General Method for Perfluoroalkylation of Polyaromatic Hydrocarbons and Polyheterocyclics A polyaromatic hydrocarbon (PAH) sample and an excess of CF$_3$I reagent is loaded into a glass ampoule and the ampoule is flame-sealed. The ampoule can be heated in a tube furnace to about 300-450° C. and then be allowed to cool. Typically, ampoules are allowed to slowly cool to room temperature in open air, although other embodiments may also utilize standard techniques to accelerate the cooling process. Large-volume Pyrex glass ampoules may be used as reactor vessels; volumes are limited mostly by the size of the heating oven available. The ampoules can be charged with solid PAH starting materials and R$_F$I reagent and flame-sealed under vacuum. The ampoules can be equipped with a relatively small test-tube-like tip for R$_F$I reagent freezing using liquid nitrogen. The quantities of the reagents can be limited to about 80-100 mmol of RFI reagent per one liter of ampoule volume to limit the internal pressure to about 1,500 torr at the reaction temperature (300-450° C., typically about 360° C.). This translates into about 0.01 mole of starting PAH material per one liter of ampoule volume (producing up to several grams of crude PAH(R$_F$)$_n$ product per run per one liter of ampoule volume). After heating for 1-24 hours, the ampoule is cooled down and opened by cutting the sealed glass tip. The products are dissolved in dichloromethane and worked up using standard techniques. After a wash, the ampoule can be outfitted with a new seal-off neck and a Teflon glass valve and reused.

The reaction temperature and pressure may be varied. The perfluoroalkylation reaction described herein may be conducted in the temperature range between about 200 and about 450° C. It is possible that lower temperatures may be used (for example, in the presence of a reaction promoters such as copper) for preparation of thermally unstable compounds; higher temperatures (up to 800° C. or 1000° C.) may be used for preparation of highly perfluoroalkylated products and/or for tandem perfluoroalkylation/geodesic PAH synthesis. The pressure of the reaction may also be varied. In the certain embodiments described herein, the internal pressure was limited to about 1,500 torr due to the safety requirements of the equipment available to the inventors. It should be understood that much higher pressures (tens of bars and potentially higher) may be of high value for economical large-scale product preparation (for example, due to reactor volume decrease and possible yield improvements).

The PAH can be replaced with polyheterocyclic compounds, and other perfluoroalkyl iodides can be used in place of CF$_3$I. Those skilled in the art will readily recognize that the scale of the reaction can be increased in a straightforward way, without deviating from the essence of the method described herein. Furthermore, other methods of achieving the required temperature and pressure will be recognized as wholly consistent with this method.

The methods described herein can be used to prepare both known compounds and novel compounds. Examples of known compounds that can be prepared using the methods described herein include the perfluoroalkyl substituted polyaromatic hydrocarbons and polyheterocyclic compounds described in US Patent Publication No. 2012/0208989 (Sun et al.).

Uses of Polyaromatic Hydrocarbons and Polyheterocyclic Compounds Having Perfluorinated Substituents.

The perfluoroalkylated aromatic compounds described herein offer many advantages over non-fluorinated materials in a variety of different optoelectronic devices such as, but not limited to, organic light emitting diodes, organic field-effect transistors, organic photovoltaics, organic solar cells, and dye-sensitized solar cells. The fluorinated compounds have processing advantages and are thermally and photochemically stable. The fluorinated compounds also have advantages in tuning the electronic and optical properties of electronic devices. The compounds described herein can be used to produce oxygen stable n-type semiconductors. For example, azulene's unique properties have uses in molecular switches, molecular diodes, organic photovoltaics, and charge transfer complexes. Introduction of electron-withdrawing groups to the azulenic core, such as CN, halogens, and CF3, can enhance certain electrical and photophysical properties. The perfluoroalkylated cores of other compounds can be similarly useful. The compounds can be used in devices such as those described in US Patent Publication No. 2012/0208989 (Sun et al.).

Sources of Polyaromatic Hydrocarbons and Polyheterocyclic Compound Substrates

Commercially available polyaromatic hydrocarbon substrates, polyheterocyclic compound substrates, and perfluoroalkyl iodides may be obtained from standard commercial sources including Acros Organics (Pittsburgh, Pa.), Aldrich Chemical (Milwaukee, Wis., including Sigma Chemical and Fluka), Eastman Organic Chemicals, Eastman Kodak Company (Rochester, N.Y.), Fisher Scientific Co. (Pittsburgh, Pa.), ICN Biomedicals, Inc. (Costa Mesa, Calif.), Lancaster Synthesis (Windham, N.H.), Spectrum Quality Product, Inc. (New Brunswick, N.J.), TCI America (Portland, Oreg.), and Wako Chemicals USA, Inc. (Richmond, Va.).

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Trifluoromethylation of Polyaromatic Hydrocarbons

Simple and regioselective high-temperature, solvent-free, and catalyst-free reactions of various polyarenes with $CF_3I$ yielded new families of air-stable, robust, and soluble organic acceptors that exhibit significant and remarkably-regular incremental changes in gas-phase electron affinities as a function of the number of $CF_3$ groups and demonstrate a variety of crystalline morphologies with $\pi$-$\pi$ stacking.

Reagents and Solvents.

HPLC Grade acetonitrile (Fisher Scientific), trifluoromethyl iodide (Synquest Labs), and polycyclic aromatic hydrocarbons (Sigma Aldrich) were used as received.

Instruments.

HPLC analysis and separation was done using Shimadzu liquid chromatography instrument (CBM-20A control module, SPD-20A UV-detector set to 300 nm detection wavelength, LC-6AD pump, manual injector valve) equipped with semi-preparative 10-mm I.D.×250 mm Cosmosil Buckyprep column with a corresponding semi-preparative guard column (Nacalai Tesque, Inc.). The atmospheric-pressure chemical ionization (APCI) mass spectra were recorded on 2000 Finnigan LCQ-DUO mass-spectrometer ($CH_3CN$ carrier solvent, 0.3 mL·min$^{-1}$ flow rate, analyte samples injected as solutions in $CH_2Cl_2$). Proton and fluorine-19 NMR spectra were recorded on Varian INOVA 400 instrument in $CDCl_3$ solution. Cyclic voltammetry measurements were carried out on PAR 263 potentiostat/galvanostat.

NMR Spectra of Purified $PAH(CF_3)_n$ Compounds.

All NMR spectra were recorded with $CDCl_3$ solutions using a Varian 400-MR NMR spectrometer. The $^1H$ and $^{19}F$ frequencies were 400 and 376 MHz, respectively. The $^{19}F$ chemical shifts were determined using $1,4$-$C_6H_4(CF_3)_2$ as an internal standard ($\delta$ −66.35). The $^1H$ chemical shifts were determined using the resonance of the residual $CHCl_3$ in $CDCl_3$ as an internal standard ($\delta$ 7.27). The purity of the compounds was determined by examining the $^{19}F$ NMR spectra, which in general have very narrow resonances, and estimating the level of impurities from any observable low-intensity resonances near the baseline.

General Trifluoromethylation Procedure.

A sample of PAH was placed into a glass ampoule and the ampoule was evacuated using a vacuum line equipped with a pressure gauge and a calibrated volume. Using the calibrated volume and the pressure gauge, $CF_3I$ reagent was measured, then the ampoule was cooled with liquid nitrogen and the measured amount of $CF_3I$ reagent was condensed into it. Then the ampoule was flame-sealed. Caution was taken against ampoule explosion by calculating maximum pressure thresholds and using appropriate equipment; bench shields and personal protection were used. See Table 2 for specific experimental details; the individual yields of different isomers are given below in the descriptions of their purification.

Purification of ANTH-6-1 and ANTH-6-2.

The first stage of purification employed a semi-preparative Cosmosil Buckyprep HPLC column and an ACN eluent flow rate of 5.0 mL·min$^{-1}$. The fraction collected between 9.7 and 11.5 min contained 98+% pure ANTH-6-1 (the purity was calculated based on the $^1H$ and $^{19}F$ NMR data for all of the reported compounds), which was isolated in 20 mol % yield based on the amount of ANTH starting material. The fraction collected between 6.7 and 7.7 min contained impure ANTH-5-1, which was purified by a second stage of purification, which employed an analytical FluoroFlash column and an ACN eluent flow rate of 2.0 mL·min$^{-1}$. The fraction eluting between 4.9 and 6.3 min contained ca. 95+% pure ANTH-5-1, which was isolated in 5 mol % yield based on ANTH.

Purification of AZUL-5-1.

The crude product mixture was purified by HPLC using the semi-preparative Cosmosil Buckyprep column and an ACN eluent flow rate of 5.0 mL·min$^{-1}$ flow rate. The fraction collected between 4.7 and 5.6 min contained 98+% pure AZUL-5-1, which was isolated in 25 mol % yield based on the amount of AZUL starting material.

Purification of TRPH-6-1.

The crude product mixture was purified by HPLC using the Cosmosil Buckyprep column and an ACN eluent flow rate of 5.0 mL·min$^{-1}$ flow rate. The fraction collected between 20.7 and 22.7 min contained 98+% pure TRPH-6-1, which was isolated in 25 mol % yield based on the amount of TRPH starting material.

Separation of PERY(CF$_3$)$_n$ Compounds.

The first stage of HPLC purification employed the Cosmosil Buckyprep column and an ACN eluent flow rate 5.0 mL·min$^{-1}$. The fraction collected between 5.0 and 5.9 min contained impure PERY-6-1; the fraction collected between 6.9 and 8.0 min contained impure PERY-5-2; the fraction collected between 9.0 and 10.1 min contained impure PERY-4-1; the fraction collected between 10.1 and 11.3 min contained a mixture of PERY-5-3 and PERY-5-4; the fraction collected between 11.3 and 12.8 min contained impure PERY-5-1. Each of these fractions underwent a second-stage of purification using the FluoroFlash column with an ACN flow rate of 2.0 mL·min$^{-1}$. The amounts of purified compounds collected were too small for meaningful yields to be determined (but less than 5 mol %; see Table 1 for purity data).

Purification of PYRN(CF$_3$)$_n$ Compounds.

The first stage of HPLC purification employed the Cosmosil Buckyprep column and an ACN eluent flow rate 5.0 mL·min$^{-1}$. The fraction collected between 3.1 and 5.3 min contained impure PYRN-6-1; the fraction collected between 13.3 and 15.0 min contained ca. 95% pure PYRN-5-1; the fraction collected between 16.0 and 17.9 min contained a ca. 70:30 mixture of PYRN-5-2 and another isomer tentatively labeled PYRN-5-3. The PYRN-6-1 fraction underwent a second-stage of purification using the FluoroFlash column with an ACN flow rate of 2.0 mL·min$^{-1}$. The amounts of purified compounds collected, including ca. 95% pure PYRN-6-1, were too small for meaningful yields to be determined (but less than 5 mol %).

Purification of PHEN-5-1.

The crude product mixture was purified using the Cosmosil Buckyprep column and an ACN eluent flow rate of 5.0 mL·min$^{-1}$. The fraction collected between 9.9 and 10.5 min contained ca. 95% pure PHEN-5-1. The amount collected was too small to determine a meaningful yield (but less than 5 mol %).

Photostability Testing.

Equal 2.0 mL aliquots of 0.2 mM solutions of perylene and PERY-6-1 in CDCl$_3$ were put into glass scintillation vials under air, tightly capped, and irradiated with a 30 W halogen lamp (the vials were placed 10 cm away from the "naked" light bulb). After 30 min of the exposure HPLC analysis showed that perylene underwent a complete degradation turning into at least six different products (based on the HPLC analysis; no precipitate formation was observed). The solution of PERY-6-1 was unchanged even after three days of irradiation (based on HPLC analysis and $^{19}$F and $^1$H NMR spectrometry results).

Fluorescence Quantum Yields.

Fluorescence quantum yields were measured on an AVIV ATF-105 Auto-Titrating Differential/Ratio Spectrofluorimeter which has a 90° measurement geometry. The standard used was quinine sulfate in 0.105 M HClO$_4$ with a quantum yield of 0.60 (Velapoldi, R. A.; Mielenz, K. D. *NBS Special Publication* 260-64; National Bureau of Standards: Washington, D.C., 1980). PERY, PERY-4-1 and PERY-6-1 were separately dissolved in toluene and the absorbance was at or below 0.08 at wavelengths at and above the excitation wavelength. The calculated quantum yields are: PERY 0.58, PERY-4-1 0.52, PERY-6-1 0.27.

TABLE 1.1

PAH Product Data (results based on mass spectral analysis).

| PAH substrate[a] | maximum value of $n$ for PAH(CF$_3$)$_n$ products[b] | $n$ value(s) of predominant products[b] |
|---|---|---|
| ANTH | 7 | 5, 6 |
| AZUL | 5 | 5 |
| PENT | 8 | 6 |
| PERY | 7 | 4, 5, 6 |
| PHEN | 6 | 5 |
| PYRN | 7 | 5, 6 |
| TRPH | 7 | 6, 7 |
| coronene | 7 | 6 |
| fluorene | 5 | 4 |
| fluoranthene | 6 | 5 |
| naphthalene | 6 | 6 |
| phenanthroline | 3 | 3 |
| phenazine | 5 | 4 |
| phenothiazine | 7 | 6 |
| tetracene | 8 | 5 |
| iminodibenzyl[c] | 7 | 5, 6 |
| acridine | 6 | 5 |
| TCNQ | 3 | 2 |
| indole | 4 | 4 |

[a]See FIG. 7 for the structures of coronene and the eight PAH substrates listed below it.
[b]Determined by atmospheric-pressure chemical ionization mass spectrometry.
[c]Iminodibenzyl = 10,11-dihydro-5H-dibenz(b,f)azepine NMR Chemical Shifts and Coupling Constants of Purified PAH(CF$_3$)$_n$ Compounds.

ANTH-5-1.
$^{19}$F NMR: δ −50.40 (singlet, 1CF$_3$); −63.25 (singlet, 2CF$_3$); −66.78 (singlet; 2CF$_3$). $^1$H NMR: δ 9.55 (singlet, 1H); 9.11 (singlet, 2H); 8.23 (singlet, 2H).

ANTH-6-1.
$^{19}$F NMR: δ −51.24 (singlet, 2CF$_3$); −63.50 (singlet, 4CF$_3$). $^1$H NMR: δ 9.17 (singlet, 4H).

AZUL-5-1.
$^{19}$F NMR: δ −54.32 (quartet, J=12.0 Hz, 2CF$_3$); −57.98 (septet, J=12.0 Hz, 1CF$_3$); −65.44 (singlet, 2CF$_3$). $^1$H NMR: δ 9.51 (singlet, 2H); 8.64 (singlet, 1H).

PERY-4-1.
$^{19}$F NMR: δ −58.11 (singlet, 2CF$_3$); −62.74 (singlet, 2CF$_3$). $^1$H NMR: 8.39 (apparent doublet, J=9 Hz, 2H); 8.17 (apparent doublet, J=8 Hz, 2H); 8.10 (multiplet, 4H).

PERY-5-1.
$^{19}$F NMR: δ −57.92 (singlet, 1CF$_3$); −58.29 (singlet, 1CF$_3$); −62.28 (singlet, 1CF$_3$); −63.20 (singlet, 1CF$_3$); −66.20 (singlet, 1CF$_3$). $^1$H NMR: δ 8.63 (singlet, 1H); 8.49 (singlet, 1H); 8.41 (singlet, 1H); ~8.4 (multiplet, 2H); 8.19 (multiplet, 2H).

PERY-5-2.
$^{19}$F NMR: δ −58.38 (singlet, 1CF$_3$); −58.41 (singlet, 1CF$_3$); −62.78 (singlet, 1CF$_3$); −62.82 (singlet, 1CF$_3$); −66.54 (singlet; 1CF$_3$). $^1$H NMR: δ 8.55 (singlet, 1H); 8.43 (broad multiplet, 2H); 8.39 (possible singlet, 1H); 8.24 (multiplet, 1H); ~8.1 (multiplet, 2H).

PERY-5-3.
$^{19}$F NMR: δ −58.09 (apparent singlet, 1CF$_3$); −58.11 (apparent singlet, 1CF$_3$); −62.20 (singlet, 1CF$_3$); −63.17 (singlet, 1CF$_3$); −66.17 (singlet; 1CF$_3$). $^1$H NMR: δ 8.66 (singlet, 1H); 8.50 (singlet, 1H); ~8.4 (multiplet, 3H); ~8.2 (multiplet, 2H).

PERY-5-4.
$^{19}$F NMR: δ −57.93 (singlet, 1CF$_3$); −58.11 (singlet, 1CF$_3$); −58.41 (multiplet, 2CF$_3$); −63.16 (singlet, 1CF$_3$). $^1$H NMR: the spectrum was difficult to assign due to the low signal/noise ratio and the presence of broad multiplets.

PERY-6-1. $^{19}$F NMR: δ −58.66 (singlet, 2CF$_3$); −62.70 (singlet, 2CF$_3$); −66.57 (singlet, 2CF$_3$). $^1$H NMR: δ 8.64 (singlet, 2H); 8.48 (singlet, 2H); 8.44 (singlet; 2H).

PHEN-5-1.
$^{19}$F NMR: δ −61.96 (singlet, 1CF$_3$); −62.31 (quartet, J=13.0 Hz, 1CF$_3$); −62.56 (quartet, J=13.0 Hz, 1CF$_3$); −63.66 (singlet, 1CF$_3$); −65.69 (singlet, 1CF$_3$). $^1$H NMR: δ 9.26 (singlet, 1H); 9.23 (singlet, 1H); 8.82 (singlet, 1H); 8.80 (singlet, 1H); 8.41 (singlet, 1H).

PYRN-5-1.
$^{19}$F NMR: δ −57.59 (quartet, J=19 Hz, 1CF$_3$); −58.42 (quartet, J=19 Hz, 1CF$_3$); −60.30 (singlet, 1CF$_3$); −60.74 (singlet, 1CF$_3$); −60.86 (singlet, 1CF$_3$). $^1$H NMR: δ 9.12 (singlet, 1H); 8.83 (multiplet, 2H); 8.80 (multiplet; 2H).

PYRN-5-2
(contaminated with ca. 30 mol % PYRN-5-3). $^{19}$F NMR: δ −57.90 (quartet, J=19 Hz, 1CF$_3$); −58.42 (quartet, J=19 Hz, 1CF$_3$); −60.37 (singlet, 1CF$_3$); −60.71 (singlet, 1CF$_3$); −63.64 (singlet, 1CF$_3$). $^1$H NMR: it is difficult to distinguish between the spectra of PYRN-5-2 and PYRN-5-3.

PYRN-5-3
(a likely impurity of PYRN-5-2). $^{19}$F NMR: δ −57.68 (quartet, J=19 Hz, 1CF$_3$); −58.30 (quartet; J=19 Hz, 1CF$_3$); −60.57 (singlet, 1CF$_3$); −60.94 (singlet, 1CF$_3$); −63.51 (singlet, 1CF$_3$). $^1$H NMR: it is difficult to distinguish between the spectra of PYRN-5-2 and PYRN-5-3.

PYRN-6-1.
$^{19}$F NMR: δ −58.25 (quartet; J=18 Hz, 2CF$_3$); −58.66 (quartet, J=18 Hz, 2CF$_3$), −60.95 (singlet, 2CF$_3$). $^1$H NMR: $^1$H NMR: δ 9.07 (singlet, 2H); 8.80 (singlet, 2H).

TRPH-6-1.
$^{19}$F NMR: δ −57.21 (singlet, 1CF$_3$); −62.32 (multiplet, 2CF$_3$); −62.51 (roofed quartet, J=11 Hz, 1CF$_3$); −62.64 (roofed quartet, J=11 Hz, 1CF$_3$); −65.78 (singlet; 1CF$_3$). $^1$H NMR: δ 9.19 (singlet, 1H); ~9.1 (multiplet, 4H); 8.49 (singlet, 1H).

X-Ray Structures.

Seven X-ray structures determined in this work have had their .cif files deposited with the Cambridge Crystallographic Data Center (CCDC). These seven structures are for pure compounds and do not contain solvent molecules: ANTH-5-1, PERY-4-1, PERY-5-1, PHEN-5-1, PYRN-5-1, PYRN-6-1, and TRPH-6-1. In addition, five preliminary X-ray structures have been determined in this work. The data are of sufficient quality to determine the addition patterns of the molecules and the nature of the solid-state packing, but have R$_w$ factors greater than 20% and therefore have not been deposited with the CCDC. Better data sets are being collected, and these structures will be deposited with the CCDC in due course.

Plots of ANTH(CF$_3$), and PYRN(CF$_3$), Electron Affinities Vs. N.

Figure 7:
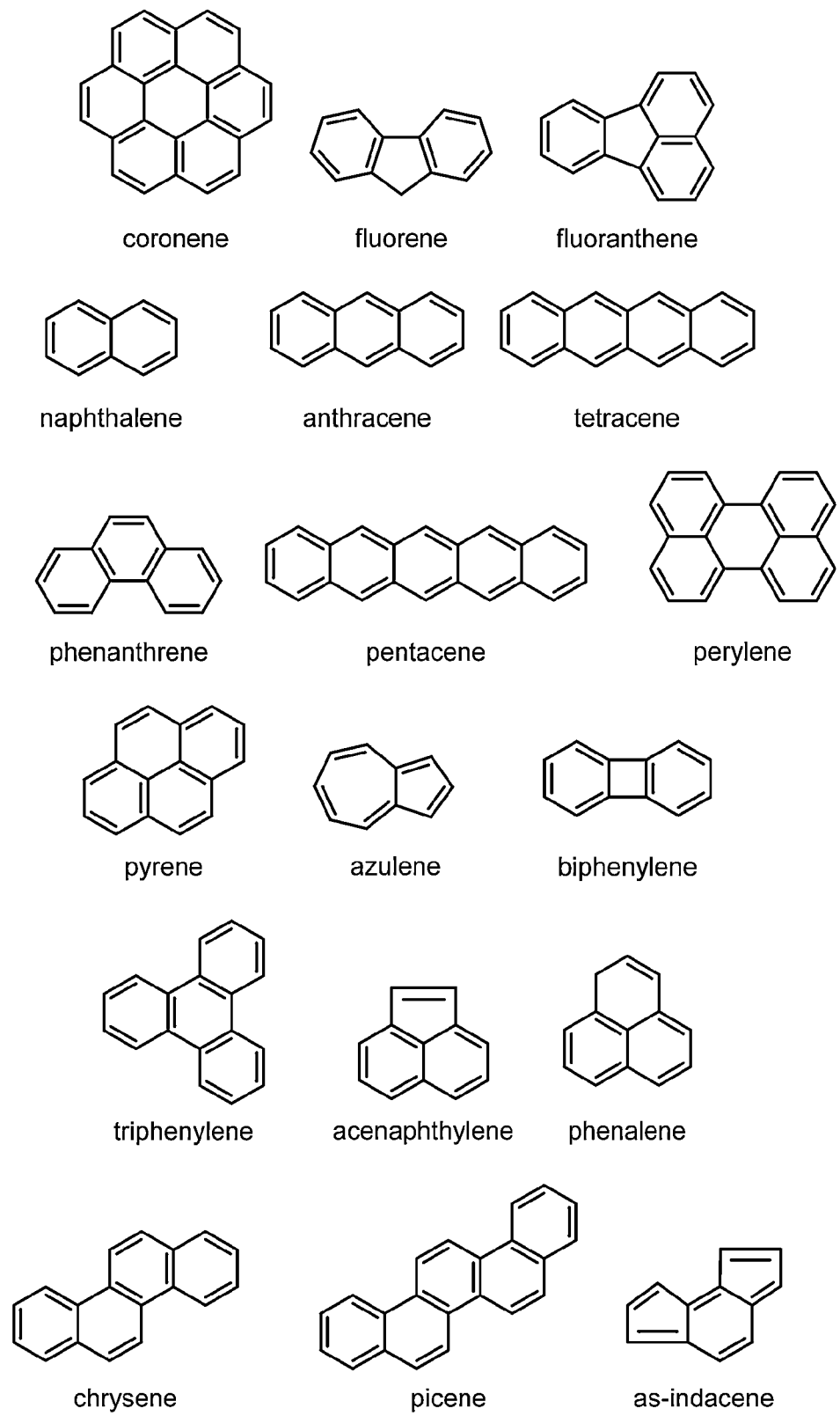
FIG. 7. Examples of polyaromatic hydrocarbon substrates that can be used in the methods of the invention, according to various embodiments.
Figure 8:
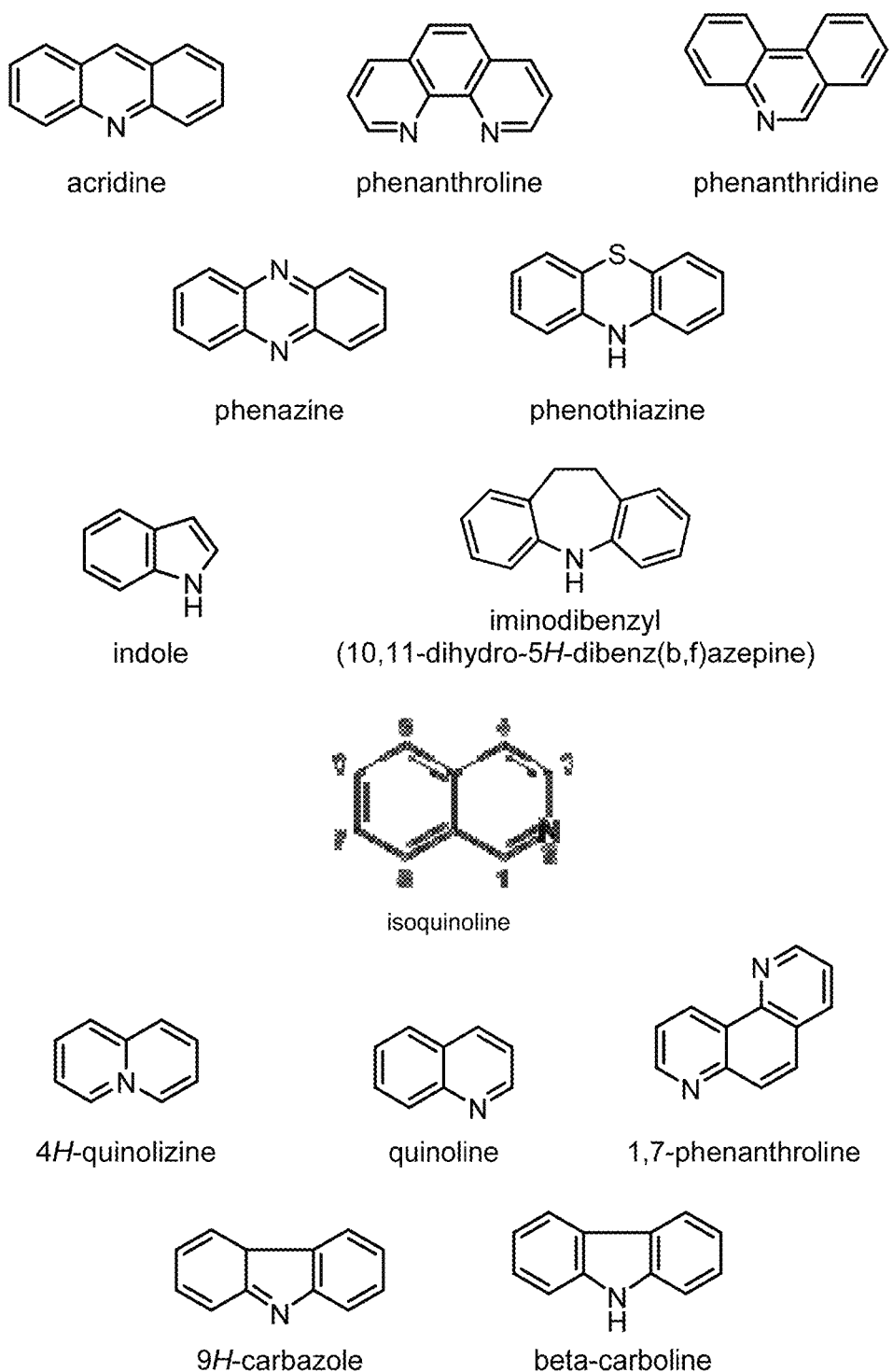
FIG. 8. Examples of polyheterocyclic compound substrates that can be used in the methods of the invention, according to various embodiments.
Figure 9:
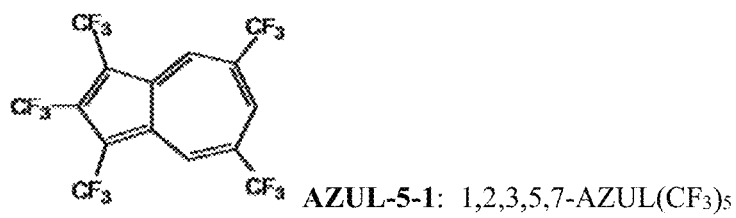
FIG. 9. Various specific products and general formulas of products of the methods of the invention, according to various embodiments.
Figure 9:
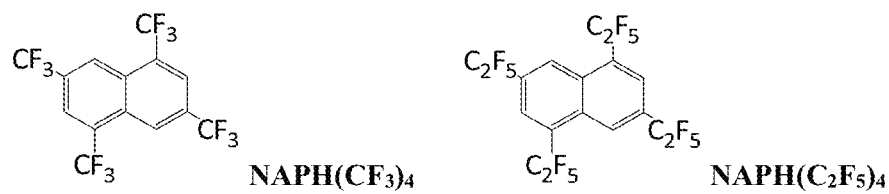
Figure 9:
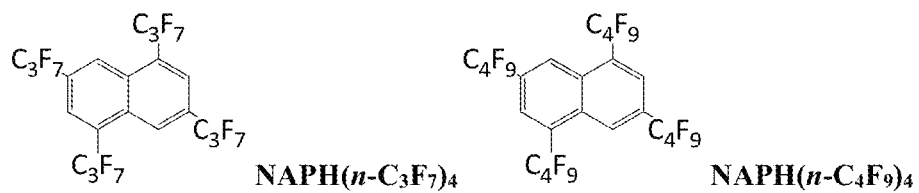
Figure 9:
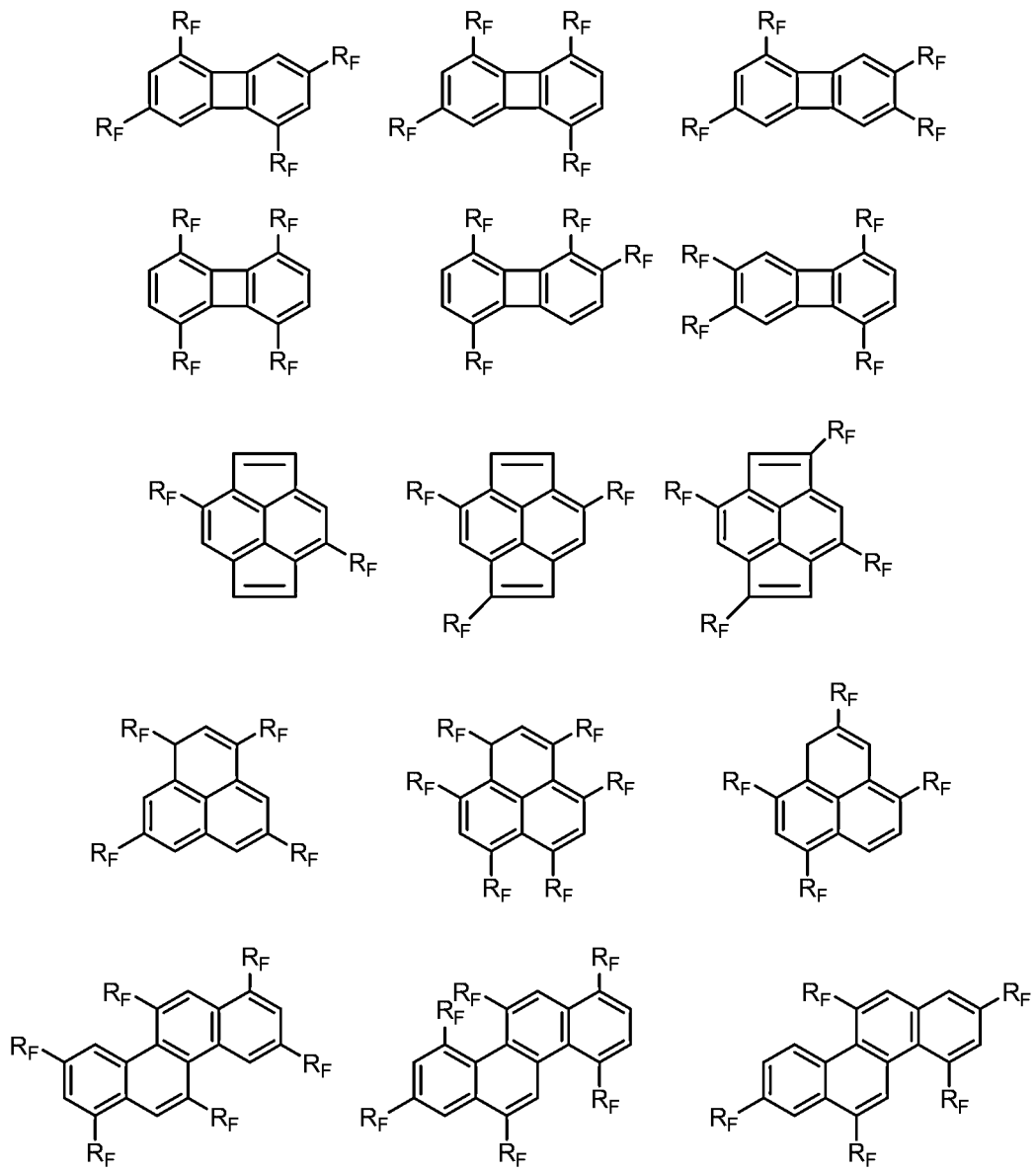
Figure 10:
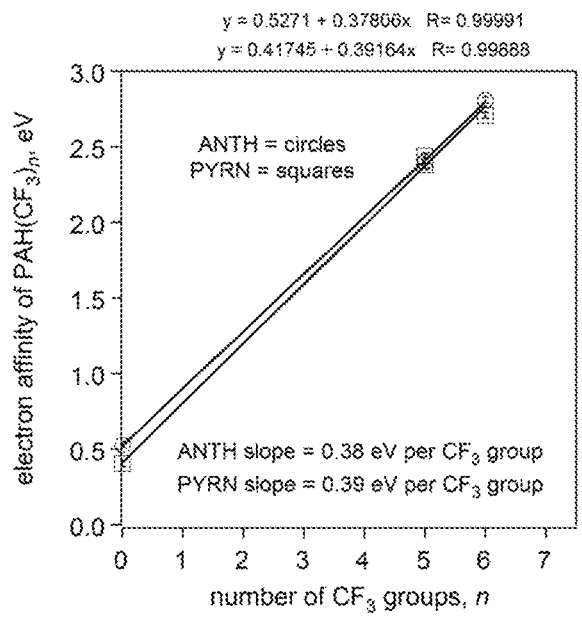
FIG. 10. Plots of ANTH(CF$_3$)$_n$ and PYRN(CF$_3$)$_n$ electron affinities vs. n, based on experimental gas-phase electron affinities (cf. the corresponding graph for PERY(CF$_3$)$_n$ compounds in FIG. 4).

The plots in FIG. 7 are based on the experimental gas-phase electron affinities determined in this work (cf. the corresponding graph for PERY(CF$_3$)$_n$ compounds in FIG. 4). Note that the uncertainties for the experimental electron affinities, shown by brackets, are smaller than the data points.

Example 2

Single-Step Gas-Phase Polyperfluoroalkylation of Naphthalene

Fluorine or perfluoroalkyl substituents strongly augment physicochemical and biological properties of organic molecular substrates. Organofluorine compounds have been designed for medicinal applications such as drug discovery and diagnostic imaging. One example of the importance of perfluoroalkyl modification to drug discovery is the CF$_3$-bearing fluoxetine, ((RS)—N-methyl-3-phenyl-3-[4-(trifluoromethyl)-phenoxy]propan-1-amine) known as Prozac, one of the most common antidepressants. Another recently emerged field for applications of organofluorine compounds is molecular electronics. The incorporation of electron withdrawing perfluoroalkyl groups in polycyclic aromatic hydrocarbons (PAHs) has been predicted theoretically and demonstrated experimentally to yield air-stable n-type organic semiconductors with potentially higher electron mobility performance than the non-fluorinated state-of-the-art analogs.

Several methodologies for introducing CF$_3$ groups into aromatics and heterocyclics have been described in the literature (see, for example, Schlosser, *Angew. Chem. Int. Ed.* 2006, 45, 5432-5446). These reactions typically result in one or, more rarely, two CF$_3$ substituents attached to the aromatic substrate. A known exception is hexakis(trifluoromethyl) benzene prepared via a cyclization of three bis(trifluoromethyl)acetylene molecules or a reaction of hexaiodobenzene with trifluoromethylcopper.

For naphthalene, several mono- and bis-substituted CF$_3$ derivatives have been reported [[10] a) S. Roy, B. T. Gregg, G. W. Gribble, V.-D. Le and S. Roy, *Tetrahedron* 2011, 67, 2161-2195; b) F. Bailly, F. Cottet and M. Schlosser, *Synthesis* 2005, 791-797; c) K. Hosokawa and K. Inukai, *Nippon Kagaku Kaishi* 1972, 383-386; d) K. Hosokawa and K. Inukai, *Nippon Kagaku Kaishi* 1976, 1791-1793; e) K. Hosokawa, S. Fujii and K. Inukai, *Nippon Kagaku Kaishi* 1979, 294-296; f) K. Hosokawa and K. Inukai, *Nippon Kagaku Kaishi* 1977, 1163-1167; g) T. C. Klebach, L. A. M. Turkenburg and F. Bickelhaupt, *Tetrahedron Lett.* 1978, 19, 1099-1100.] while only one highly substituted derivative (2,3,6,7-tetrakis-(trifluoromethyl)naphthalene) has been reported (Krespan et al., *J. Am. Chem. Soc.* 1961, 83, 3428-3432). Syntheses of mono- and bis-(trifluoromethyl)naphthalenes have been typically accomplished via multi-step reactions: i) "assembly" of the naphthalene core from CF$_3$-bearing organic precursor molecules (using Friedel-Crafts intramolecular cyclization or Diels-Alder cyclization with CF$_3$-carrying benzyne intermediate to form the naphthalene core); ii) fluorination of naphthalene derivatives bearing suitable CF$_3$-"precursor" groups (fluorination of naphthoic acids by SF$_4$ or fluorination of (naphthalene)methyldithiocarboxylates by H$_2$F$_3$$^−$ fluorine source and 1,3-dibromo-5,5-dimethylhydantoin (DBDMH) oxidize); and iii) direct substitution of iodine in various iodonaphthalenes with CF$_3$ group(s) using (trifluoromethyl)copper generated in situ.

In this Example, we report a simple and highly efficient alternative approach: substitution of multiple aromatic hydrogen atoms in naphthalene with R$_F$. radicals generated by thermolysis of R$_F$I precursors (R$_F$=CF$_3$, C$_2$F$_5$, n-C$_3$F$_7$, and n-C$_4$F$_9$).

Results and Discussion.

Synthesis and Characterization.

The perfluoroalkylation reactions were accomplished by reacting eight equivalents of R$_F$I (R$_F$=CF$_3$, C$_2$F$_5$, n-C$_3$F$_7$, or n-C$_4$F$_9$) with one equivalent of naphthalene at 300° C. for 3 hours in sealed Pyrex glass ampoules, as shown in Scheme 2.1. Complete vaporization of naphthalene was observed at ca. 150° C. before any visible formation of iodine due to R$_F$I dissociation, indicating that the perfluoroalkylation took place fully in the gas phase.

Scheme 2.1. Gas phase perfluoroalkylation of napthalene (n = 1-6).

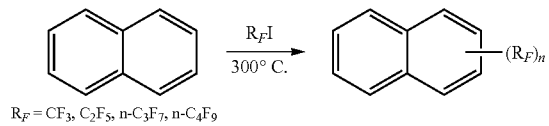

$R_F = CF_3, C_2F_5, n-C_3F_7, n-C_4F_9$

After the removal of iodine (with an aqueous $Na_2S_2O_3$ wash), the crude off-white solid products were weighed, dissolved in 3.0 mL of 5.3 mM solution of $(n-Bu)_4NBF_4$ in $CDCl_3$, and analyzed by quantitative $^1H$ and $^{19}F$ NMR spectroscopy. Due to the presence of $(n-Bu)_4NBF_4$ internal standard, the relative molar concentrations of aromatic H atoms and $R_F$ groups could be determined via integration of the NMR spectra (Dolbier, W. R., *Guide to Fluorine NMR for Organic Chemists*, John Wiley & Sons, Inc., New Jersey, 2009). This information was used to determine the average number of $R_F$ groups per NAPH core, which, in turn, allowed us to calculate the total molar yield of crude products; see Table 2.1. No unreacted naphthalene was detected in any of the four crude products by $^1H$ NMR spectroscopy, which demonstrates the completeness of the naphthalene conversion.

TABLE 2.1

Molar yields of crude $NAPH(R_F)_n$ products.

| product | $R_F$ | molar yield of crude $NAPH(R_F)_n$, % | average $n(R_F)$ per NAPH core |
|---|---|---|---|
| A | $CF_3$ | 80 ± 15 | 2.4 ± 0.1 |
| B | $C_2F_5$ | 70 ± 15 | 2.3 ± 0.1 |
| C | $n-C_3F_7$ | 95 ± 10 | 1.9 ± 0.1 |
| D | $n-C_4F_9$ | 95 ± 10 | 1.9 ± 0.1 |

Negative ion atmospheric pressure chemical ionization (NI-APCI) mass spectrometry has been applied to determine the maximal substitution degree in samples A-D. Earlier, NI-APCI mass spectrometry was found to be highly effective for the direct analysis of perfluoroalkylation products of larger PAHs, but the analogous mass spectrometry analysis of products A-D required use of a reducing agent (tetrakis(dimethylamino)ethylene (TDAE) to generate $NAPH(R_F)_n^-$ anions. Treatment with TDAE, which has an ultra-low ionization potential of 5.3 eV, led to the color change from a very pale-yellow color to a pale-green (for $R_F=CF_3$) or to a dark-yellow (for $R_F=C_2F_5$, $n-C_3F_7$, and $n-C_4F_9$) color suggesting the formation of $NAPH(R_F)_n^-$. radical anions. Indeed, these chemically reduced $NAPH(R_F)_n$ samples produced mass spectra shown on FIG. 11, in which the maximum number of $R_F$ substituents was five for $R_F=CF_3$ and four for $R_F=C_2F_5$, $n-C_3F_7$, and $n-C_4F_9$. Lower-mass peaks due to loss of HF have been observed more prominently for $R_F=C_2F_5$. Their fragmentation origin was established upon analysis of the purified compounds. The lower degree of perfluoroalkylation observed for the longer-chain $R_F$ groups is consistent with their larger steric requirements in comparison to $CF_3$ groups.

Perfluoroalkylation resulted in significant changes in physical properties compared to the parent naphthalene. For example, solubility of tetra-substituted derivatives $NAPH(R_F)_4$ in polar solvents was strongly reduced compared to bis- and tris-derivatives. The finding allowed us to develop a simple and efficient method of isolation of 95+%-pure $NAPH(R_F)_4$ compounds from the crude materials using fast and simple precipitation/wash protocols with ca. 5-10 mol % yield (calculated relative to the starting naphthalene). The compositional purity was confirmed by NI-APCI mass spectrometry. As mentioned above, isolated low-solubility samples readily formed molecular anions $NAPH(R_F)_4^-$ when chemically reduced by TDAE in solution. Notably, partial fragmentation due to loss of one and two HF molecules was observed for $NAPH(C_2F_5)_4$ and $NAPH(n-C_3F_7)_4$ and for $NAPH(n-C_4F_9)_4$.

Figure 12:
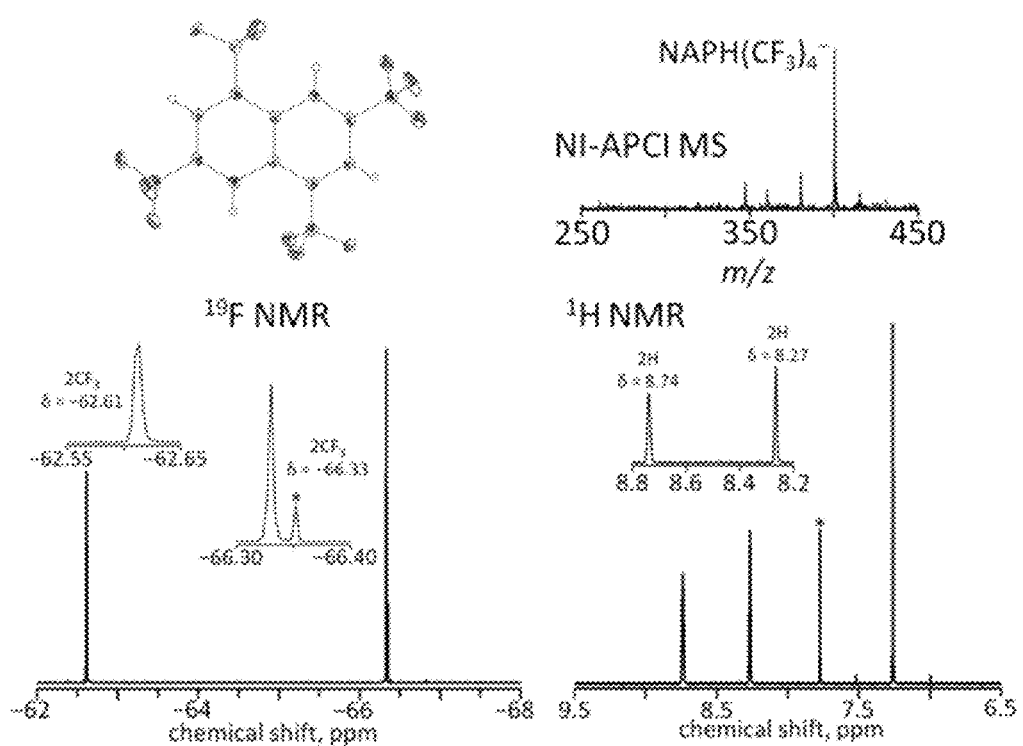
FIG. 12. Single-crystal X-ray diffraction structure of 1,3,5,7-NAPH(CF$_3$)$_4$, 50% probability ellipsoids used for all non-hydrogen atoms of the ORTEP drawing (top left), NI-APCI mass spectrum (TDAE-reduced; top right), $^{19}$F NMR (bottom left), and $^1$H NMR spectra (bottom right) with expansions of the 95%+ pure 1,3,5,7-NAPH(CF$_3$)$_4$. Peaks marked with asterisks are due to internal standard, and peak at δ 7.26 due to solvent (CDCl$_3$).
Figure 13:
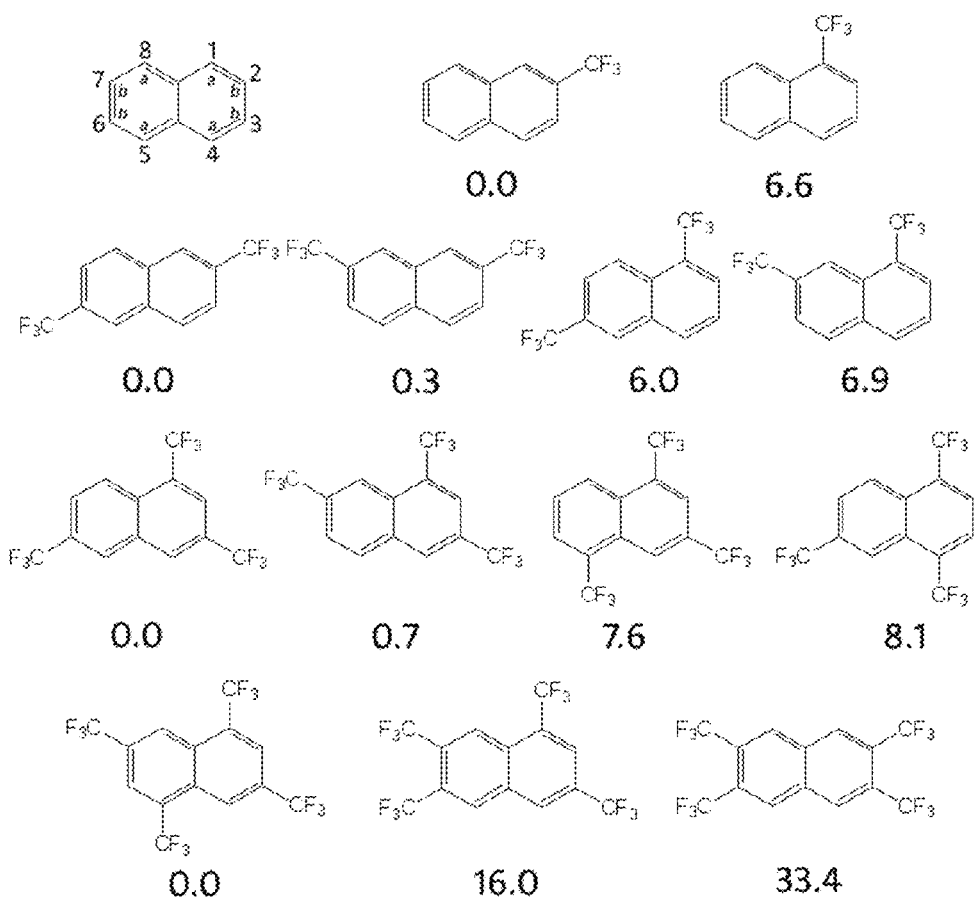
FIG. 13. Numbering scheme (1 through 8) and symmetry related positions (a and b) for substitutions in NAPH and drawings of the most stable isomers of NAPH(CF$_3$)$_{1-4}$, DFT-calculated relative energies (in kJ/mol) are given under each structure.

Proton and fluorine-19 NMR spectroscopy revealed the isomeric purity of the isolated compounds, which possess the idealized $C_{2h}$ symmetry, thus allowing for unambiguous structural assignment for the 1,3,5,7-pattern of $R_F$ groups for all four isolated compounds; see FIG. 12 and for NMR data and FIG. 13 for NAPH core numbering scheme.

Preliminary studies of the remaining soluble fractions after the extraction of $NAPH(R_F)_4$ compounds were carried out, which determined the presence of several isomers of $NAPH(R_F)_n$ where n=2 or 3, in agreement with the NMR data on the average molecular compositions (see Table 2.1). While the use of an HPLC method for separation of $NAPH(CF_3)_{2,3}$ and $NAPH(n-C_3F_7)_{2,3}$ has not yet been optimized, one isomer of $NAPH(C_2F_5)_2$ and one isomer of $NAPH(C_2F_5)_3$ were isolated with high purity, and tentative structural assignments were proposed for them and for the second identified abundant isomer of $NAPH(C_2F_5)_3$ based on NMR and DFT data.

DFT Relative Energies of $NAPH(R_F)_n$.

To determine possible substitution patterns of $R_F$ groups for NAPH, we have performed DFT computations for all isomers of $NAPH(CF_3)_n$ (n=1-4) at the DFT level of theory. Complete list of isomers and their relative energies were prepared. The main trends are as follows. Unsubstituted NAPH has two types of C(H) atoms, C1 and symmetry related C4, C5, and C8 (designated them as an a-type position) and position C2 and related C3, C6, and C7 (denoted as b), as shown on FIG. 13.

An increase of the number of attached $CF_3$ groups results in the rich variety of their relative positions and hence possible isomers. From ten possible isomers of $NAPH(CF_3)_2$, the most stable ones are those which combine two $CF_3$ groups in distant b-type positions (isomers 2,6 and 2,7 are isoenergetic within 0.3 kJ/mol). They are followed by three isomers combining a and b-type groups (1,3, 1,6, and 1,7 with relative energies of 8, 6 and 7 kJ/mol, respectively) and then by two isomers with only a-type distant positions (1,4 and 1, 5 with ΔE of 16 and 13 kJ/mol). It can be seen that when $CF_3$ groups are at distant positions (i.e., do not interact), relative energies can be roughly rationalized as a number of groups in position a times an increment of ca. 7 kJ/mol. However, when two $CF_3$ groups are close enough to interact, such interaction significantly destabilized the structures. The isomer 2,3 with two neighboring $CF_3$ groups in adjacent b-type positions has an energy of 25 kJ/mol, two $CF_3$ groups in adjacent a and b positions 50 kJ/mol, whereas the least stable isomer has two $CF_3$ groups in close a-type position (1,8). In the latter, naphthalene framework is non-planar to avoid close $CF_3 \ldots CF_3$ contacts.

Three $CF_3$ groups can be arranged in $NAPH(CF_3)_3$ in 13 different ways, and the relative energies of these isomer span the range of 106 kJ/mol. Because it is impossible to arrange all three groups in b-type position and avoid close $CF_3 \ldots CF_3$ contacts, the lowest energy isomers are those combining one a-type and two b-type groups (1,3,6 and 1,3,7). These isomers are followed by two isomers with two a-sites and one b-site (1,3,5 and 1,4,6; ΔE=8 kJ/mol for both isomers). All other isomers have at least one pair of neighboring $CF_3$ groups and hence are less stable. From them, the most stable is isomer 2,3,6 with relative energy of 18 kJ/mol followed by the isomer 1,2,6 whose relative energy is already 42 kJ/mol. The least stable isomers have three groups in neighboring positions (1,2,3 and 1,2,8).

The largest number of isomers in the whole NAPH(CF$_3$)$_n$ series, 21, is possible for n=4. However, four CF$_3$ groups are already too crowded, and 1,3,5,7-NAPH(CF$_3$)$_4$ is the only isomer without adjacent CF$_3$ groups. The second most stable isomer with ΔE of 16 kJ/mol has CF$_3$ groups in 1,3,6,7 position, whereas the earlier reported 2,3,6,7-NAPH(CF$_3$)$_4$ is the third most stable isomer with the relative energy of 33 kJ/mol. The energies of other isomers span the range of 41-142 kJ/mol. It is clear that the 2,3,6,7-isomer was a kinetic product whose structure was directed by the synthetic pathway (Krespan et al., *J. Am. Chem. Soc.* 1961, 83, 3428-3432). Conversely, the high temperature synthetic method used in this work tends to give thermodynamic products.

X-Ray Structures.

Figure 14:
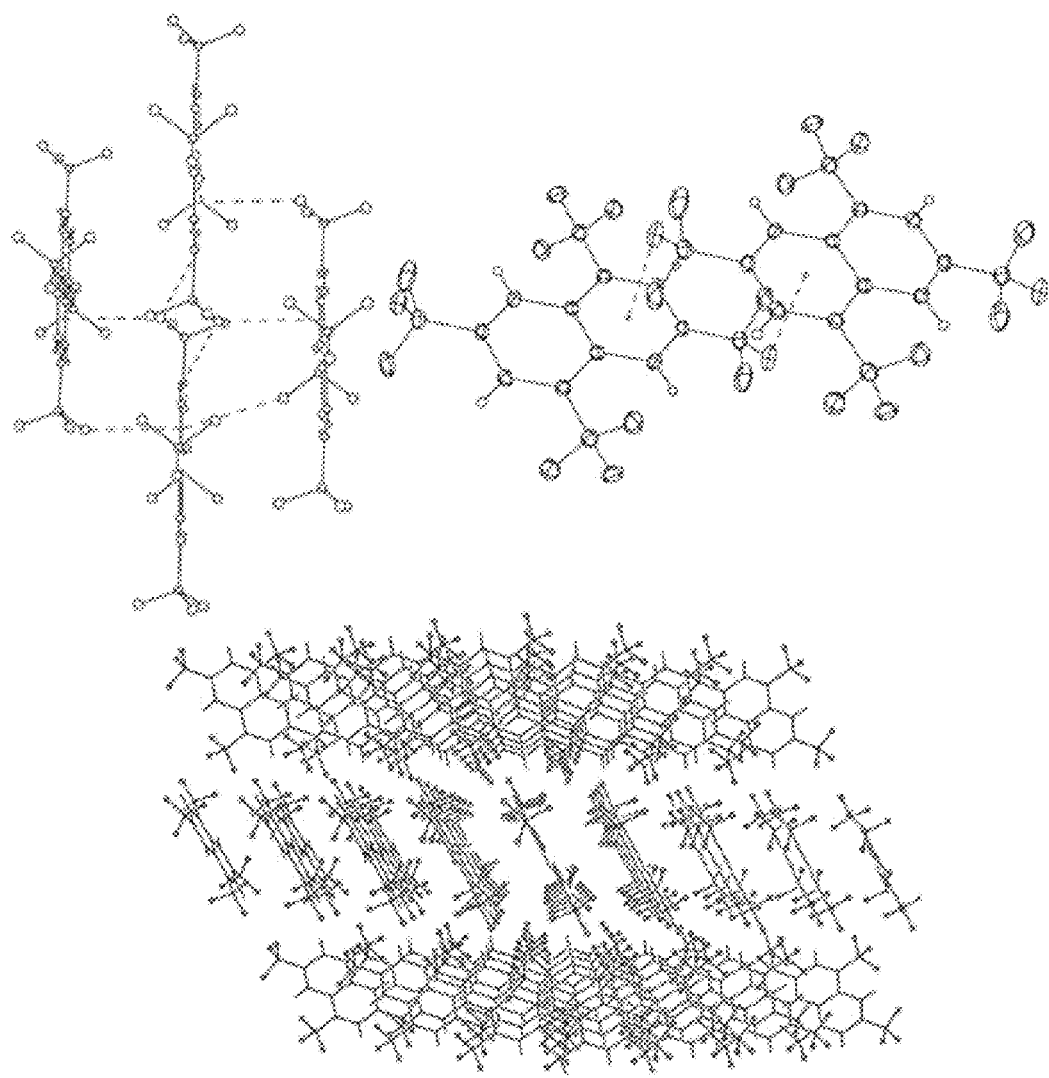
FIG. 14. Crystal packing in 1,3,5,7-NAPH(CF$_3$)$_4$.
Figure 15:
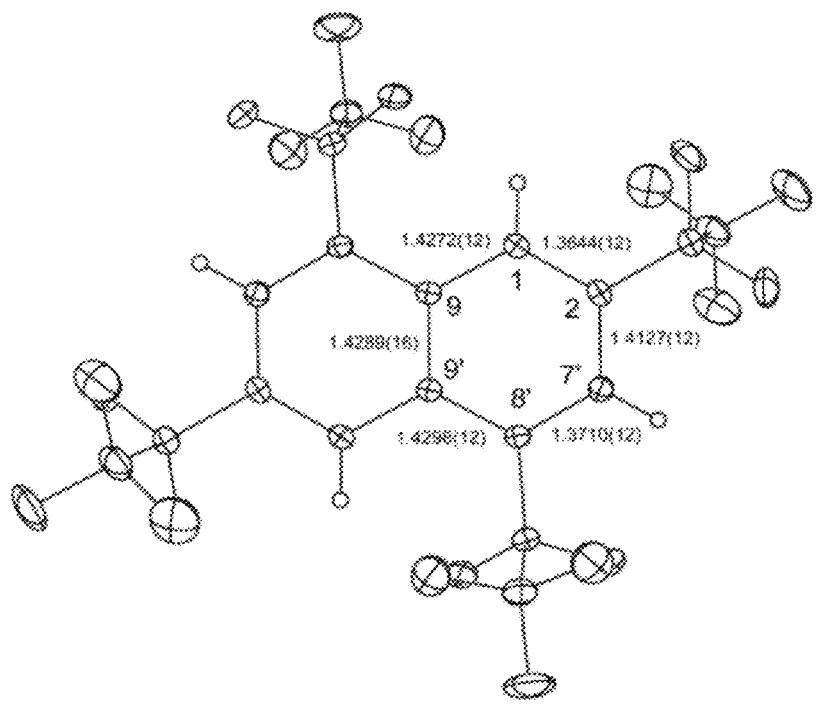
FIG. 15. (A) Single-crystal X-ray diffraction structure of 1,3,5,7-NAPH(C$_2$F$_5$)$_4$, 50% probability ellipsoids used for all non-hydrogen atoms of the ORTEP drawing. (B) Crystal packing in 1,3,5,7-NAPH(C$_2$F$_5$)$_4$. Fluorine and hydrogen atoms are removed for clarity.
Figure 15:
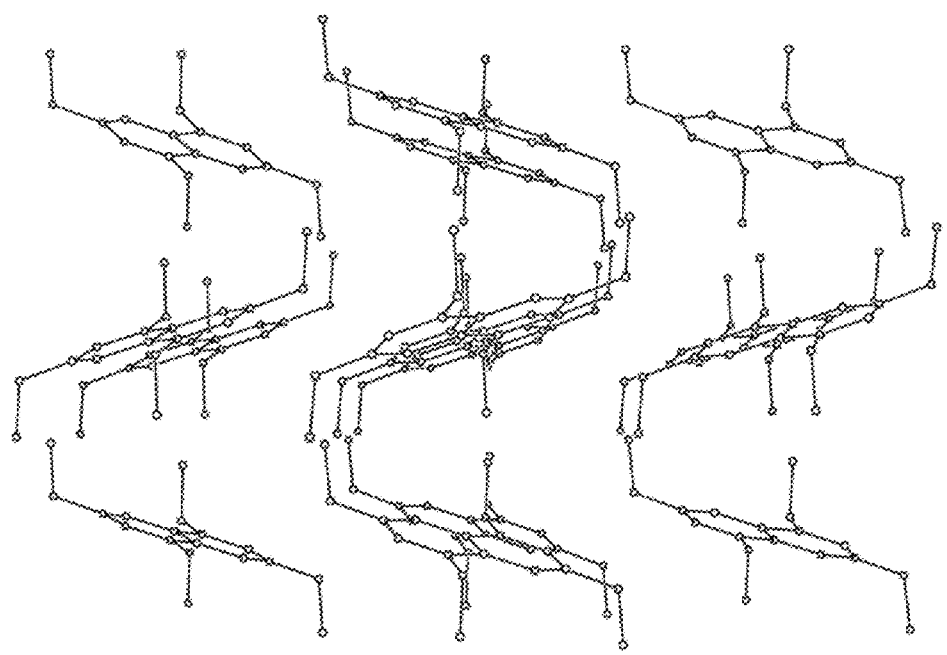

The structures of 1,3,5,7-NAPH(CF$_3$)$_4$ (FIG. 14) and 1,3,5,7-NAPH(C$_2$F$_5$)$_4$ (FIG. 15) were unambiguously confirmed by the single-crystal X-ray diffraction study. The molecular structure of 1,3,5,7-NAPH(CF$_3$)$_4$ is more planar and less distorted than expected, and with an interesting packing motif. The distances between the closest overlapping parallel planes of the naphthalene cores of 1,3,5,7-NAPH(CF$_3$)$_4$ are decreased to 3.75 Å or 4.23 Å from 6.77 Å in the parent naphthalene. The addition of the CF$_3$ groups increases the intermolecular interactions through a F—H close contact of 2.631 Å and a F-to-naphthalene centroid distance of 3.089 Å which pulls the molecules within a layer of parallel oriented naphthalene molecules closer together.

The overall packing structure of the CF$_3$ groups in one layer of molecules point towards each other creating a channel between layers of 1,3,5,7-NAPH(CF$_3$)$_4$, the rings between layers are rotated 83.6° (increased from 50.7° in naphthalene) from planes of adjacent layers, but the naphthalene cores are rigorously parallel within their respective layers. When rotated 90° about the central horizontal, it exhibits the common herringbone pattern. The addition of the CF$_3$ groups to naphthalene increases intermolecular interactions between CF$_3$ groups and naphthalene cores. The increase in R$_F$ moiety length to the NAPH(C$_2$F$_5$)$_4$ compound creates packing with distinct naphthalene regions and perfluoroethyl regions (see FIG. 15). The closest distance between overlapping parallel planes of NAPH(C$_2$F$_5$)$_4$ is 10.575 Å. There are 3 different orientations of the naphthalene cores in NAPH (C$_2$F$_5$)$_4$, and it is evident that the structure is dominated by the rigid C$_2$F$_5$ moiety rather than by any other interactions.

The melting points and the sublimation rates of naphthalene, 1,3,5,7-NAPH(CF$_3$)$_4$, and 1,3,5,7-NAPH(C$_2$F$_5$)$_4$ were measured (see Table 2.2 and experimental details below). The highest melting point was observed for 1,3,5,7-NAPH(CF$_3$)$_4$, followed by 1,3,5,7-NAPH(C$_2$F$_5$)$_4$, and then naphthalene. The sublimation rates were measured in the TGA instrument at 25.0° C. under a constant stream of nitrogen, and were found to decrease from naphthalene to 1,3,5,7-NAPH(CF$_3$)$_4$ to 1,3,5,7-NAPH(C$_2$F$_5$)$_4$, in accord with their molecular weights. Volatility of pentafluoroethyl naphthalene derivatives were reported to contribute to lower isolated yields.

TABLE 2.2

Melting points and sublimation rates of NAPH, 1,3,5,7-NAPH(CF$_3$)$_4$, and 1,3,5,7-NAPH(C$_2$F$_5$)$_4$ at 25.0° C.

| compound | melting point, ° C. | sublimation rate, μmol min$^{-1}$ |
|---|---|---|
| NAPH | 75.0-78.0 | $3.6 \cdot 10^{-2}$ |
| 1,3,5,7-NAPH(CF$_3$)$_4$ | 99.0-99.8 | $3.7 \cdot 10^{-3}$ |
| 1,3,5,7-NAPH(C$_2$F$_5$)$_4$ | 88.5-89.0 | $7.3 \cdot 10^{-4}$ |

Cyclic Voltammetry.

Figure 16:
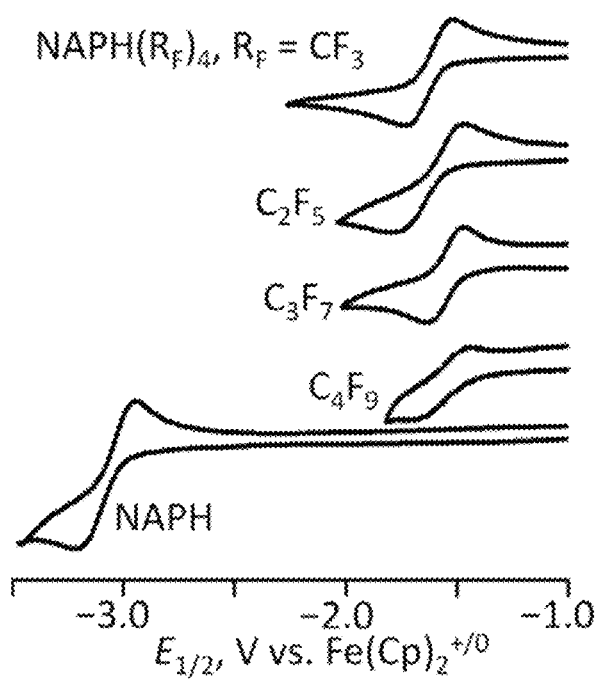
FIG. 16. Cyclic voltammograms (scan rate 100 mV·s$^{-1}$) of naphthalene (NAPH) and pure 1,3,5,7-NAPH(R$_F$)$_4$ compounds in dimethoxyethane (0.1 M (n-Bu)$_4$NClO$_4$). All five CVs are shown relative to Fe(Cp$_2$)$^{+/0}$ defined as 0.0 V.

Electrochemical properties of 1,3,5,7-NAPH(R$_F$)$_4$ (R$_F$=CF$_3$, C$_2$F$_5$, n-C$_3$F$_7$, and n-C$_4$F$_9$) were studied by cyclic voltammetry and square-wave voltammetry in 0.1 M solution of (n-Bu)$_4$NClO$_4$ in dry deoxygenated dimethoxyethane under inert atmosphere; see FIG. 16. The compounds displayed a quasi-reversible first reduction except for 1,3,5,7-NAPH(n-C$_4$F$_9$)$_4$ which was difficult to assess due to its low solubility in dimethoxyethane. The first reduction potentials of 1,3,5,7-NAPH(R$_F$)$_4$ were anodically shifted by 1.46, 1.45, 1.53, and 1.52 V from naphthalene for R$_F$=CF$_3$, C$_2$F$_5$, n-C$_3$F$_7$, and n-C$_4$F$_9$, respectively. It should be noted that the electron-withdrawing effects of different R$_F$ groups cannot be compared directly using only the data on the first reduction potentials due to differences in the solvation energies. For example, our earlier study of 1,7-C$_{60}$(R$_F$)$_2$ compounds showed how solvation energy differences can compensate the higher electron affinity of the molecules bearing longer R$_F$ groups, leading to equalization of the observed solution-phase first reduction potentials across the series of different R$_F$ substituents. It is notable that earlier studies of R$_F$-substituted perylene diimides and R$_F$-substituted nitrobenzenes showed negligible differences in the first reduction potentials between molecules bearing different R$_F$ groups, which may also be due to the similar "equalizing" effect of solvation energy.

The overall shift in E$_{1/2}$ of 1,3,5,7-NAPH(R$_F$)$_4$ relative to NAPH (ca. 1.5 V) is surprisingly big, especially when compared to the 0.95 V shift of E$_{1/2}$ observed for the penta(trifluoromethyl)corannulene C$_5$-C$_{20}$H$_5$(CF$_3$)$_5$, or 0.2 V shift in tetrakis(trifluoromethyl)fullerene C$_{60}$(CF$_3$)$_4$, relative to their respective parent molecules. This suggests that the electron-withdrawing effect of the R$_F$ groups may vary greatly for organic substrates of different sizes and structures. Earlier DFT calculations performed on the series of fluorinated and trifluoromethylated acenes agree with these findings: the largest incremental shift in reduction potential and electron affinity was found for benzene, followed by naphthalene, and then larger acenes.

Figure 11:
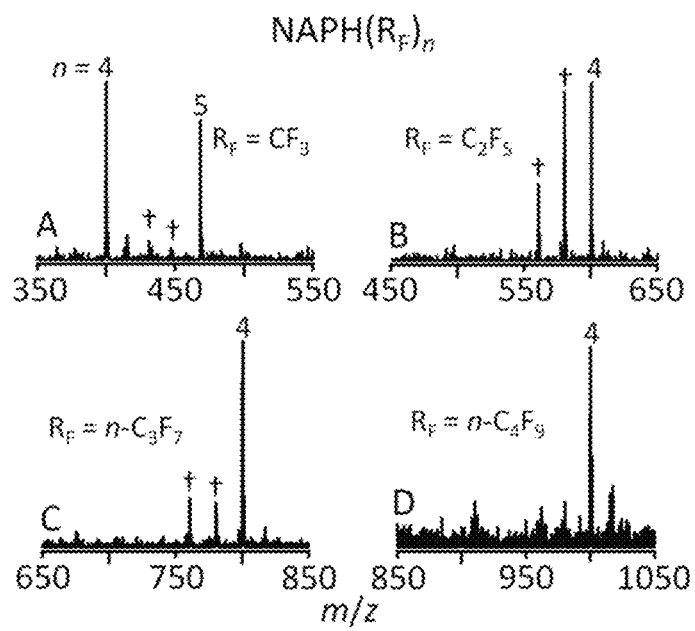
FIG. 11. Negative-ion APCI mass spectra of the TDAE-reduced crude products of naphthalene perfluoroalkylation: A) NAPH(CF$_3$)$_n$; B) NAPH(C$_2$F$_5$)$_n$; C) NAPH(n-C$_3$F$_7$)$_n$; and D) NAPH(n-C$_4$F$_9$)$_n$. Peaks marked with daggers are due to fragments resulting from loss of HF from parent ions.

The observed large enhancement in electron accepting properties of NAPH(R$_F$)$_m$ in solution helps explain the fact that peaks due to NAPH(R$_F$)$_{2,3}$ were not observed mass spectrometrically in samples A-D (FIG. 11), despite the "fluorophilicity" based HPLC analysis and NMR evidence (Table 2.1) that they represent the bulk of the crude products. This is likely due to i) their low electron affinity (EA) (or reduction potentials in solution) and ii) presence of the species with significantly higher EAs in these crude samples (i.e., NAPH (R$_F$)$_4$). A strong correlation between the EA of an analyte and its ionization efficiency under NI-APCI conditions as well as the suppression of the signals from less electronegative molecules is well documented in the literature. The results of earlier theoretical and experimental data showed that EAs of poly(trifluoromethyl)PAHs increase roughly proportionately to the number of $CF_3$ substituents. Using the calculated EA values of NAPH (−0.511 eV) and hypothetical $NAPH(CF_3)_8$ (3.262 eV), the mean EA increase of 0.47 $eV/n(CF_3)$ in $NAPH(CF_3)_n$ can be calculated. Therefore the estimated $EA(NAPH(R_F)_n)$ values for n=2 (0.432 eV) and n=3 (0.904 eV) are apparently too low for these species to be observed in NI-APCI mass spectrometry, even with TDAE-assisted chemical reduction. At the same time, the peak due to NAPH $(CF_3)_5^-$ (with the estimated $EA(NAPH(CF_3)_5)$ of ca. 1.84 eV) is likely to be overrepresented in the mass spectrum compared to its real content in the crude mixture (FIG. 11, top left).

As mentioned above, literature experimental data on the synthesis of polysubstituted perfluoroalkylnaphthalenes are very scarce, even less is known about their electronic properties. A thorough literature search resulted in only one relevant publication, which, as we found, has never been cited outside Russian-language journals. Twenty-five years ago, Yagupolsky and coworkers showed that consecutive two, three, or four hydrogen substitutions (into 1, 4, 5 and/or 8 positions) with '$R_F$=$CF_3$ and/or —O—$CF_2$ groups in naphthalene lead to positive shifts in reduction potentials of 0.77, 1.16, and 1.44 V vs. naphthalene, respectively (Dunyashev et al., *Zhurnal Obshchei Khimii* 1988, 58, 200-202). This leads to an incremental shift of $E_{1/2}/n('R_F)$=0.29 V for 1,4,5,8-$NAPH('R_F)_n$, whereas a larger increment $E_{1/2}/n(R_F)$=0.37-0.38 V was determined in our study for 1,3,5,7-$NAPH(R_F)_4$ isomers.

TABLE 2.3

First reduction potentials $E_{1/2}$ (cyclic voltammetry) and peak potentials (square-wave voltammetry) for The $E_{1/2}^{0/-}$ of naphthalene and 1,3,5,7-$NAPH(R_F)_4$ compounds relative to $Fe(Cp_2)^{+/0}$ defined as 0.0 V.

| Compound | $E_{1/2}$, V | $1^{st}$ peak potential, V |
|---|---|---|
| NAPH | −3.08 | −3.05 |
| $NAPH(CF_3)_4$ | −1.62 | −1.64 |
| $NAPH(C_2F_5)_4$ | −1.63 | −1.59 |
| $NAPH(C_3F_7)_4$ | −1.55 | −1.56 |
| $NAPH(C_4F_9)_4$ | −1.56 | −1.56 |

Conclusions.

An efficient synthetic approach for the preparation of highly perfluoroalkylated naphthalenes that possess pronounced electron acceptor properties compared to underivatized naphthalene (which has a negative EA of −0.5 eV) was developed. A non-chromatographic isolation of the new four symmetric tetrakis-derivatives provides easy access to these new molecules for further studies. Additionally, we demonstrated applicability of the HPLC method developed earlier by us for separation of perfluoroalkyfullerenes, for the isolation of high-purity single isomers of $NAPH(C_2F_5)_{2,3}$. Creation of versatile libraries of novel naphthalene derivatives in the wide range of compositions, structures, and electrochemical properties that will serve as important building blocks and active components in biomedical, electronic, and materials studies is currently underway in our laboratories. This "tour-de force" approach to perfluoroalkylation of naphthalene organically complements existing elaborate and elegant solution chemistry, which is mostly focused on (and capable of) regioselective preparations of mono- and/or di-substituted perfluoroalkyl derivatives.

Experimental Section.

Perfluoroalkylation of Naphthalene.

A flame-dried reactor ampoule made out of Pyrex glass (40 mL internal volume) and equipped with a sealing neck and a 90-degree Teflon vacuum valve was charged with naphthalene (20 mg, 0.16 mmol). Eight equivalents of a perfluoroalkyl iodide reagent $R_FI$ was either measured using a PVT method and condensed into the liquid nitrogen-cooled reactor ampoule ($R_F$=$CF_3$, n-$C_2F_5$, gaseous reagents at room temperature), or measured using a 500 μL gas-tight syringe ($R_F$=n-$C_3F_7$, n-$C_4F_9$; liquid reagents at room temperature). The ampoule was cooled in liquid nitrogen and all non-condensable gases were evacuated, then the ampoule was flame-sealed and heated in a tube furnace at 300° C. for 3 hours; see Table 2.4. After heating, the ampoule was cooled to room temperature. Each of the experiments A-D (Table 2.4) was repeated at least twice, yielding practically identical product compositions (as determined by $^1H$ and $^{19}F$ NMR spectroscopy). Two batches of products underwent different work-up procedures, as described further below.

TABLE 2.4

Reaction conditions used for naphthalene perfluoroalkylation and mass of crude $NAPH(R_F)_n$ products.

| exp. | $R_FI$ reagent | reaction temperature, ° C. | reaction time, min | n(NAPH), mmol | n($R_FI$), mmol | m(crude product),[a] mg |
|---|---|---|---|---|---|---|
| A | $CF_3I$ | 300 | 180 | 0.157 | 1.36 | 70 |
| B | $C_2F_5I$ | 300 | 180 | 0.157 | 1.34 | 45 |
| C | 1-$C_3F_7I$ | 300 | 180 | 0.163 | 1.30 | 69 |
| D | 1-$C_4F_9I$ | 300 | 180 | 0.165 | 1.31 | 91 |

[a]The mass was determined upon concentrating the crude product mixture to dryness under a stream of air.

Crystallography.

The X-ray quality single crystals of 1,3,5,7-NAPH(CF$_3$)$_4$ and 1,3,5,7-NAPH(C$_2$F$_5$)$_4$ were grown by slow evaporation of their CS$_2$ and CDCl$_3$ solutions, respectively (at room temperature). Both compounds formed clear colorless crystals.

DFT Calculations.

Atomic coordinates of all studied molecules were first optimized at the PBE/TZ2P level using Priroda code then followed by B3LYP-D3/def2-TZVP computations performed using ORCA suite.

Abbreviations.

TGA, thermogravimetric analysis; NI-APCI, negative ion atmospheric pressure chemical ionization; PAH, polycyclic aromatic hydrocarbons; NAPH, naphthalene.

Experimental Details.

Reagents and Solvents.

Naphthalene (Sigma Aldrich, 99%), iodotrifluoromethane, iodopentafluoroethane, 1-iodoheptafluoropropane, 1-iodononafluorobutane (SynQuest Labs), sodium thiosulfate (Na$_2$S$_2$O$_3$, Fisher Scientific, ACS grade), tetrakis(dimethylamino)ethylene (TDAE, Sigma-Aldrich), chloroform-d (CDCl$_3$, Cambridge Isotopes), 1,4-bis-(trifluoromethyl)benzene (Sigma Aldrich), tetrabutylammonium tetrafluoroborate ((n-Bu)$_4$NBF$_4$, Sigma-Aldrich), dichloromethane (Fisher Scientific, ACS grade), carbon disulfide (Alfa Aesar, HPLC grade), acetonitrile (Fisher Scientific, ACS grade), acetone (technical grade) were used as received. Deionized distilled water was purified by a Barnstead NANOpure Ultrapure Water system (final resistance 18 MΩ). Dimethoxyethane (Sigma-Aldrich, distilled from CaH$_2$ under nitrogen atmosphere), ferrocene (Acros Organics, 98%), and tetrabutylammonium perchlorate (Sigma-Aldrich, dried at 80° C. under dynamic vacuum for 24 hours) were used for electrochemical measurements.

Instrumentation.

HPLC analysis and separation were carried on a Shimadzu instrument (composed of Shimadzu LC-6AD pump, a Shimadzu UV detector SPD-20A set for 300 nm detection wavelength, and a communication bus module Shimadzu CBM-20A). The instrument was equipped with a FluoroFlash column (Fluorous Technologies, Inc., PF-C8, 5 µm); 90/10 v/v mixture of acetonitrile/water was used as the eluent at a flow rate of 2 mL·min$^{-1}$.

Proton (400 MHz) and fluorine-19 (376 MHz) NMR spectra were recorded on a Varian INOVA instrument in CDCl$_3$ solution using 1,4-bis-(trifluoromethyl)benzene ($\delta$($^{19}$F)=−66.35; $\delta$($^1$H)=7.77) as the internal standard.

Negative-mode atmospheric pressure chemical ionization mass spectrometry analysis was performed on a 2000 Finnigan LCQ-DUO mass-spectrometer using CH$_3$CN carrier solvent at 0.3 mL·min$^{-1}$ flow rate. The samples were dissolved in dry deoxygenated acetonitrile in a nitrogen-atmosphere glovebox and treated with a small amount (1-2 drops) of tetrakis(dimethylamino)ethylene solution in acetonitrile in order to generate negative ions (a few drops of TDAE solution were added to the samples which changed color from colorless to pale-yellow).

Cyclic voltammetry measurements were carried out on a PAR 263 potentiostat/galvanostat using an electrochemical cell equipped with platinum counter and working electrodes (0.125 mm diameter) and a silver reference electrode (0.5 mm diameter). The samples were dissolved in a 0.1 M TBAClO$_4$ solution in dimethoxyethane; the cyclic voltammetry was performed at 500 mV·s$^{-1}$ scan rate, unless otherwise indicated, and referenced versus ferrocene internal standard.

Melting points were determined using a Laboratory Devices MeI-Temp instrument with a mercury thermometer (−10° C.±260° C.±0.1° C.) and a heating rate of ca. 1-2° C./min; all samples were sealed in 1.0×90 mm melt point capillary tubes. Sublimation rate studies were performed using TA Instruments Series-2950 instrumentation. Prior to each TGA experiment, the platinum pan was rinsed with ethyl alcohol and flamed three times (until dull red glow). Upon sample loading, care was taken to distribute the sample evenly over the aluminum pan surface. During the sublimation rate experiments, TGA temperatures were set at 25.00° C. and held isothermally throughout the experiment.

The X-ray crystallography data were collected using a Bruker Kappa APEX II CCD diffractometer employing Mo Kα radiation and a graphite monochromator. Unit cell parameters were obtained from least-squares fits to the angular coordinates of all reflections, and intensities were integrated from a series of frames (ψ and φ rotation) covering more than a hemisphere of reciprocal space. Absorption and other corrections were applied using SCALE (G. M. Sheldrick, SADABS, v. 2.10—a program for area detector absorption corrections, Bruker AXS, Madison, Wis., 2003). The structures were solved using direct methods and refined (on F$^2$, using all data) by a full-matrix, weighted least-squares process. Standard Bruker control and integration software (APEX II) was employed (G. M. Sheldrick, Crystallography Program APEX2, v. 2.0-2, Bruker AXS, Madison, Wis., 2006), and Bruker SHELXTL software was used for structure solution, refinement, and molecular graphics (G. M. Sheldrick, Crystallography Software Package SHELXTL, v. 6.12 UNIX, Bruker AXS, Madison, Wis., 2001.).

NMR Determination of Mol % Yield of NAPH(R$_F$)$_n$ and the Average Number of R$_F$ Groups Per Naphthalene Core (n(R$_F$)).

The ampoules containing products A-D were cooled in acetone/dry ice bath, cut open under air, and quickly evacuated to remove the highly volatile R$_F$I, R$_F$H, and (R$_F$)$_2$ components. Then the ampoules were allowed to warm up, the crude products were dissolved in 3-5 mL of CDCl$_3$, and the resulting solutions were washed with aqueous a 1M Na$_2$S$_2$O$_3$ solution to remove 12 (only trace amounts of insoluble black carbonaceous materials were present in each product). The organic layer (bottom layer) was extracted and the solvent was quickly evaporated under a stream of dry air. Despite the great care taken to limit the losses of the NAPH(R$_F$)$_n$ products due to evaporation at this step, it is virtually certain that some losses were incurred. The resulting dry products were dissolved in 3.0 mL of 5.3 mM solution of (n-Bu)$_4$NBF$_4$ in CDCl$_3$. 750 µL aliquots of these solutions were analyzed by $^1$H and $^{19}$F NMR spectroscopy using the following acquisition parameters:

$^{19}$F NMR: 25 s relaxation delay, 45° flip angle, acquisition time=2.000 s, 32 scans $^1$H NMR: 25 s relaxation delay, 45° flip angle, acquisition time=2.556 s, 32 scans Using the integrated intensity of $^1$H and $^{19}$F NMR peaks due to (n-Bu)$_4$NBF$_4$ standard and NAPH(R$_F$)$_n$ products, the molar concentration of aromatic protons and the molar concentration of R$_F$ groups of NAPH(R$_F$)$_n$ were calculated. The total number of R$_F$ groups and aromatic protons in any NAPH (R$_F$)$_n$ product is equal to eight; therefore, the combined molar concentration of all NAPH(R$_F$)$_n$ products is equal to the sum of the molar concentration of aromatic protons and the molar concentration of R$_F$ groups divided by eight, which allows to calculate the total number of moles of NAPH(R$_F$)$_n$ products. It is notable that no traces of unreacted naphthalene were observed in the products A-D by $^1$H NMR spectroscopy.

Isolation of NAPH($R_F$)$_4$ Products.

Separate batches of crude materials prepared under conditions A-D (see Table 2.4) were used to isolate isomerically pure NAPH($R_F$)$_4$ materials. In all cases the ampoules were open under air, the products were dissolved in 3-5 mL of dichloromethane, and the resulting solutions were washed with 1 M aqueous solution of $Na_2S_2O_3$ to remove $I_2$. The resulting solution was rapidly concentrated to dryness under a flow of dry air.

NAPH($CF_3$)$_4$.

The concentrated crude material resulting from experiment A (see Table 2.4) was dissolved in ca. 2 mL of 90/10 (v/v) acetonitrile/water mixture; NAPH($CF_3$)$_4$ precipitated out and was filtered through a pipette with a plug made of a glass microfiber filter. The filter was washed with ca. 1 mL of 90/10 (v/v) acetonitrile/water mixture; then the purified NAPH($CF_3$)$_4$ was dissolved in $CDCl_3$ and analyzed by $^1$H and $^{19}$F NMR spectroscopy, and NI-APCI mass spectroscopy which demonstrated 95+% molar purity, see below.

NAPH($C_2F_5$)$_4$.

The concentrated crude material resulting from experiment B (see Table 2.4) was washed several times with 50-100 μL of dichloromethane. The remaining white $CH_2Cl_2$-insoluble material was dissolved in $CDCl_3$ and analyzed by $^{19}$F and $^1$H NMR spectroscopy, HPLC analysis, and APCI mass spectrometry which showed it to be 95+% pure NAPH($C_2F_5$)$_4$, see below.

NAPH(n-$C_3F_7$)$_4$.

The concentrated crude material resulting from experiment C (see Table 2.4) was mixed with 500-1000 μL of absolute ethanol. A system with two immiscible liquid layers was formed; the yellow oil blob was separated and concentrated to dryness under the flow of dry air. The resulting yellow solid was washed three times with 250-500 μL of dichloromethane leaving behind a white insoluble material. This material was dissolved in $CDCl_3$ and analyzed by $^{19}$F and $^1$H NMR spectroscopy, and APCI mass spectrometry which showed it to be 95+% pure NAPH(n-$C_3F_7$)$_4$, see below.

NAPH(n-$C_4F_9$)$_4$.

The concentrated crude material resulting from experiment D (see Table 2.4) was diluted with 1-2 mL of dichloromethane and filtered through a pipette with a plug made of a glass microfiber filter. The insoluble material was washed twice with a minimum amount of dichloromethane; then it was dissolved in ca. 4 mL of $CDCl_3$. The solution was analyzed with $^{19}$F and $^1$H NMR spectroscopy, and NI-APCI mass spectrometry which showed that it contained 95+% pure NAPH(n-$C_4F_9$)$_4$, see Table 2.5 below.

TABLE 2.5

Concentrations of $R_F$ and hydrogen substituents for NAPH($R_F$)$_n$ solutions and molar yields of NAPH($R_F$)$_n$ products.

| exp. | $R_F$ | [$R_F$], mM | [H], mM | n(NAPH($R_F$)$_n$), μmol | yield of NAPH($R_F$)$_n$,[a] mol % |
|---|---|---|---|---|---|
| A | $CF_3$ | 98 | 230 | 123 | 79 ± 15 |
| B | $C_2F_5$ | 87 | 210 | 111 | 70 ± 15 |
| C | n-$C_3F_7$ | 95 | 310 | 152 | 95 ± 10 |
| D | n-$C_4F_9$ | 100 | 310 | 154 | 96 ± 10 |

[a]160 μmol of naphthalene starting material was used for each perfluoroalkylation experiment.

Example 3

Poly(Trifluoromethyl)Azulenes: Structures and Acceptor Properties

Six new poly(trifluoromethyl)azulenes prepared in a single high-temperature reaction exhibit strong electron accepting properties in the gas phase and in solution and demonstrate propensity to form regular π-stacked columns in the donor-acceptor crystals, when mixed with pyrene as a donor.

Azulene is a non-alternant, non-benzenoid aromatic hydrocarbon with an intense blue colour, a dipole moment of 1.0 D, positive electron affinity, and an "anomalous" emission from the second excited state in violation of Kasha's rule. Azulene's unique properties have potential uses in molecular switches, molecular diodes, organic photovoltaics, and charge transfer complexes. Introduction of electron-withdrawing groups to the azulenic core, such as CN, halogens, and $CF_3$, can enhance certain electrical and photophysical properties.

In this work, we report six new trifluoromethyl derivatives of azulene (AZUL), three isomers of AZUL($CF_3$)$_3$ and three isomers of AZUL($CF_3$)$_4$, and the first X-ray structure of a π-stacked donor-acceptor complex of a trifluoromethyl azulene with donor pyrene.

In sharp contrast to the commonly applied multi-step solution-based methods of hydrogen substitutions in AZUL with electron withdrawing groups such as CN or Hal, in this work, we prepared all AZUL($CF_3$)$_n$ compounds in a rapid single-step reaction carried out in the gas phase. Azulene and $CF_3I$ gas were loaded into a sealed glass ampoule and heated in a furnace to 300° C. for 15 minutes to produce mostly a mixture of azulene($CF_3$)$_n$ (n=3-5), as shown by negative-ion atmospheric-pressure chemical ionization mass spectrometry (APCI-MS). The crude reaction mixture also contained small amounts of $C_{10}H_2(CF_3)_6$, and dimers ($C_{20}H_{16-(n+1)}(CF_3)_{n=7,8,9}$). Formation of the thermally stable dimeric AZUL species in such high-temperature reactions has not been previously reported and deserves further studies, particularly due to the relatively high electrical conductivity observed for polymeric AZUL$_n$. Doubling the reaction time resulted in more selective formation of AZUL-5-1 (see Kuvychko et al., Angew. Chem. Int. Ed. Engl., 2013, 52, 4871-4874).

The crude reaction mixture of the 15-minute reaction was separated by HPLC, yielding seven pure AZUL($CF_3$)$_n$ derivatives, i.e., three isomers of AZUL($CF_3$)$_3$, three isomers of AZUL($CF_3$)$_4$ and one isomer of AZUL($CF_3$)$_5$ (for isomer notations see Scheme 3.1).

Scheme 3.1. Synthesis of AZUL($CF_3$)$_{3-5}$.

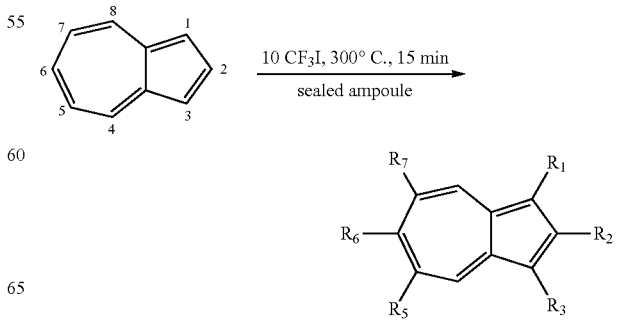

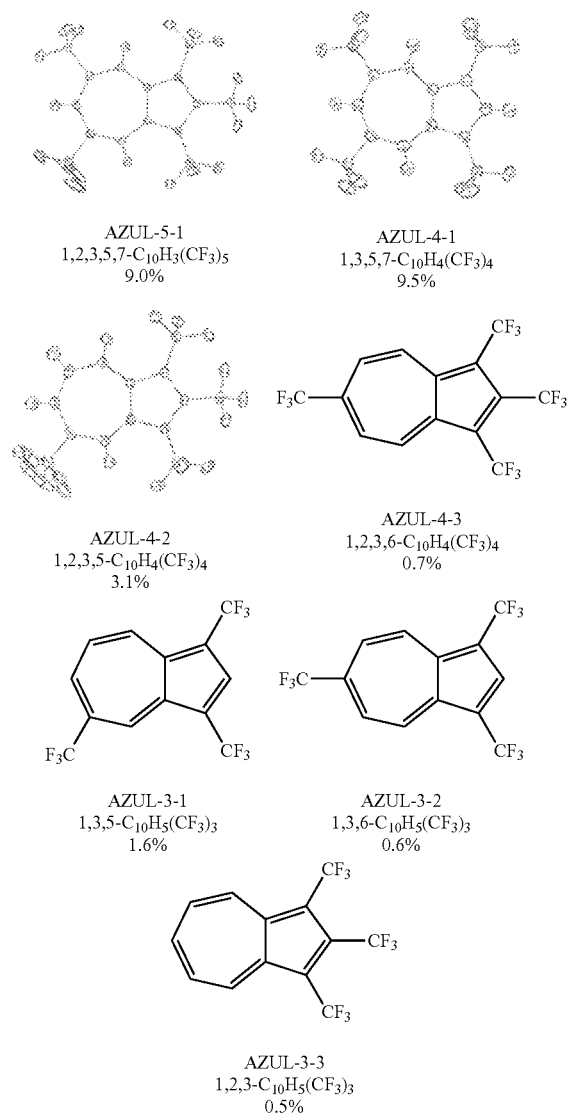

Abbreviations, full names, and isolated yields are given. The X-ray structures of AZUL-5-1, AZUL-4-1, AZUL-4-2, are shown with thermal ellipsoids at the 50% probability level. Overall isolated yield=25%.

Figure 17:
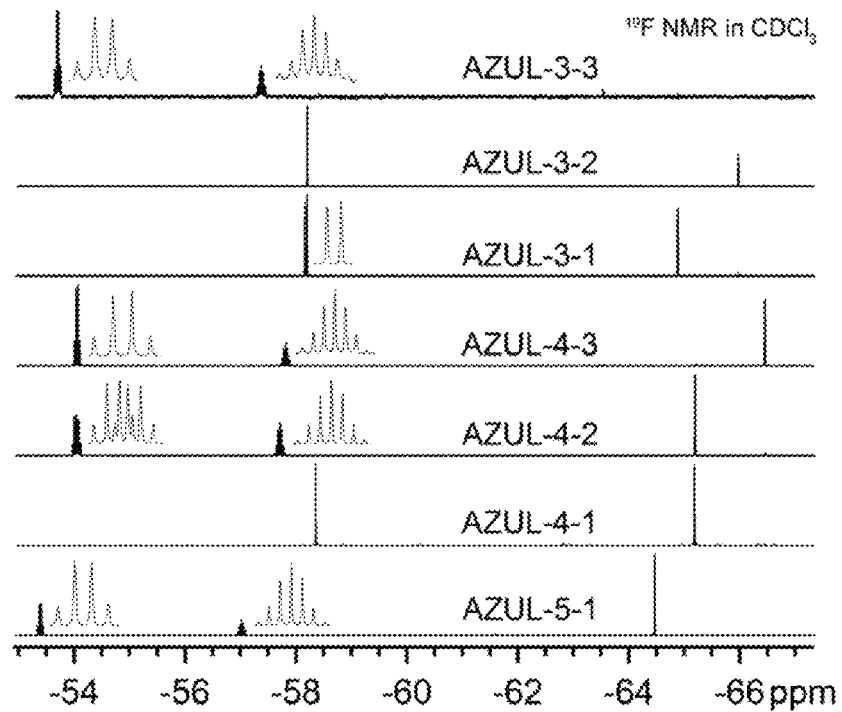
FIG. 17. $^{19}$F NMR spectra (CDCl$_3$, 376.5 MHz, δ(C$_6$F$_6$)=−164.9 ppm) showing the CF$_3$ multiplets and singlets of the seven azulene derivatives. Regions where peaks are in close proximity are shown as insets for clarity.
Figure 18:
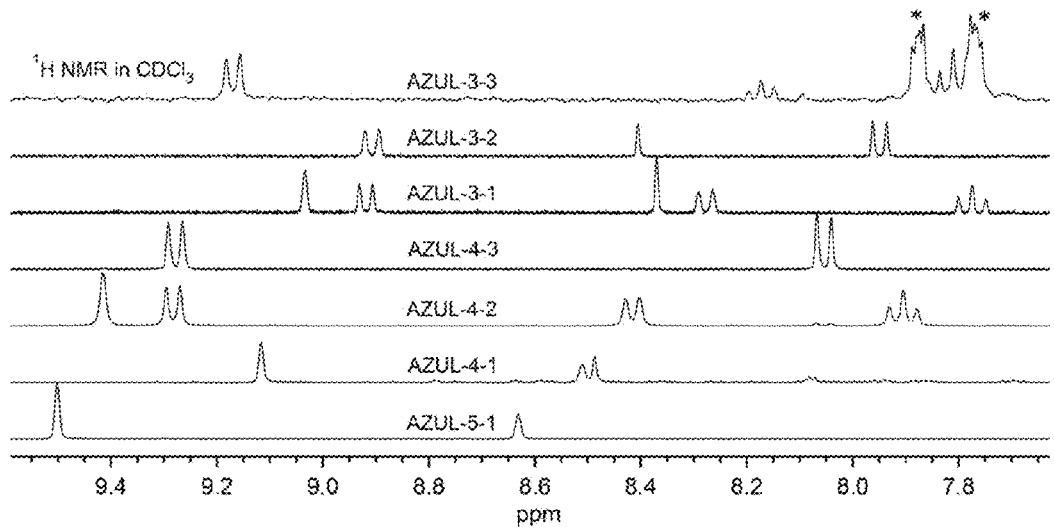
FIG. 18. $^1$H NMR of the seven azulene derivatives in CDCl$_3$. *=an impurity in AZUL-3-3 spectrum.

Structural assignments for the new compounds were done based on negative-ion APCI-MS and the $^1$H NMR and $^{19}$F NMR spectral analysis (see FIG. 17 and FIG. 18). The $^{19}$F NMR spectra were obtained in CDCl$_3$ and are shown in FIG. 17. Multiplets corresponding to each CF$_3$ group appear in two distinct regions consistent to whether they are bonded to the five-membered ring (between −53.5 and −58.5 ppm) or the seven-membered ring of azulene (between −64.4 and −66.5 ppm). Through-space F—F coupling is observed between CF$_3$ groups bonded to adjacent carbon atoms of the azulene core resulting in quartets and apparent septets and no F—H coupling is observed. In some cases, CF$_3$ groups occupy all three carbon atoms of the five-membered ring, whereas CF$_3$ groups bonded to adjacent carbon atoms of the seven-membered ring were not observed.

The structures of the two most abundant AZUL(CF$_3$)$_4$ isomers, AZUL-4-1 and AZUL-4-2 were confirmed by single-crystal X-ray diffraction (Scheme 3.1); the crystals were grown by slow evaporation from dichloromethane and hexane solutions, respectively. AZUL-4-1 crystallizes in the P-1 space group with three molecules per unit cell. One molecule is ordered while the other two molecules are disordered, adopting opposite orientations at a given site. This disorder is typical and has been observed for azulene and azulene derivatives. Disorder in the azulene core is not observed in the structure of AZUL-4-2; however, the fluorine atoms of the CF$_3$ group attached to C5 are disordered around the attached carbon atom.

The UV-vis absorption spectra of the seven poly(trifluoromethyl)azulene derivatives were obtained in hexanes and dichloromethane. Unlike azulene, where the S$_1$ states become more refined in hexanes vs. dichloromethane, the solvent choice had little or no effect on the absorption spectra of the trifluoromethyl derivatives. Theoretical and experimental studies by Liu et. al. showed that electron withdrawing groups on odd-numbered carbon atoms blue-shift the 51 maxima by lowering the HOMO energy while the LUMO energy remains relatively unchanged (Shevyakov, et al., *J. Phys. Chem. A*, 2003, 107, 3295-3299).

Indeed, the absorption maxima in the 51 band for all seven of the trifluoromethyl azulenes are blue shifted by 26-57 nm (see Table 3.1). All seven derivatives have CF$_3$ substituents at the C1 and C3 positions which plays a large part in blue-shifting the maxima. Two compounds (AZUL-3-2 and AZUL-4-3) have a CF$_3$ group bonded to an even-numbered C6 atom, which would likely cause a smaller blue shifts (26 and 27 nm), and is in agreement with the earlier prediction that electron withdrawing groups on even-numbered carbon atoms lower the LUMO energy. Electron withdrawing groups should lower the HOMO and LUMO+1 energy by nearly the same amount since the electron distributions of the HOMO and LUMO+1 are virtually identical, so shifts in the absorption maxima in the S$_2$ region are not expected to be as pronounced as the S$_1$ region. Absorption maxima shifts in the S$_2$ region are, in fact, very minor and even slightly red-shifted for one compound, AZUL-4-1.

TABLE 3.1

Absorption maxima for AZUL derivatives in hexanes (nm).

| Compound | $\lambda_{max}(S_0-S_2)$ | $\Delta\lambda_{max}$ | $\lambda_{max}(S_0-S_1)$ | $\Delta\lambda_{max}$ |
|---|---|---|---|---|
| AZUL | 341 | | 579 | |
| AZUL-3-1 | 338 | −3 | 532 | −47 |
| AZUL-3-2 | 334 | −7 | 553 | −26 |
| AZUL-3-3 | 329 | −12 | 522 | −57 |
| AZUL-4-1 | 342 | +1 | 537 | −42 |
| AZUL-4-2 | 334 | −7 | 531 | −48 |
| AZUL-4-3 | 332 | −9 | 552 | −27 |
| AZUL-5-1 | 338 | −3 | 536 | −43 |

Figure 19:
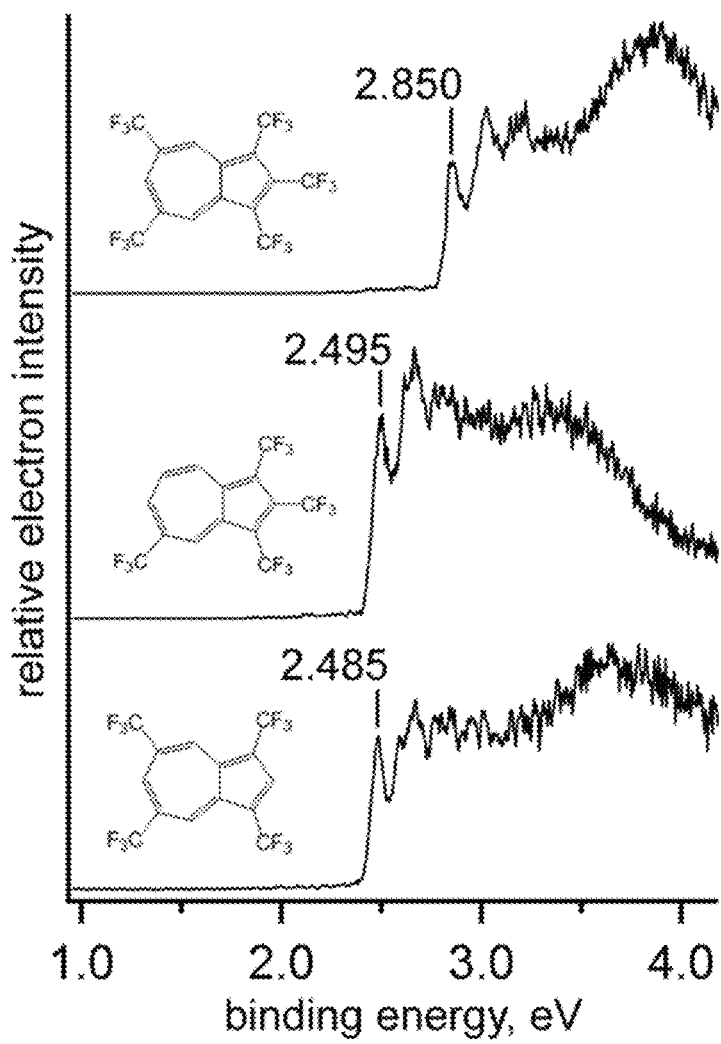
FIG. 19. The low-temperature (12 K) photoelectron spectrum at 266 nm of AZUL-5-1 (top), AZUL-4-2 (middle), and AZUL-4-1 (bottom).

The gas-phase electron affinity (EA) was measured experimentally by low-temperature photoelectron spectroscopy for two new isomers of AZUL-4 and compared to electron affinity of the parent AZUL, 0.790(8), and AZUL-5-1, 2.850(15) (FIG. 19).

Two AZUL(CF$_3$)$_4$ isomers exhibit very close EA values, 2.495(10) and 2.485(10). A plot of EA vs. number of CF$_3$ groups reveals a remarkable linear correlation, with a slope of 0.42 eV per CF$_3$ group. An extrapolation to AZUL-6 (that was observed by mass-spectrometry in the crude product as noted above) yields an estimated EA value of 3.3 eV.

No experimental data are available in the literature on EA values for any azulene derivatives for comparison. The electrochemical potentials in solution were reported for some derivatives. Coincidentally, a similar linear correlation with nearly the same slope was observed in the half-wave reduction potentials of a series of cyano azulenes, $AZUL(CN)_{2-4}$, where the $E_{1/2}(0/-)$ became more positive by 0.42 V per one CN substitution. Cyclic voltammetry in DME using TBAP electrolyte has been performed in this work for the most abundant compounds, and reversible electrochemical behaviour was only observed in the case of AZUL-4-1, $E_{1/2}(0/-)$ =−1.05 V vs. $FeCp_2(+/0)$. Comparison with the reduction potentials of $AZUL(CN)_4$ shows the latter to be a stronger acceptor in solution than $AZUL(CF_3)_4$, in agreement with the theoretical predictions reported earlier for other polycyclic aromatic molecules, including our recent work on the substituted corannulene derivatives.

Figure 20:
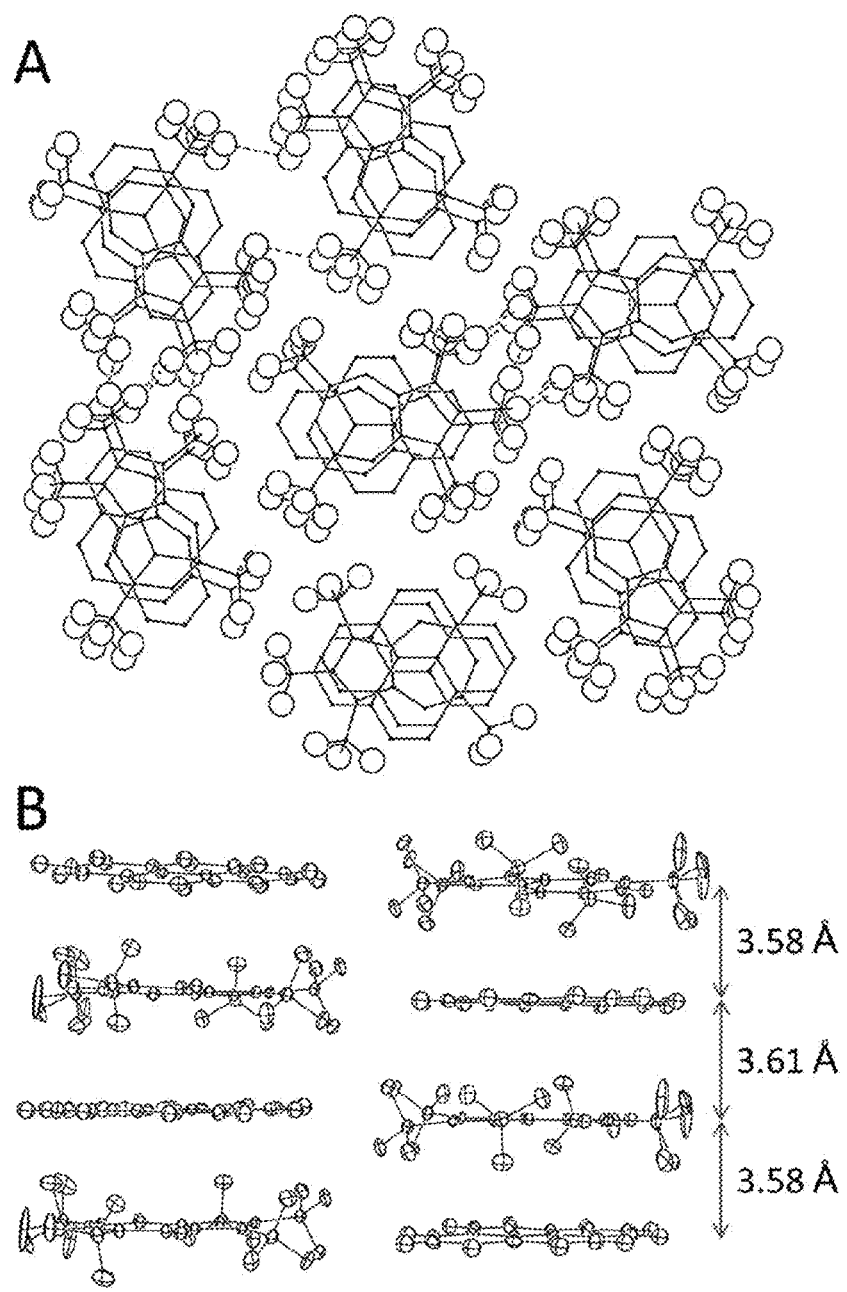
FIG. 20. Showing the packing of AZUL-5-1/pyrene columns from the top down (A) and a view of two columns from the side (B). Distances between AZUL-5-1 core plane and pyrene core planes are given.
Figure 21:
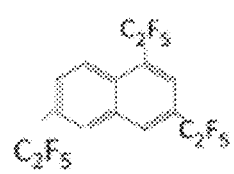
FIG. 21. Compounds of the invention and related data, according to various embodiments.
Figure 21:
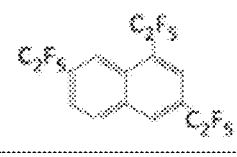
Figure 21:
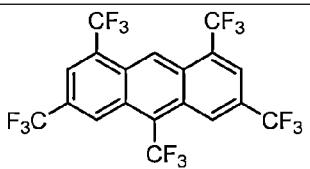
Figure 21:
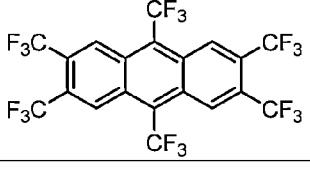
Figure 21:
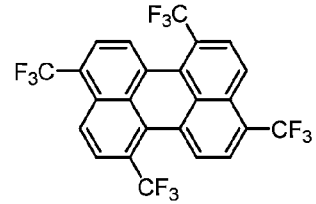
Figure 21:
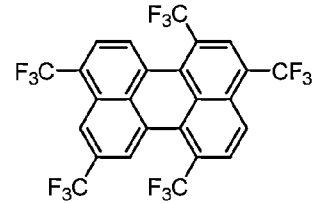
Figure 21:
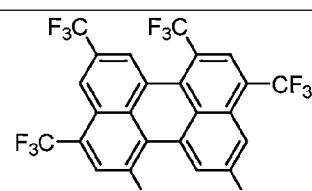
Figure 21:
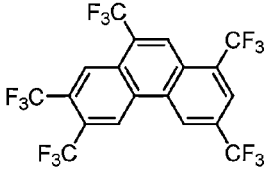
Figure 21:
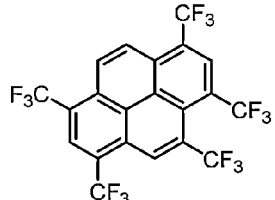
Figure 21:
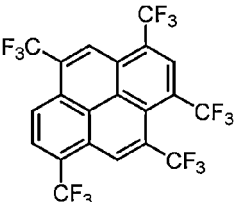
Figure 21:
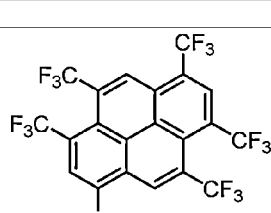
Figure 21:
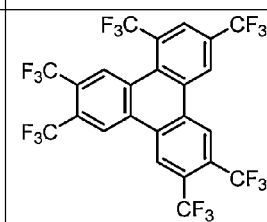
Figure 21:
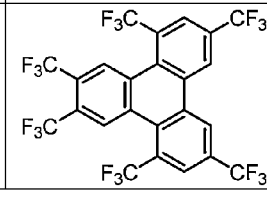

Varying the degree of substitution allows for the selection of an azulene derivative to match with a proper donor to form a charge transfer complex. The increased EA of AZUL-5-1 was utilized to form a charge transfer complex with pyrene as the donor molecule. Dark red-purple crystalline rods of the charge-transfer complex between AZUL-5-1 and pyrene were grown by the slow evaporation from a dichloromethane solution at 2° C. Columns of alternating AZUL-5-1 and pyrene were formed in a pseudo hexagonal close-packed formation (FIG. 20A) with intermolecular, donor-acceptor distances of 3.58 and 3.61 Å (FIG. 20B). The charge-transfer between AZUL-5-1 and pyrene possibly prevents AZUL-5-1 from adopting opposite orientations within its position and there was no disorder observed in the azulene core as was observed in the structure of AZUL-4-1. Solutions with varying amounts of AZUL-5-1:pyrene were made in DCM. All solutions remained the deep purple colour of AZUL-5-1 and no new absorption bands were observed in UV-vis absorption measurements at different concentrations, even when AZUL-5-1:pyrene=50:50 (the same ratio that formed the single-crystal charge-transfer complex). The absence of charge-transfer bands has also been observed with other azulene charge-transfer complexes, but charge-transfer bands from pyrene have been observed in other pyrene/oligomer complexes.

In conclusion, we have developed an efficient trifluoromethylation method for azulene that yields a mixture of seven readily separable poly(trifluoromethyl)azulenes has been developed. Low-temperature photoelectron spectroscopy revealed a linear increase in gas-phase electron affinity of 0.42 eV per $CF_3$ group. Strong acceptor properties of the new compounds were utilized in the first example of a charge-transfer complex with pyrene that exhibits a regular columnar packing and strong pi-pi interactions between the aromatic cores of the donor and acceptor. Further elucidating oligomeric poly(trifluoromethyl)azulene and $AZUL(CF_3)_6$ species will result in even stronger electron acceptors and could lead to charge-transfer complexes with unique packing motifs and unusual electronic properties.

Experimental Section.
General Information.

All reagents and solvents were reagent grade or better. ACS Grade dichloromethane (Fisher Scientific), HPLC Grade acetonitrile (Fisher Scientific), ACS Grade hexanes (Fisher Scientific), sodium thiosulfate crystals (Mallinckrodt), trifluoromethyl iodide (Synquest Labs), Chloroform-D (Cambridge Isotopes Laboratories), and hexafluorobenzene (Oakwood Products) were used as received. HPLC analysis and separation was done using Shimadzu liquid chromatography instrument (CBM-20A control module, SPDA UV detector set to 300 or 275 nm detection wavelength, LC-6AD pump, manual injector valve) equipped with semi-preparative 10 mm I.D.×250 nm Cosmosil Buckyprep column (Nacalai Tesque, Inc.) or analytical 4.6 mm I.D.×150 nm FluoroFlash PF-C8 100 Å 5 µm column (Fluorous Technologies, Inc.). The atmospheric-pressure chemical ionization (APCI) mass spectra were recorded on 2000 Finnigan LCQ-DUO mass-spectrometer (acetonitrile carrier solvent, 0.3 mL·min$^{-1}$ flow rate, analyte samples injected as solutions in dichloromethane or acetonitrile).

All NMR spectra were recorded on Varian INOVA 400 instrument in $CDCl_3$ solution. The $^1H$ and $^{19}F$ frequencies were 400 and 376 MHz, respectively. The $^{19}F$ chemical shifts were determined using hexafluorobenzene as an internal standard (δ −164.9). The $^1H$ chemical shifts were determined using the resonance of the residual $CHCl_3$ in $CDCl_3$ as an internal standard (δ 7.26). UV-Vis absorption spectra were recorded by using a Cary 500 spectrophotometer with a resolution of 1 nm. Cyclic voltammetry measurements were carried out on PAR 263 potentiostat/galvanostat in anaerobic conditions using 0.1 M $N(nBu)_4ClO_4$ in dimethoxyethane; platinum working and counter electrodes; silver wire quasi-reference electrode; 500 mVs$^{-1}$; ferrocene internal standard. X-ray diffraction data for a single crystal of AZUL-4-1 were recorded by using a Bruker Kappa APEX II CCD diffractometer at Colorado State University.

Trifluoromethylation of Azulene:

$Azulene(CF_3)_n$ was prepared according the procedure of Example 1, modified as follows. Azulene (50 mg, 0.39 mmol, blue solid) was placed into a glass ampoule (327 mL) and the ampoule was cooled with liquid nitrogen and evacuated using a vacuum line equipped with a pressure gauge and a calibrated volume (51.7 mL). Using the calibrated volume and pressure gauge, $CF_3I$ gas was measured (11.7 mmol, 30 equiv.), and then the measured $CF_3I$ gas was condensed into the cooled ampoule containing azulene. The ampoule was then flame-sealed and warmed to room temperature. The sealed ampoule was then placed in a heating furnace and heated at 10° C. min$^{-1}$ to 300° C. When the formation of purple iodine gas was observed at 285° C., the ampoule was heated for another 15 minutes up to 300° C. before cooling to room temperature.

After cooling to room temperature, the ampoule was cooled in liquid nitrogen and opened (lower than ambient pressure inside). Excess $CF_3I$ gas was boiled off upon warming to room temperature and then the soluble products were dissolved in dichloromethane. The purple dichloromethane solution was washed twice with a saturated sodium thiosulfate solution (aq) to remove $I_2$ until color was no longer observed in the aqueous layer. The dichloromethane was removed by rotary evaporation and the remaining solid was dissolved and filtered in acetonitrile (purple solution) for HPLC separation as described below. Care must be taken when rotary evaporating the crude mixture because some of the products are rather volatile. Total conversion of azulene to isolated products=25 mol %.

HPLC Purifications of $Azulene(CF_3)_n$.

The first HPLC separation of the $azulene(CF_3)_n$ crude samples was done using semi-preparative Cosmosil Buckyprep HPLC column, acetonitrile eluent, flow rate of 5.0 mL·min$^{-1}$, 300 nm detection. Three different fractions 4.3-5.0 min (I), 5.0-5.8 min (II), and 5.9-6.7 min (III) were isolated for further separation using analytical FluoroFlash column, flow rate of 2.0 mL·min$^{-1}$. Second stage separation of I (acetonitrile/$H_2O$=90:10, 300 nm detection) resulted in two more fractions: 3.4-5 min. (IV) and 5.9-7.3 min (AZUL-4-1). Fraction IV was further separated (acetonitrile/$H_2O$=60:40, 275 nm detection) and resulted in two fractions: 20-21.6 min (AZUL-3-2) and 21.6-24.0 min (AZUL-3-1). Second stage separation of II (acetonitrile/$H_2O$=80:20, 275 nm detection) resulted in one predominant fraction collected from 4.0-6.4 min (AZUL-3-3). Second stage separation of III (acetonitrile/ $H_2O$=95:5, 300 nm detection) resulted in two more fractions: 3.3-4.6 min (V) and 4.6-6.0 min (AZUL-5-1). Fraction V was further separated (acetonitrile/$H_2O$=80:20, 300 nm detection) and resulted in two fractions: 6.8-7.8 min (AZUL-4-3) and 7.8-9.4 min (AZUL-4-2). The solvent was then removed from the compounds as described below along with further characterization.

AZUL-5-1, 1,2,3,5,7-azulene($CF_3$)$_5$.

The solvent was removed by rotary evaporation and the purple solid was collected with dichloromethane. Co-crystals of AZUL-5-1/pyrene (dark red-purple rods) were grown from the slow evaporation of a dichloromethane solution (AZUL-5-1:pyrene=1:1) at 2° C. 16.6 mg, 9.0 mol % yield based on azulene. $^{19}$F NMR: δ −54.35 (q, J=12.3 Hz, 2$CF_3$, $CF_3^{1,3}$); −58.02 (sept, J=12.0 Hz, 1$CF_3$, C2); −65.46 (s, 2$CF_3$, $CF_3^{5,7}$). $^1$H NMR: δ 9.50 (s, 2H, $H^{4,8}$); 8.63 (s, 1H, $H^6$). NI-APCI mass spec: 468.41 m/z. Calc. 468.00.

AZUL-4-1, 1,3,5,7-azulene($CF_3$)$_4$.

The majority of the solvent was carefully removed by fractional distillation until a concentrated purple solution remained. Dichloromethane was then added to the purple solution and all of the solvent was dried down in air to give AZUL-4-1 as a purple solid. Single crystals (purple plates) were grown by the slow evaporation from a dichloromethane solution. 14.7 mg, 9.5 mol % yield based on azulene. $^{19}$F NMR: δ −58.41 (s, 2$CF_3$, $CF_3^{1,3}$); −65.19 (s, 2$CF_3$, $CF_3^{5,7}$). $^1$H NMR: δ 9.12 (s, 2H, $H^{4,8}$); 8.51 (s, 1H, $H^{2\ or\ 6}$); 8.49 (s, 1H, $H^{2\ or\ 6}$). NI-APCI mass spec: 400.40 m/z. Calc.: 400.01.

AZUL-4-2, 1,2,3,5-azulene($CF_3$)$_4$.

The solvent was rotary evaporated and the purple solid was collected in dichloromethane. Single crystals (thin purple plates) were grown by the slow evaporation from a dichloromethane solution. 4.6 mg, 3.1 mol % yield based on azulene. $^{19}$F NMR: δ −54.02 (q, J=12.3 Hz, 1$CF_3$, $CF_3^{1\ or\ 3}$); −54.07 (q, J=11.8 Hz, 1$CF_3$, $CF_3^{1\ or\ 3}$); −57.71 (sept, J=12.0 Hz, 1$CF_3$, $CF_3^2$); −65.20 (s, 1$CF_3$, $CF_3^5$). $^1$H NMR: δ 9.41 (s, 1H, $H^4$); 9.28 (d, $^3J_{HH}$=10.6 Hz, 1H, $H^8$); 8.41 (d, $^3J_{HH}$=10.6 Hz, 1H, $H^6$); 7.90 (t, $^3J_{HH}$=10.4 Hz, 1H, $H^7$). NI-APCI mass spec: 400.40 m/z. Calc.: 400.01.

AZUL-4-3, 1,2,3,6-azulene($CF_3$)$_4$.

The solvent was rotary evaporated and a purple solid was collected in dichloromethane. 1.1 mg, 0.7 mol % yield based on azulene. $^{19}$F NMR: δ −54.06 (q, J=11.8 Hz, 2$CF_3$, $CF_3^{1,3}$); −57.82 (sept, J=12.0 Hz, 1$CF_3$, $CF_3^2$); −66.46 (s, 1$CF_3$, $CF_3^6$). $^1$H NMR: δ 9.28 (d, $^3J_{HH}$=11 Hz, 2H, $H^{4,8}$); 8.05 (d, $^3J_{HH}$=11 Hz, 2H, $H^{5,7}$). NI-APCI mass spec: 400.40 m/z. Calc.: 400.01.

AZUL-3-1, 1,3,5-azulene($CF_3$)$_3$.

The solvent could not be simply rotary evaporated due to the volatility of the product. The product was precipitated by the addition of $H_2O$ and cooling, filtered through glass microfibre, and the purple solid was collected with a mixture of dichloromethane and acetonitrile. 2.1 mg, 1.6 mol % yield based on azulene. $^{19}$F NMR: δ −58.17 (s, 1$CF_3$, $CF_3^{1,3}$); −58.21 (s, 1$CF_3$, $CF_3^{1,3}$); −64.89 (s, 1$CF_3$, $CF_3^5$). $^1$H NMR: δ 9.03 (s, 1H, $H^4$); 8.91 (d, $^3J_{HH}$=9.8 Hz, 1H, $H^8$); 8.37 (s, 1H, $H^2$); 8.27 (d, $^3J_{HH}$=10.6 Hz, 1H, $H^6$); 7.77 (t, $^3J_{HH}$=10.4 Hz, 1H, $H^7$). NI-APCI mass spec: 332.40 m/z. calc.: 332.02.

AZUL-3-2, 1,3,6-azulene($CF_3$)$_3$.

The solvent could not be simply rotary evaporated due to the volatility of the product. The product was precipitated by the addition of $H_2O$ and cooling, filtered through glass microfibre, and the purple solid was collected with dichloromethane. 0.8 mg, 0.6 mol % yield based on azulene. $^{19}$F NMR: δ −58.21 (s, 2$CF_3$, $CF_3^{1,3}$); −65.98 (s, 1$CF_3$, $CF_3^6$). $^1$H NMR: δ 8.90 (d, $^3J_{HH}$=10.2 Hz, 2H, $H^{4,8}$); 8.40 (s, 1H, $H^2$); 7.95 (d, $^3J_{HH}$=11 Hz, 2H, $H^{5,7}$). NI-APCI mass spec: 332.40 m/z. calc.: 332.02.

AZUL-3-3, 1,2,3-azulene($CF_3$)$_3$.

The solvent could not be simply rotary evaporated due to the volatility of the product. The product was precipitated by the addition of $H_2O$ and cooling, filtered through glass microfibre, and the pink solid was collected with dichloromethane. 0.7 mg, 0.5 mol % yield based on azulene. $^{19}$F NMR: δ −53.71 (q, J=11.8 Hz, 2$CF_3$, $CF_3^{1,3}$); −57.38 (sept, J=12.0, 1$CF_3$, $CF_3^2$). $^1$H NMR: δ 9.17 (d, $^3J_{HH}$=10.2 Hz, 2H, $H^{4,8}$); 8.17 (t, $^3J_{HH}$=10.0 Hz, 1H, $H^6$); 7.81 (t, $^3J_{HH}$=10.4 Hz, 2H, $H^{5,7}$). NI-APCI mass spec: 332.27 m/z. calc.: 332.02.

X-Ray Diffraction Study.

The diffraction-quality single crystals of 1,2,3,5-azulene ($CF_3$)$_4$ were mounted in a paratone oil on a glass fiber rods glued to a small copper wire. X-ray diffraction data were collected at ChemMatCARS (CARS=Consortium for Advanced Radiation Sources) sector 15-B at the Advanced Photon Source (Argonne National Laboratory). The data sets were collected at 100(2) K using a diamond (111) crystal monochromator, a wavelength of 0.41328 Å and a Bruker CCD detector. The structure was solved using direct methods and refined (on F2, using all data) by a full-matrix, weighted least squares process. Standard Bruker control and integration software (APEX II) was employed, and Bruker SHELXTL software was used for structure solution, refinement, and graphics.

Data for 1,3,5,7-azulene($CF_3$)$_4$ and 1,2,3,5,7-azulene ($CF_3$)$_5$/pyrene were collected using a Bruker Kappa APEX II CCD diffractometer employing Mo Kα radiation and a graphite monochromator. Unit cell parameters were obtained from least-squares fits to the angular coordinates of all reflections, and intensities were integrated from a series of frames (ω and φ rotation) covering more than a hemisphere of reciprocal space. Absorption and other corrections were applied using SCALE. The structures were solved using direct methods and refined (on $F^2$, using all data) by a full-matrix, weighted least-squares process. Standard Bruker control and integration software (APEX II) was employed, and Bruker SHELXTL software was used for structure solution, refinement, and molecular graphics.

Crystal data for AZUL-4-1: $C_{14}H_4F_{12}$, M=400.17, triclinic, a=8.9064(4) Å, b=9.5245(4) Å, c=13.4137(6) Å, α=105.240(2)°, β=101.240(2)°, γ=101.091(2)°, V=1040.70 (8) Å$^3$, T=120(2) K, space group P-1, Z=3, µ(MoKα)=0.225 mm$^{-1}$, 22507 reflections measured, 5131 independent reflections ($R_{int}$=0.0268). The final $R_1$ values were 0.0497 (I>2σ (I)). The final wR($F^2$) values were 0.1173 (I>2σ(I)). The final $R_1$ values were 0.0667 (all data). The final wR($F^2$) values were 0.1283 (all data). The goodness of fit on $F^2$ was 1.045. CCDC number CCDC 980904.

Crystal data for AZUL-4-2: $C_{14}H_4F_{12}$, M=400.17, monoclinic, a=4.8939(3) Å, b=32.3450(18) Å, c=8.6013(5) Å, α=90°, β=94.4396(10)°, γ=90°, V=1357.44(14) Å$^3$, T=100 (2) K, space group Cc, Z=4, synchrotron radiation at ChemMatCARS Sector 15-B at the Advanced Photon Source at Argonne National Laboratory (diamond (111) crystal monochromator µ(diamond (111))=0.073 mm$^{-1}$; λ=0.41328 Å). 17319 reflections measured, 4394 independent reflections ($R_{int}$=0.0457). The final $R_1$ values were 0.0369 (I>2σ(I)). The final wR($F^2$) values were 0.0963 (I>2σ(I)). The final $R_1$ values were 0.0499 (all data). The final wR($F^2$) values were 0.1226 (all data). The goodness of fit on $F^2$ was 1.194. CCDC number CCDC 980900.

Crystal data for AZUL-5-1/pyrene: $C_{31}H_{13}F_{15}$, M=670.41, monoclinic, a=7.2226(7) Å, b=16.1783(17) Å, c=21.334(2)

Å, α=90°, β=92.461(5)°, γ=90°, V=2490.6(4) Å$^3$, T=120(2) K, space group P21/n, Z=4, μ(MoKα)=0.183 mm$^{-1}$, 59030 reflections measured, 7578 independent reflections ($R_{int}$=0.0293). The final $R_1$ values were 0.0396 (I>2σ(I)). The final wR(F$^2$) values were 0.1056 (I>2σ(I)). The final $R_1$ values were 0.0441 (all data). The final wR(F$^2$) values were 0.1095 (all data). The goodness of fit on F$^2$ was 1.024. CCDC number CCDC 980901.

Example 5

Perfluoroalkylation of Polyaromatic Hydrocarbons

Certain specific examples of polyaromatic hydrocarbons (PAH) that can be prepared using the methods described herein are listed below in Table 5.1. The expected range of perfluoroalkyl substituents ("n") is provided (typically 2, 3, 4, or 5 perfluoroalkyl substituents on a bicyclic system; 2-6 for a tricyclic system), which can be influenced to greater number of substituents by increasing pressure, temperature, and reaction duration from the standard conditions described in the examples above. A lesser number of substituents can be obtained by decreasing pressure, temperature, and reaction duration from the standard conditions described in the examples above. The table also provides the expected most abundant isomer (number of "$R_F$" substituents "n").

TABLE 5.1

Data for Polyheterocyclic Compound Perfluoroalkylation Products

| PAH substrate | Expected range of n in PAH($R_F$)$_n$ | Expected most abundant $n(R_F)$ |
|---|---|---|
| chrysene | 4-8 | 6, 7 |
| picene | 6-12 | 7, 8 |
| as-indacene | 3-6 | 3, 4 |
| phenalene | 2-6 | 5, 6 |
| acenaphylene | 2-6 | 4, 5 |
| biphenylene | 2-6 | 4, 5 |

Example 6

Perfluoroalkylation of Polyheterocyclic Compounds

Certain specific examples of polyheterocyclic compounds (PHC) that can be prepared using the methods described herein are listed below in Table 6.1. The expected range of perfluoroalkyl substituents ("n") is provided (typically 2, 3, 4, or 5 perfluoroalkyl substituents on a bicyclic system; 2-6 for a tricyclic system), which can be influenced to greater number of substituents by increasing pressure, temperature, and reaction duration from the standard conditions described in the examples above. A lesser number of substituents can be obtained by decreasing pressure, temperature, and reaction duration from the standard conditions described in the examples above. The table also provides the expected most abundant isomer (number of "$R_F$" substituents "n").

TABLE 6.1

Data for Polyheterocyclic Compound Perfluoroalkylation Products

| PHC substrate | Expected range of n in PHC($R_F$) | Expected most abundant $n(R_F)$ |
|---|---|---|
| isoquinoline | 2-5 | 3 |
| 4H-quinolizine | 2-5 | 4 |
| quinoline | 2-4 | 3 |
| 1,7-phenanthroline | 2-6 | 5 |
| 9H-carbazole | 2-5 | 4 |
| beta-carboline | 2-5 | 4 |

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method for preparing a purified polyaromatic hydrocarbon or polyheterocyclic compound substituted with one or more perfluoroalkyl groups comprising:
    heating a polyaromatic hydrocarbon substrate or a polyheterocyclic compound substrate in the presence of a perfluoroalkyl iodide, in an optionally closed reaction system, wherein the heating is sufficient to bring both the polyaromatic hydrocarbons or polyheterocyclic compound, and the perfluoroalkyl iodide, into the gas phase, thereby allowing the substrate to react with the perfluoroalkyl iodide in the gas phase to form polyaromatic hydrocarbons or polyheterocyclic compounds having one or more perfluoroalkyl substituents; and
    isolating the polyaromatic hydrocarbons or polyheterocyclic compounds having one or more perfluoroalkyl substituents by chromatography performed with an HPLC column that has a stationary phase comprising 3-(1-prenyl)propyl groups.

2. The method of claim 1 wherein the reaction system containing the substrate and perfluoroalkyl iodide is heated to about 200° C. to about 450° C.

3. The method of claim 1 wherein the reaction system is a closed system that provides an increased atmospheric pressure upon heating.

4. The method of claim 1 wherein the reaction system does not comprise a catalyst, a reaction promoter, or solvent.

5. The method of claim 1 wherein the perfluoroalkyl iodide is CF$_3$(CF$_2$)$_n$I, wherein n is 0 to about 12.

6. The method of claim 5 wherein the perfluoroalkyl iodide is CF$_3$I, C$_2$F$_5$I, n-C$_3$F$_7$I, n-C$_4$F$_9$I, n-C$_6$F$_{13}$I, or n-C$_8$F$_{17}$I.

7. The method of claim 1 wherein the substrate is a polyaromatic hydrocarbon substrate.

8. The method of claim 7 wherein the polyaromatic hydrocarbon substrate is anthracene, azulene, coronene, fluorene, fluoranthene, naphthalene, pentacene, perylene, phenanthrene, pyrene, tetracene, or triphenylene.

9. The method of claim 1 wherein the substrate is a polyheterocyclic compound substrate.

10. The method of claim 9 wherein the polyheterocyclic compound substrate is acridine, beta-carboline, 9H-carbazole, iminodibenzyl, indole, isoquinoline, phenanthridine phenanthroline, phenazine, phenothiazine, quinazoline, or quinoline.

11. The method of claim 8 wherein the polyaromatic hydrocarbon having one or more perfluoroalkyl substituents formed is a compound of Formula (I):

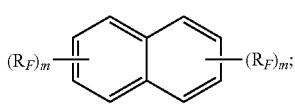

wherein $R_F$ is —$(CF_2)_nCF_3$ wherein n is 0 to about 11; and each m is independently 1 to 3.

12. The method of claim 11 wherein the compound of Formula (I) is:

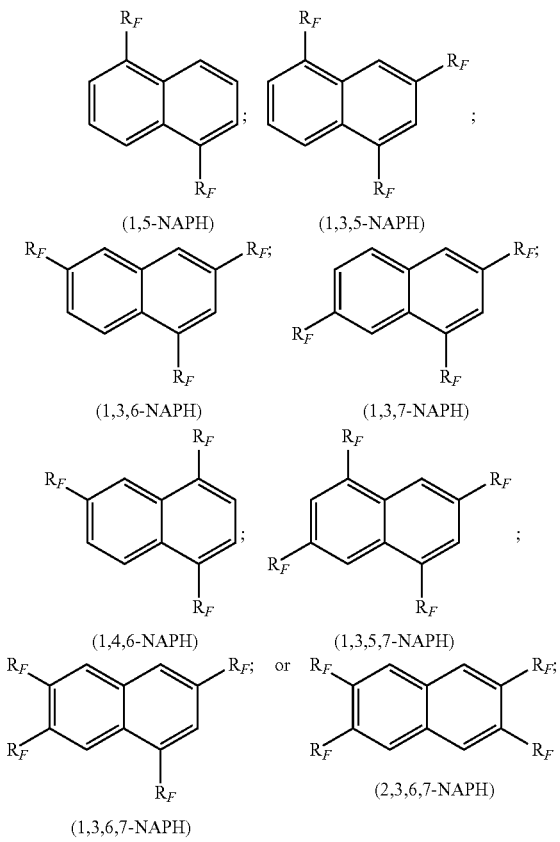

wherein $R_F$ is —$(CF_2)_nCF_3$ wherein n is 0 to about 11.

13. The method of claim 8 wherein the polyaromatic hydrocarbon having one or more perfluoroalkyl substituents formed is a compound of Formula (II):

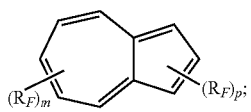

wherein $R_F$ is —$(CF_2)_nCF_3$ wherein n is 0 to about 11;

m is 0 to 3; and p is 1 to 3.

14. The method of claim 13 wherein the compound of Formula (II) is:

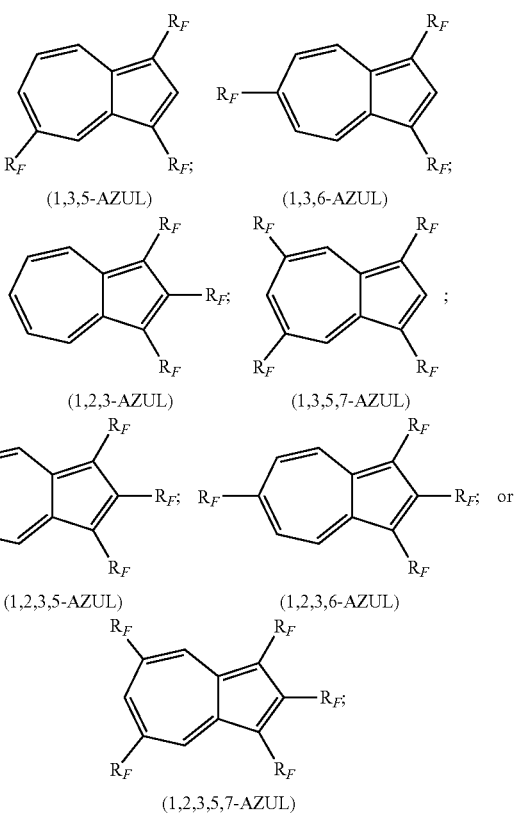

wherein $R_F$ is —$(CF_2)_nCF_3$ wherein n is 0 to about 11.

15. The method of claim 8 wherein the polyaromatic hydrocarbon having one or more perfluoroalkyl substituents formed is:

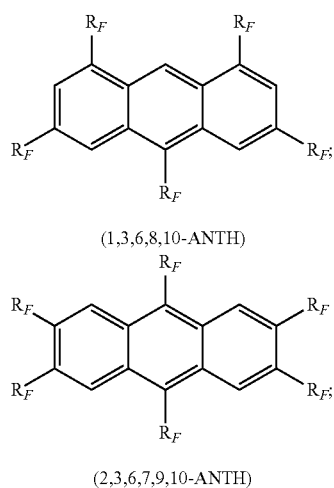

-continued
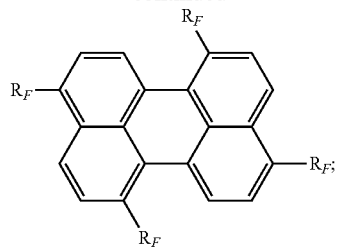
(1,4,7,10-PERY)
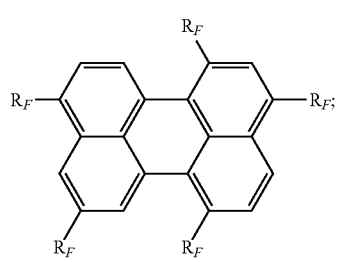
(1,3,6,8,10-PERY)
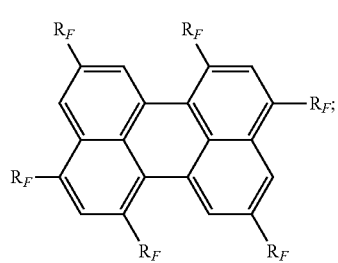
(1,3,5,7,9,11-PERY)
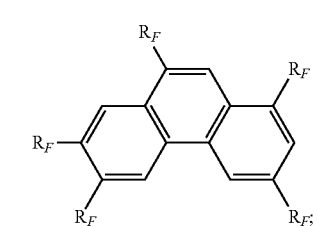
(1,3,6,7,9-PHEN)
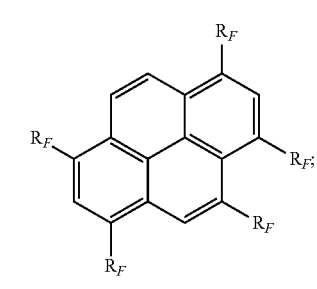
(1,3,4,6,8-PYRN)
-continued
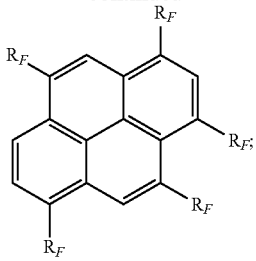
(1,3,4,6,9-PYRN)
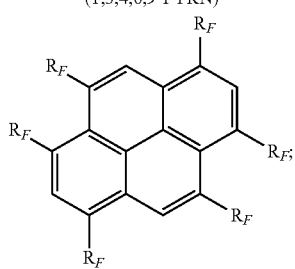
(1,3,4,6,8,9-PYRN)
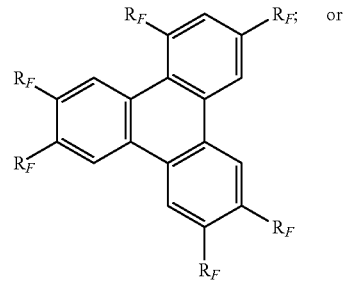
(1,3,6,7,10,11-TRPH)
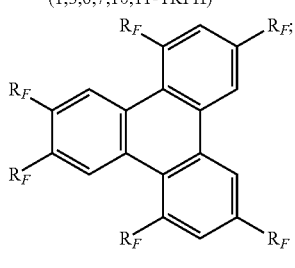
(1,3,6,8,10,11-TRPH)
wherein $R_F$ is $-(CF_2)_nCF_3$ wherein n is 0 to about 11.
16. The method of claim 8 wherein the polyaromatic hydrocarbon having one or more perfluoroalkyl substituents formed is a compound of Formula (III):
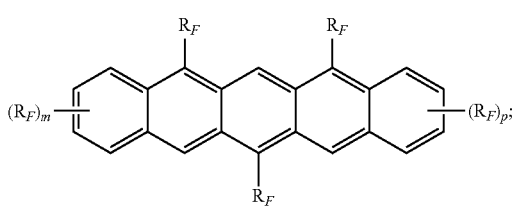
(III)

a compound of Formula (IV):

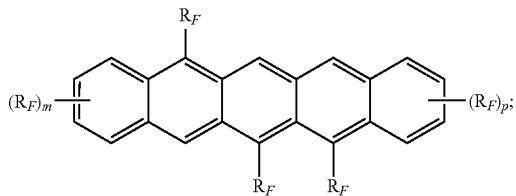

a compound of Formula (V):

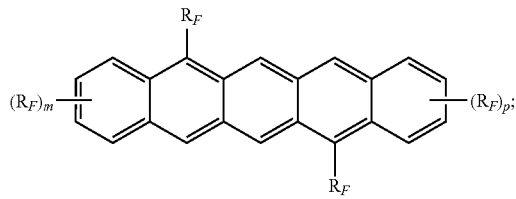

a compound of Formula (VI):

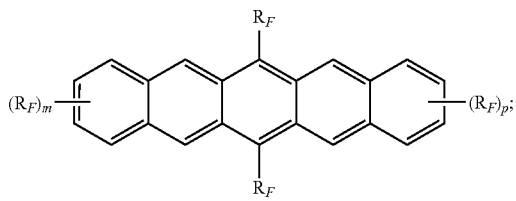

or
a compound of Formula (VII):

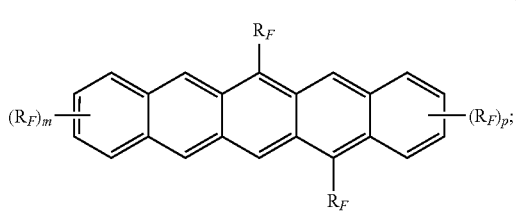

wherein
$R_F$ is —$(CF_2)_n CF_3$ wherein n is 0 to about 11;
m is 0 to 3;
p is 0 to 3; and
wherein the sum of m and p is 2, 3, 4, 5, or 6.

17. The method of claim 10 wherein the polyheterocyclic compound having one or more perfluoroalkyl substituents formed is a compound of Formula (X):

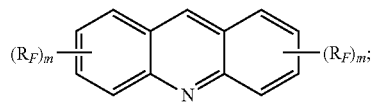

a compound of Formula (XI):

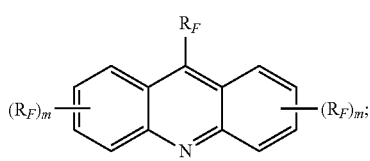

a compound of Formula (XII):

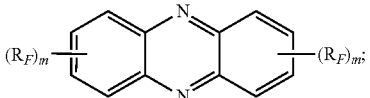

a compound of Formula (XIII):

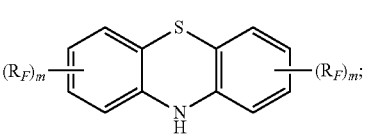

a compound of Formula (XIV):

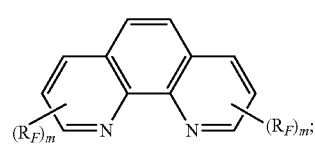

or
a compound of Formula (XV):

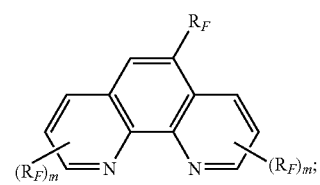

wherein
each $R_F$ is independently —$(CF_2)_n CF_3$ wherein n is 0 to about 11;
each m is independently 0 to 3; and
wherein the sum of elements m is 1, 2, 3, 4, or 5.

18. A method for preparing a purified polyaromatic hydrocarbon or polyheterocyclic compound substituted with one or more trifluoromethyl groups comprising:

heating a polyaromatic hydrocarbon substrate or a polyheterocyclic compound substrate in the presence of a trifluoromethyl iodide, in an optionally closed reaction system, wherein the heating is sufficient to bring both the polyaromatic hydrocarbons or polyheterocyclic compound, and the perfluoroalkyl iodide, into the gas phase, thereby allowing the substrate to react with the perfluoroalkyl iodide in the gas phase to form polyaromatic hydrocarbons or polyheterocyclic compounds having one or more perfluoroalkyl substituents; and isolating the polyaromatic hydrocarbons or polyheterocyclic compounds having one or more perfluoroalkyl substituents by chromatography performed with an HPLC column that has a stationary phase comprising 3-(1-prenyl)propyl groups, wherein the chromatography performed with an HPLC column provides single isomers of the substituted polyaromatic hydrocarbons or polyheterocyclic compounds.

19. The method of claim 1, wherein the chromatography performed with an HPLC column provides single isomers of the substituted polyaromatic hydrocarbons or polyheterocyclic compounds.

* * * * *